(12) United States Patent
Terracciano et al.

(10) Patent No.: US 10,420,841 B2
(45) Date of Patent: *Sep. 24, 2019

(54) CEFTOLOZANE ANTIBIOTIC COMPOSITIONS

(71) Applicant: Merck Sharp & Dohme Corp., Rahway, NJ (US)

(72) Inventors: Joseph Terracciano, Concord, MA (US); Nicole Miller Damour, Belmont, MA (US); Chun Jiang, Hillsborough, CA (US); Giovanni Fogliato, Barzana (IT); Giuseppe Alessandron Donadelli, Lodi (IT); Dario Resemini, Milan (IT)

(73) Assignee: Merck, Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,961

(22) Filed: Dec. 18, 2017

(65) Prior Publication Data

US 2018/0104338 A1    Apr. 19, 2018

Related U.S. Application Data

(63) Continuation of application No. 14/856,075, filed on Sep. 16, 2015, now Pat. No. 9,872,906, which is a continuation-in-part of application No. 14/251,381, filed on Apr. 11, 2014, now abandoned, which is a continuation of application No. PCT/US2014/028642, filed on Mar. 14, 2014.

(60) Provisional application No. 62/051,859, filed on Sep. 17, 2014, provisional application No. 61/893,436, filed on Oct. 21, 2013, provisional application No. 61/882,936, filed on Sep. 26, 2013, provisional application No. 61/793,007, filed on Mar. 15, 2013, provisional application No. 61/792,092, filed on Mar. 15, 2013.

(51) Int. Cl.
| | | |
|---|---|---|
| A61K 31/431 | (2006.01) | |
| A61K 31/546 | (2006.01) | |
| A61K 47/02 | (2006.01) | |
| A61K 9/00 | (2006.01) | |
| A61K 47/18 | (2017.01) | |
| A61K 9/19 | (2006.01) | |
| A61K 47/12 | (2006.01) | |

(52) U.S. Cl.
CPC ............ *A61K 47/02* (2013.01); *A61K 9/0019* (2013.01); *A61K 9/19* (2013.01); *A61K 31/431* (2013.01); *A61K 31/546* (2013.01); *A61K 47/183* (2013.01); *A61K 47/12* (2013.01)

(58) Field of Classification Search
None
See application file for complete search history.

(56) References Cited

U.S. PATENT DOCUMENTS

| | | |
|---|---|---|
| 4,200,575 A | 4/1980 | Numata et al. |
| 4,246,405 A | 1/1981 | Takaya et al. |
| 4,255,431 A | 3/1981 | Junggren et al. |
| 4,264,597 A | 4/1981 | Hashimoto et al. |
| 4,267,176 A | 5/1981 | Kamiya et al. |
| 4,268,509 A | 5/1981 | Teraji et al. |
| 4,284,631 A | 8/1981 | Takaya et al. |
| 4,291,031 A | 9/1981 | Takaya et al. |
| 4,298,529 A | 11/1981 | Ueda et al. |
| 4,299,829 A | 11/1981 | Kamiya et al. |
| 4,305,937 A | 12/1981 | Kamiya et al. |
| 4,327,093 A | 4/1982 | Ueda et al. |
| 4,331,665 A | 5/1982 | Teraji et al. |
| 4,332,798 A | 6/1982 | Teraji et al. |
| 4,332,800 A | 6/1982 | Teraji et al. |
| 4,336,253 A | 6/1982 | Lunn |
| 4,338,313 A | 7/1982 | Teraji et al. |
| 4,339,449 A | 7/1982 | Hashimoto et al. |
| 4,363,807 A | 12/1982 | Takaya et al. |
| 4,367,228 A | 1/1983 | Takaya et al. |
| 4,368,325 A | 1/1983 | Ueda et al. |
| 4,369,312 A | 1/1983 | Hashimoto et al. |
| 4,370,326 A | 1/1983 | Takaya et al. |
| 4,381,299 A | 4/1983 | Teraji et al. |
| 4,390,534 A | 6/1983 | Teraji et al. |
| 4,394,384 A | 7/1983 | Takaya et al. |

(Continued)

FOREIGN PATENT DOCUMENTS

| | | |
|---|---|---|
| AU | 614793 B1 | 5/1989 |
| AU | 707730 B2 | 5/1996 |

(Continued)

OTHER PUBLICATIONS

Abstract for Brown et al. Activity profile of CXA-101 against gram-positive and gram-negative pathogens by broth and agar dilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-354; This poster is obtainable at: http://www.eurofins.com/media/694466/Calixe/020F1-354%20broth%20agar%20v6.pdf.

(Continued)

*Primary Examiner* — Emily A Bernhardt
*Assistant Examiner* — Laura M Daniel
(74) *Attorney, Agent, or Firm* — J. Eric Thies; John C. Todaro

(57) ABSTRACT

This disclosure provides pharmaceutical compositions comprising ceftolozane, pharmaceutical compositions comprising ceftolozane and tazobactam, methods of preparing those compositions, and related methods and uses of these compositions.

31 Claims, 15 Drawing Sheets

(56) References Cited

U.S. PATENT DOCUMENTS

| | | |
|---|---|---|
| 4,402,955 A | 9/1983 | Lunn |
| 4,405,617 A | 9/1983 | Takaya et al. |
| 4,407,798 A | 10/1983 | Kamiya et al. |
| 4,409,214 A | 10/1983 | Takaya et al. |
| 4,409,215 A | 10/1983 | Takaya et al. |
| 4,409,217 A | 10/1983 | Takaya et al. |
| 4,416,879 A | 11/1983 | Takaya et al. |
| 4,418,058 A | 11/1983 | Hirai et al. |
| 4,420,477 A | 12/1983 | Takaya et al. |
| 4,423,213 A | 12/1983 | Takaya et al. |
| 4,425,340 A | 1/1984 | Teraji et al. |
| 4,425,341 A | 1/1984 | Takaya et al. |
| 4,427,677 A | 1/1984 | Takaya et al. |
| 4,431,642 A | 1/1984 | Teraji et al. |
| 4,430,499 A | 2/1984 | Wheeler |
| 4,436,912 A | 3/1984 | Wheeler |
| 4,438,113 A | 3/1984 | Takaya et al. |
| 4,443,443 A | 4/1984 | Ueda et al. |
| 4,443,444 A | 4/1984 | Takaya et al. |
| 4,447,429 A | 5/1984 | Teraji et al. |
| 4,450,270 A | 5/1984 | Lunn |
| 4,452,851 A | 6/1984 | Takaya et al. |
| 4,457,928 A | 7/1984 | Teraji et al. |
| 4,462,999 A | 7/1984 | Takaya et al. |
| 4,463,000 A | 7/1984 | Teraji et al. |
| 4,463,002 A | 7/1984 | Takaya et al. |
| 4,463,003 A | 7/1984 | Takaya et al. |
| 4,464,369 A | 8/1984 | Takaya et al. |
| 4,470,980 A | 9/1984 | Higuchi et al. |
| 4,474,779 A | 10/1984 | Nagano et al. |
| 4,477,447 A | 10/1984 | Ueda et al. |
| 4,487,768 A | 12/1984 | Takaya et al. |
| 4,495,182 A | 1/1985 | Teraji et al. |
| 4,496,562 A | 1/1985 | Takaya et al. |
| 4,499,088 A | 2/1985 | Takaya et al. |
| 4,501,739 A | 2/1985 | Lunn et al. |
| 4,515,788 A | 5/1985 | Takaya et al. |
| 4,521,413 A | 6/1985 | Teraji et al. |
| 4,529,592 A | 7/1985 | Micetich et al. |
| 4,546,101 A | 10/1985 | Takaya et al. |
| 4,550,102 A | 10/1985 | Teraji et al. |
| 4,559,334 A | 12/1985 | Takaya et al. |
| 4,562,073 A | 12/1985 | Micetich et al. |
| 4,563,449 A | 1/1986 | Teraji et al. |
| 4,577,014 A | 3/1986 | Lunn et al. |
| 4,584,290 A | 4/1986 | Takaya et al. |
| 4,585,872 A | 4/1986 | Teraji et al. |
| 4,590,186 A | 5/1986 | Takaya et al. |
| 4,600,772 A | 7/1986 | O'Callaghan et al. |
| 4,608,373 A | 8/1986 | Shibanuma et al. |
| 4,609,730 A | 9/1986 | Takaya et al. |
| 4,616,083 A | 10/1986 | Shima et al. |
| 4,622,318 A | 11/1986 | Takaya et al. |
| 4,626,384 A | 12/1986 | Tanaka et al. |
| 4,631,274 A | 12/1986 | Takaya et al. |
| 4,640,915 A | 2/1987 | Hashimoto et al. |
| 4,647,556 A | 3/1987 | Lattrell et al. |
| 4,667,028 A | 5/1987 | Schwab et al. |
| 4,690,921 A | 9/1987 | Shibanuma et al. |
| 4,692,443 A | 9/1987 | Katner |
| 4,698,337 A | 10/1987 | Takaya et al. |
| 4,699,980 A | 10/1987 | Shibanuma et al. |
| 4,703,046 A | 10/1987 | Ueda et al. |
| 4,705,851 A | 11/1987 | Takaya et al. |
| 4,735,937 A | 4/1988 | Heusler et al. |
| 4,748,172 A | 5/1988 | Katner |
| 4,761,410 A | 8/1988 | Takaya et al. |
| 4,764,606 A | 8/1988 | Imai et al. |
| 4,769,183 A | 9/1988 | Kawamata et al. |
| 4,808,617 A | 2/1989 | Kaplan et al. |
| 4,808,711 A | 2/1989 | Shimizu et al. |
| 4,822,785 A | 4/1989 | Ishibashi et al. |
| 4,822,787 A | 4/1989 | Murata et al. |
| 4,833,134 A | 5/1989 | Kishimoto et al. |
| 4,861,769 A | 8/1989 | Takaya et al. |
| 4,868,174 A | 9/1989 | Takaya et al. |
| 4,871,730 A | 10/1989 | Takaya et al. |
| 4,882,434 A | 11/1989 | Yoshioka |
| 4,921,852 A | 5/1990 | Murata et al. |
| 4,923,857 A | 5/1990 | Murata et al. |
| 4,925,934 A | 5/1990 | Taniguchi et al. |
| 4,927,818 A | 5/1990 | Takaya et al. |
| 4,935,507 A | 6/1990 | Takaya et al. |
| 4,943,567 A | 7/1990 | Nishizawa et al. |
| 4,952,578 A | 8/1990 | Sakane et al. |
| 4,960,766 A | 10/1990 | Takaya et al. |
| 4,963,543 A | 10/1990 | Murata et al. |
| 4,963,544 A | 10/1990 | Murata et al. |
| 4,971,962 A | 11/1990 | Oh et al. |
| 4,982,596 A | 1/1991 | Peterson et al. |
| 5,036,064 A | 7/1991 | Gotschi |
| RE33,778 E | 12/1991 | Iwanami et al. |
| 5,071,979 A | 12/1991 | Lattrell et al. |
| 5,073,550 A | 12/1991 | Gotschi |
| 5,081,116 A | 1/1992 | Nagano et al. |
| 5,095,012 A | 3/1992 | Okita et al. |
| 5,102,877 A | 4/1992 | Murata et al. |
| 5,104,866 A | 4/1992 | Sakane et al. |
| 5,108,997 A | 4/1992 | Takaya et al. |
| 5,109,130 A | 4/1992 | Sakane et al. |
| 5,138,066 A | 6/1992 | Gotschi |
| 5,159,070 A | 10/1992 | Heymes et al. |
| 5,162,520 A | 11/1992 | Takaya et al. |
| 5,173,485 A | 12/1992 | Sakane et al. |
| 5,179,485 A | 1/1993 | Tamayama |
| 5,187,160 A | 2/1993 | Sakane et al. |
| 5,194,432 A | 3/1993 | Takaya et al. |
| 5,210,080 A | 5/1993 | Takaya et al. |
| 5,215,982 A | 6/1993 | Sakane et al. |
| 5,215,983 A | 6/1993 | Murata et al. |
| 5,219,848 A | 6/1993 | Hennequin et al. |
| 5,234,920 A | 8/1993 | Okita et al. |
| 5,244,890 A | 9/1993 | Yamanaka et al. |
| 5,281,589 A | 1/1994 | Kim et al. |
| 5,286,721 A | 2/1994 | Murata et al. |
| 5,319,140 A | 6/1994 | Gotschi |
| 5,329,002 A | 7/1994 | Albrecht et al. |
| 5,336,768 A | 8/1994 | Albrecht et al. |
| 5,366,970 A | 11/1994 | Sakane et al. |
| 5,389,627 A | 2/1995 | Kim et al. |
| 5,498,787 A | 3/1996 | Wang et al. |
| 5,523,400 A | 6/1996 | Wei et al. |
| 5,637,580 A | 6/1997 | White et al. |
| 5,646,139 A | 7/1997 | White et al. |
| 5,648,346 A | 7/1997 | White et al. |
| 5,656,623 A | 8/1997 | White et al. |
| 5,661,144 A | 8/1997 | Tsushima et al. |
| 5,663,163 A | 9/1997 | Takaya et al. |
| 5,763,603 A | 6/1998 | Trickes |
| 6,207,661 B1 | 3/2001 | Thompson et al. |
| 6,214,818 B1 | 4/2001 | Nishitani et al. |
| 6,235,311 B1 | 5/2001 | Ullah et al. |
| 6,458,950 B1 | 10/2002 | Nishitani et al. |
| 6,518,263 B1 | 2/2003 | Nishitani et al. |
| 6,660,855 B2 | 12/2003 | Shimabayashi et al. |
| 6,774,104 B1 | 8/2004 | Sawai et al. |
| 6,800,621 B2 | 10/2004 | Nishitani et al. |
| 6,878,686 B2 | 4/2005 | Marquess et al. |
| 6,936,711 B2 | 8/2005 | Deshpande et al. |
| 6,974,797 B2 | 12/2005 | Fatheree et al. |
| 6,995,138 B2 | 2/2006 | Marquess et al. |
| 7,067,462 B2 | 6/2006 | Fatheree et al. |
| 7,067,481 B2 | 6/2006 | Fatheree et al. |
| 7,112,565 B2 | 9/2006 | Sawai et al. |
| 7,129,232 B2 | 10/2006 | Ohki et al. |
| 7,179,801 B2 | 2/2007 | Ohki et al. |
| 7,192,943 B2 | 3/2007 | Yamanaka et al. |
| 7,273,935 B2 | 5/2007 | Deshpande et al. |
| 7,279,458 B2 | 10/2007 | Fatheree et al. |
| 7,304,075 B2 | 12/2007 | Araki et al. |
| 7,332,471 B2 | 2/2008 | Fatheree et al. |
| 7,341,993 B2 | 3/2008 | Fatheree et al. |
| 7,378,408 B2 | 5/2008 | Kimball et al. |
| 7,384,928 B2 | 6/2008 | Nishitani et al. |

(56) References Cited

U.S. PATENT DOCUMENTS

| | | |
|---|---|---|
| 7,417,143 B2 | 8/2008 | Gnanaprakasam et al. |
| 7,547,777 B2 | 6/2009 | Tokumaru et al. |
| 7,553,962 B2 | 6/2009 | Fatheree et al. |
| 7,601,690 B2 | 10/2009 | Fatheree et al. |
| 7,612,037 B2 | 11/2009 | Fatheree et al. |
| 7,649,080 B2 | 1/2010 | Fatheree et al. |
| 7,655,621 B2 | 2/2010 | Fatheree et al. |
| 7,842,683 B2 | 3/2010 | Shimabayashi et al. |
| 7,728,127 B2 | 6/2010 | Fatheree et al. |
| 7,915,229 B2 | 3/2011 | Cohen et al. |
| 8,133,883 B2 | 3/2012 | Cohen et al. |
| 8,476,245 B2 | 7/2013 | Lai et al. |
| 8,476,425 B1 | 7/2013 | Lai et al. |
| 8,685,957 B1 | 4/2014 | Lai et al. |
| 8,809,314 B1 | 8/2014 | He et al. |
| 8,906,898 B1 | 12/2014 | Hwang et al. |
| 8,968,753 B2 | 3/2015 | Terracciano et al. |
| 9,006,421 B2 | 4/2015 | Lai et al. |
| 9,320,740 B2 | 4/2016 | Terracciano et al. |
| 2002/0115650 A1 | 8/2002 | Glinka |
| 2002/0193587 A1 | 12/2002 | Shimabayashi et al. |
| 2003/0130173 A1 | 7/2003 | Fatheree et al. |
| 2003/0232983 A1 | 12/2003 | Deshpande et al. |
| 2005/0171077 A1 | 8/2005 | Ruppen et al. |
| 2005/0228176 A1 | 10/2005 | Gnanaprakasam et al. |
| 2006/0051412 A1 | 3/2006 | Petereit et al. |
| 2006/0084639 A1 | 4/2006 | Cohen et al. |
| 2006/0099253 A1 | 5/2006 | Becker et al. |
| 2006/0173177 A1 | 8/2006 | Gego et al. |
| 2006/0241017 A1 | 10/2006 | Chandran |
| 2006/0269485 A1 | 11/2006 | Friedman et al. |
| 2006/0287244 A1 | 12/2006 | Chandran |
| 2006/0293516 A1 | 12/2006 | Wada et al. |
| 2007/0054899 A1 | 3/2007 | Park et al. |
| 2007/0116770 A1 | 5/2007 | Garms et al. |
| 2007/0219191 A1 | 9/2007 | Nishitani et al. |
| 2007/0286817 A1 | 12/2007 | Tatapudy et al. |
| 2007/0286818 A1 | 12/2007 | Tatapudy et al. |
| 2008/0015156 A1 | 1/2008 | Udayampalayam Palanisamy et al. |
| 2008/0103121 A1 | 5/2008 | Gole et al. |
| 2008/0160067 A1 | 7/2008 | Boeckh et al. |
| 2008/0233196 A1 | 9/2008 | Cattaneo et al. |
| 2009/0098088 A1 | 4/2009 | Taylor et al. |
| 2009/0137460 A1 | 5/2009 | Marquess et al. |
| 2009/0155387 A1 | 6/2009 | Zhang |
| 2009/0156517 A1 | 6/2009 | Zhang |
| 2009/0156518 A1 | 6/2009 | Zhang |
| 2009/0186865 A1 | 7/2009 | Diago et al. |
| 2009/0227554 A1 | 9/2009 | Liversidge et al. |
| 2009/0274662 A1 | 11/2009 | Magowan et al. |
| 2009/0275552 A1 | 11/2009 | Patel et al. |
| 2009/0291102 A1 | 11/2009 | Fortin |
| 2009/0311234 A1 | 12/2009 | Koski et al. |
| 2010/0040548 A1 | 2/2010 | Yu |
| 2010/0286031 A1 | 11/2010 | Charan et al. |
| 2011/0044917 A1 | 2/2011 | Tosetti |
| 2011/0136763 A1 | 6/2011 | Xia et al. |
| 2011/0190252 A1 | 8/2011 | Watson et al. |
| 2011/0257079 A1 | 10/2011 | Chaudhary et al. |
| 2013/0065874 A1 | 3/2013 | Chandorkar et al. |
| 2013/0289012 A1 | 10/2013 | Gu et al. |
| 2013/0296290 A1 | 11/2013 | Gu et al. |
| 2013/0296291 A1 | 11/2013 | Gu et al. |
| 2013/0296292 A1 | 11/2013 | Gu et al. |
| 2013/0296293 A1 | 11/2013 | Gli et al. |
| 2013/0296555 A1 | 11/2013 | Gu et al. |
| 2013/0303504 A1 | 11/2013 | Gu et al. |
| 2013/0345190 A1 | 12/2013 | Gu et al. |
| 2014/0187528 A1* | 7/2014 | Lai ................... A61K 31/155 514/192 |
| 2014/0213567 A1 | 7/2014 | Lai et al. |
| 2014/0206659 A1 | 9/2014 | Lai et al. |
| 2014/0262868 A1 | 9/2014 | Terracciano et al. |
| 2014/0274989 A1 | 9/2014 | Terracciano et al. |
| 2014/0274990 A1 | 9/2014 | Terracciano et al. |
| 2014/0274991 A1 | 9/2014 | Damour et al. |
| 2014/0274992 A1 | 9/2014 | Damour et al. |
| 2014/0274993 A1 | 9/2014 | Terracciano et al. |
| 2014/0274994 A1 | 9/2014 | Damour et al. |
| 2014/0274995 A1 | 9/2014 | Zhou et al. |
| 2014/0274996 A1 | 9/2014 | Damour et al. |
| 2014/0274997 A1 | 9/2014 | Zhou et al. |
| 2014/0274998 A1 | 9/2014 | Terracciano et al. |
| 2014/0275000 A1 | 9/2014 | Damour et al. |
| 2014/0303136 A1 | 9/2014 | Terracciano et al. |
| 2014/0309205 A1 | 9/2014 | Terracciano et al. |

FOREIGN PATENT DOCUMENTS

| | | |
|---|---|---|
| AU | 2002952355 | 10/2002 |
| AU | 2003904813 | 9/2003 |
| AU | 2003905084 | 9/2003 |
| CA | 1235689 A1 | 4/1988 |
| CA | 2140701 A1 | 7/1995 |
| CN | 99100092 | 12/1999 |
| CN | 200410067367 | 4/2006 |
| CN | 200810092568 | 10/2008 |
| CN | 200810238479 | 5/2009 |
| CN | 200910169647 | 4/2010 |
| CN | 201010557481 | 4/2011 |
| CN | 201110061045 | 3/2012 |
| EP | 0047977 A1 | 9/1981 |
| EP | 0097446 A1 | 1/1984 |
| EP | 0137440 | 4/1985 |
| EP | 0137442 A2 | 4/1985 |
| EP | 0138552 | 4/1985 |
| EP | 0111934 B1 | 8/1988 |
| EP | 0318767 A2 | 6/1989 |
| EP | 0664117 A1 | 7/1995 |
| EP | 0711774 B1 | 5/1996 |
| EP | 0771803 A1 | 5/1997 |
| EP | 1273586 A1 | 1/2003 |
| EP | 1285923 A1 | 2/2003 |
| EP | 1468697 A1 | 10/2004 |
| EP | 1134222 B1 | 4/2005 |
| EP | 1554287 | 7/2005 |
| EP | 1671974 A1 | 6/2006 |
| EP | 1686131 A2 | 8/2006 |
| EP | 1759697 A1 | 3/2007 |
| EP | 1787641 A1 | 5/2007 |
| EP | 1959933 | 8/2008 |
| EP | 1974721 A1 | 10/2008 |
| EP | 2015755 | 1/2009 |
| EP | 2062581 A1 | 5/2009 |
| EP | 2062582 A1 | 5/2009 |
| EP | 2062585 A1 | 5/2009 |
| EP | 2136844 | 12/2009 |
| EP | 2305251 A2 | 4/2011 |
| EP | 1154770 | 11/2011 |
| JP | 62103092 A | 5/1987 |
| JP | 62158290 A | 7/1987 |
| JP | 63051388 A | 3/1988 |
| JP | 63051389 A | 3/1988 |
| JP | 2088582 A | 3/1990 |
| JP | 2117678 A | 5/1990 |
| JP | 04288086 A | 10/1992 |
| JP | 4288086 A | 10/1992 |
| JP | 5222058 A | 8/1993 |
| JP | 6056848 A | 3/1994 |
| JP | 6128268 A | 5/1994 |
| JP | 2005162670 A | 6/2005 |
| WO | 199512601 A1 | 5/1995 |
| WO | 199741128 A1 | 11/1997 |
| WO | WO 99/28308 | 6/1999 |
| WO | WO 99/64049 | 12/1999 |
| WO | WO0004915 A1 | 2/2000 |
| WO | 200050035 A2 | 8/2000 |
| WO | 2002090363 A1 | 11/2002 |
| WO | 2002090364 A1 | 11/2002 |
| WO | 2002092605 A1 | 11/2002 |
| WO | 2002102378 A1 | 12/2002 |
| WO | 2003066053 A1 | 8/2003 |
| WO | WO 2003/078440 | 9/2003 |

(56) References Cited

FOREIGN PATENT DOCUMENTS

| | | |
|---|---|---|
| WO | 2003104241 A1 | 12/2003 |
| WO | 2004019901 A1 | 3/2004 |
| WO | 2004039776 A2 | 5/2004 |
| WO | WO 2004/048551 | 6/2004 |
| WO | 2004066976 A1 | 8/2004 |
| WO | 2004098643 A1 | 11/2004 |
| WO | WO 2005/005436 | 1/2005 |
| WO | 2005074925 A1 | 8/2005 |
| WO | 2006044600 A1 | 4/2006 |
| WO | 2006045006 A1 | 4/2006 |
| WO | 2006088305 A1 | 8/2006 |
| WO | 2007065862 A1 | 6/2007 |
| WO | 2007086011 A1 | 8/2007 |
| WO | 2007086013 A1 | 8/2007 |
| WO | 2007086014 A1 | 8/2007 |
| WO | 2007099396 A2 | 9/2007 |
| WO | 2007129176 A2 | 11/2007 |
| WO | 2007145866 A1 | 12/2007 |
| WO | 2007145868 A1 | 12/2007 |
| WO | 2008030469 A2 | 3/2008 |
| WO | 2008065247 A1 | 6/2008 |
| WO | 2008075207 A2 | 6/2008 |
| WO | 2008101743 A2 | 8/2008 |
| WO | 2008113177 A1 | 9/2008 |
| WO | 2009048603 A1 | 4/2009 |
| WO | WO 2009/105782 | 8/2009 |
| WO | 2009122252 A2 | 10/2009 |
| WO | 2009134948 A1 | 11/2009 |
| WO | 2010014285 A1 | 2/2010 |
| WO | 2010142241 A1 | 12/2010 |
| WO | 2011101710 A1 | 8/2011 |
| WO | 2011112435 A1 | 9/2011 |
| WO | 2011127200 A2 | 10/2011 |
| WO | WO2013036783 A2 | 3/2013 |
| WO | WO 2014/052799 | 4/2014 |

OTHER PUBLICATIONS

Abstract for Brown et al. Activity profile of CXA-101 and CXA-101/tazobactam against target gram-positive and gram-negative pathogens. 49th Annual Interscience Conference on Antimicrobial Agents and Chemotherapy (ICAAC 2009); 12th-15th, 2009. Poster F1-1986; This poster is obtainable at: http://www.eurofins.com/media/767069/Final%20F1-1986.pdf.

Abstract for Brown et al. Effect of various testing parameters on the activity of CXA-101 by broth microdilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-357; This poster is obtainable at: http://www.eurofins.com/media/694469/CW/020F1-357%20parameter%20v6.pdf.

Abstract for Brown et al. Mode of action of CXA-101 based on minimum bactericidal concentration analysis and time-kill kinetic analysis. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-358; This poster is obtainable at: http://www.eurofins.com/media/694472/CXA%20F1-358°/020tV/020mbe/020v5.pdf.

Abstract for Brown et al., Disk diffusion testing of CXA-101 and CXA-101 in combination with tazobactam against target pathogens. 49th Annual Interscience Conference on Antimicrobial Agents and Chemotherapy (ICAAC 2009); 12th-15th, 2009. Poster F1-1998; This poster is obtainable at: http:/lwww.eurofins.com/media/767072/Final%20F1-1998.pdf.

Abstract for Brown et al., Quality control parameters for CXA-101 broth microdilution susceptibility tests. 49th Annual Interscience Conference on Antimicrobial Agents and Chemotherapy (ICAAC 2009); Sep. 12-15, 2009. Poster F1-1997.

Abstract for Bulik et al. In vivo Comparison of CXA-101 (FR264205) with and without Tazobactam verus Piperacillin-Tazobactam Using Human Simulated Exposures against Phenotypically Diverse Gram-Negative Organisms. ICAAC 2010. Poster A1-1381; This poster is obtainable at: http://www.cubist.com/downloads/Bulik_PP_ICAAC_2010_in_vivo_CXA-101_vs_TZP_against_gram_neg.pdf.

Abstract for Cabot et al. Activity of CXA-101 Against a Large Collection of P. aeruginosa Blood Stream Isolates Dverexpressing AmpC and the Major Efflux Pumps. 50th Annual Interscience Conference on Antimicrobial Agents and Chemotherapy (ICAAC 2010); Sep. 12-15, 2010. Poster E-816.

Abstract for Chandorkar et al. Penetration of Ceftolozane/Tazobactam and Piperacillin/Tazobactam into the Epithelial lining of Fluid of Healthy Volunteers. 22nd Annual Meeting of the European Congress of Clinical Microbiology (ECCMID 2012); Mar. 31-Apr. 3, 2012. Poster P1627.

Abstract for Chandorkar et al. Intrapulmonary penetration of CXA-201 and Piperacillin/tazobactam in healthy adult subjects. 49th Annual Meeting of the Infectious Diseases Society of America (IDSA 2011); Oct. 20-23, 2011. Poster 611.

Abstract for Craig et al., In vivo activity of CXA-101 plus a 2:1, 4:1, or 8:1 ratio of tazobactam against various Enterobacteriaceae producing Extended-spectrum beta-lactamases in the thighs of neutropenic mice. 49th Annual Interscience Conference on Antimicrobial Agents and Chemotherapy (ICAAC 2009); Sep. 12-15, 2009. Poster F1-1999.

Abstract for Craig et al., In vivo activity of CXA-101, a new cephalosporin, against Pseudomonas aeruginosa and other Enterobacteriaceae in the thighs of neutropenic mice. 49th Annual Interscience Conference on Antimicrobial Agents and Chemotherapy (ICAAC 2009); Sep. 12-15, 2009. Poster F1-2002.

Abstract for Fenneteau et al. Population PK/PD Modeling and Simulations of a Fixed-Dose Combination of CXA-101 and Tazobactam to Optimize Dosing Strategies in Renally Impaired Patients with Complicated Urinary Tract Infection. 3rd Biennial American Conference on Pharmacometrics (ACop 2011); Apr. 3-6, 2011; This poster is obtainable at: http://www.go-acop.org/sites/default/files/webform/posters/ACOP2011%20-%020Dosing%20Strategies%20of%20CXA-101%020and%20Taz%20in%020cUTI%020Patients.pdf.

Abstract for Ge et al., CXA-101 population PK analysis and Monte Carlo simulation for PK/PD target attainment and dose regimen selection. 49th Annual Interscience Conference on Antimicrobial Agents and Chemotherapy (ICAAC 2009); Sep. 12-15, 2009. Poster F1-2003.

Abstract for Ge et al., PK and safety of CXA-101, a new antipseudomonal cephalosporin, in healthy adult subjects after single intravenous dosing. 49th Annual Interscience Conference on Antimicrobial Agents and Chemotherapy (ICAAC 2009); Sep. 12-15, 2009. Poster F1-2004.

Abstract for Ge et al., PK study of CXA-101 in combination with tazobactam in dogs after intravenous administration. 49th Annual Interscience Conference on Antimicrobial Agents and Chemotherapy (ICAAC 2009); Sep. 12-15, 2009. Poster F1-2001.

Abstract for Giske et al., CXA-101 has high activity against clinical isolates of Pseudomonas aeruginosa including ceftazidime-resistant isolates. 49th Annual Interscience Conference on Antimicrobial Agents and Chemotherapy (ICAAC 2009); Sep. 12-15, 2009. Poster F1-1988.

Abstract for Hershberger et al. CXA-101/Tazobactam Probability of Target Attainment Using Population Pharmacokinetic Analysis. Joint Meeting of the European Congress of Clinical Microbiology and Infectious Diseases and International Congress of Chemotherapy (ECCMID-ICC 2011); May 7-12, 2011. Poster 1520; This poster is obtainable at: http://www.poster-submission.com/search/sresult.

Abstract for Jacqueline . Assessment of the In vivo Activity of CXA-101 in a Murine Model of Pseudomonas aeruginosa Pneumonia: Comparison with Ceftazidime and Piperacillin-Tazobactam. 50th Annual Interscience Conference on Antimicrobial Agents and Chemotherapy (ICAAC 2010); Sep. 12-15, 2010. Poster B-1401.

Abstract for Jacqueline et al. 50% effective dose determination of CXA-101 alone or in combination with tazobactam for treating experimental peritonitis in mice due to extended-spectrum beta-lactamase-producing *Escherichia coli* strains: comparison with ceftazidime and piperacillin/tazobactam. 49th Annual Interscience

(56) References Cited

OTHER PUBLICATIONS

Conference on Antimicrobial Agents and Chemotherapy (ICAAC 2009); Sep. 12-15, 2009. Poster F1-2000.
Abstract for Jacqueline et al. FIC Index determination of CXA-101/tazobactam in combination with amikacin, aztreonam, meropenem, levofloxacin, and tigecycline against *Escherichia coli*, Klebsiella pneumoniae, and Pseudomonas aeruginosa strains. 49th Annual Interscience Conference on Antimicrobial Agents and Chemotherapy (ICAAC 2009); Sep. 12-15, 2009. Poster F1-1995.
Abstract for Jacqueline et al. In vitro assessment using time-kill curves of CXA-101/tazobactam against *Escherichia coli*, Klebsiella pneumoniae, and Pseudomonas aeruginosa strains. 49th Annual Interscience Conference on Antimicrobial Agents and Chemotherapy (ICAAC 2009); Sep. 12-15, 2009. Poster F1-1996.
Abstract for Juan et al., Oliver A. Activity of the new cephalosporin CXA-101 against carbapenem-resistant Pseudomonas aeruginosa isolates from a Spanish multicenter study. 49th Annual Interscience Conference on Antimicrobial Agents and Chemotherapy (ICAAC 2009); Sep. 12-15, 2009. Poster F1-1987.
Abstract for Killian et al. An Equivalency Study of a Sensititre Dried MIC Plate Compared with the CLSI Broth Microdilution Reference Method for CXA-201 and Comparator Antimicrobials. 51st Annual Interscience Conference on Antimicrobial Agents and Chemotherapy (ICAAC 2011); Sep. 17-20, 2011. Poster D-691A.
Abstract for Livermore et al., Warner M. Activity of cephalosporin CXA-101 vs. P. aeruginosa. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-355; This poster is obtainable at: http://www.hpa.org.uk/webc/HPAwebFile/HPAweb_C/1225354148015.
Abstract for Marier et al. Pharmacokinetics of a novel antipseudomonal cephalosporin, CXA-101, and tazobactam in healthy adult subjects. 50th Annual Interscience Conference on Antimicrobial Agents and Chemotherapy (ICAAC 2010); Sep. 12-15, 2010. Poster A1-1391.
Abstract for Marier et al. Population PK Analysis of Intravenous CXA-101 in Subjects with Complicated Urinary Tract Infection, Including Pyelonephritis. 112th Annual Meeting of the American Society for Clinical Pharmacology and Therapeutics (ASCPT 2011); Mar. 2-5, 2011. Poster Pll-49.
Abstract for Hershberger et al. Pharmacokinetics of CXA-101/tazobactam in Subjects with Mild or Moderate Renal Impairment. Joint Meeting of the European Congress of Clinical Microbiology and Infectious Diseases and International Congress of Chemotherapy (ECCMID-ICC 2011); May 7-12, 2011. Poster 1519; This poster is obtainable at: http://www.poster-submission.com.
Abstract for Miller et al. Probability of Target Attainment of CXA-201 in Patients with Renal Hyperclearance. 49th Annual Meeting of the Infectious Diseases Society of America (IDSA 2011); Oct. 20-23, 2011. Poster B1-589.
Abstract for Miller et al., Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population. 52nd Annual Interscience Conference on Antimicrobia Agents and Chemotherapy (ICAAC 2012); Sep. 9-12, 2012. Poster A-641.
Abstract for Moulds et al., Impact of characterized resistance mechanisms on the susceptibility of Pseudomonas aeruginosa to CXA-101. 50th Annual Interscience Conference on Antimicrobial Agents and Chemotherapy (ICAAC Sep. 12-15, 2010. Poster C1-1415; This poster is obtainable at: http://www.cubist.com/downloads/Moulds. PP.ICAAC_2010.Impact_of resis_mech_on_suscep_of_P_aeruginosa_to_CXA_JNS.pdf.
Abstract for Moya et al. Affinity of the new cephalosporin CXA-101 to penicillin-binding proteins of Pseudomonas aeruginosa. 49th Annual Interscience Conference on Antimicrobial Agents and Chemotherapy (ICAAC 2009); Sep. 12-15, 2009. Poster F1-1985.
Abstract for Moya et al. Pan-Beta-lactam resistance development in P. aeruginosa clinical strains: molecular mechanisms, PBPs profiles and binding affinities. 51st Annual Interscience Conference on Antimicrobial Agents and Chemotherapy (ICAAC 2011); Sep. 17-20, 2011. Poster C1-619.
Abstract for Mushtaq et al. Activity of cephalosporin CXA-101 with B-lactamase inhibitors vs. Enterobacteriaceae. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-356; This poster is obtainable at: http://www.hpa.org.uk/webc/HPAwebFile/HPAweb_C/1225354148047.
Abstract for Riera et al. Activity of the new cephalosporin CXA-101 against biofilms of relevant P. aeruginosa phenotypes in cystic fibrosis chronic respiratory infection: mucoid and hypermutable strains. 49th Annual Interscience Conference on Antimicrobial Agents and Chemotherapy (ICAAC 2009); Sep. 12-15, 2009. Poster F1-1990.
Abstract for Sader et al., Activity of the Novel Antimicrobial Ceftolozane)Tazobactam Tested Against Bacterial Isolates in USA Hospitals from Patients with Pneumonia (2011). IDWeek 2012: A Joint Meeting of IDSA, SHEA, HIVMA, and PIDS; Oct. 17-21, 2012. Poster 846; This poster is obtainable at: http://www.jmilabs.com/data/posters/ IDWeek2012/846. Pdf.
Abstract for Sader et al., Activity of the Novel Antimicrobial Ceftolozane)Tazobactam Tested Against Contemporary Clinical Strains from USA Hospitals (2011). 52nd Annual Interscience Conference on Antimicrobial Agents and Chemotherapy (ICAAC 2012); Sep. 9-12, 2012. Poster E-199.
Abstract for Sader et al., Activity of the Novel Antimicrobial CXA-201 Tested Against Contemporary Clinical Strains from European Hospitals. 22nd Annual Meeting of the European Congress of Clinical Microbiology (ECCMID 2012); Mar. 31-Apr. 3, 2012. Poster P1446.
Abstract for Sader et al., Activity of the novel cephalosporin CXA-101 tested in combination with tazobactam against cephalosporin-resistant Enterobacteriaceae, P. aeruginosa and B. fragilis. 49th Annual Interscience Conference on Antimicrobial Agents and Chemotherapy (ICAAC 2009); Sep. 12-15, 2009. Poster F1-1992; This poster is obtainable at: http://www.jmilabs.com/data/posters/ICAAC2009/F1-1992.pdf.
Abstract for Snydman et al., Activity of Ceftolozane/Tazobactam CXA-201 against 270 recent isolates from the pacteroides group. 22nd Annual Meeting of the European Congress of Clinical Microbiology (ECCMID 2012); Mar. 31-Apr. 3, 2012. Poster; This poster is obtainable at: http://www.escmid_orgtescmid_library/online_lecture _library/?search=1&current_page=1&search_term=snydman.
Abstract for Soon et al., In vitro Pharmacodynamics of CXA-201 (Ceftolozane/Tazobactam) against Beta-lactamase producing *Eschericia coli*. 52nd Annual Interscience Conference on Antimicrobial Agents and Chemotherapy (ICAAC 2012); Sep. 9-12, 2012. Poster E-201.
Abstract for Titelman et al. Activity of CXA-101 plus tazobactam against ESBL-producing *E. coli* and K. pneumoniae. 49th Annual Interscience Conference on Antimicrobial Agents and Chemotherapy (ICAAC 2009); Sep. 12-15, 2009. Poster F1-1993.
Abstract for Umeh et al., A double-blind, randomized, phase 2 study to compare the safety and efficacy of intravenous CXA-101 and intravenous ceftazidime in complicated urinary tract infection. 50th Annual Interscience Conference on Agents and Chemotherapy (ICAAC 2010); Sep. 12-15, 2010. Poster L1-361A; This poster is obtainable at: http://www.cubist.com/downloads/Umeh_ICAAC2010_08144v2.pdf.
Abstract for Walkty et al. In Vitro Activity of Ceffolozane/Tazobactam (CXA-201) versus Pseudomonas aeruginosa Isolates Obtained from Patients in Canadian Hospitals: CANWARD 2011. IDWeek 2012: A Joint Meeting of IDSA, SHEA, HIVMA, and PIDS; Oct. 17-21, 2012. Poster 1616; This poster is obtainable at: https://idsa.confex. com/idsa/2012/webprogram/Handouttid509/POSTER202_1616.pdf.
Abstract for Zamorano et al. Activity of the new cephalosporin CXA-101 against P. aeruginosa isolates from chronically infected cystic fibrosis patients. 49th Annual Interscience Conference on Antimicrobial Agents and Chemotherapy (ICAAC 2009); Sep. 12-15, 2009. Poster F1-1991.

(56) References Cited

OTHER PUBLICATIONS

Abstract for Zhanel et al., In vitro Activity of Ceftolozane/tazobactam Tested Against 1,705 Gram-Negative Pathogens Isolated from Patients in Canadian Hospitals in 2011: CANWARD Surveillance Study. 52nd Annual Interscience Conference on Antimicrobial Agents and Chemotherapy (ICAAC 2012); Sep. 9-12, 2012. Poster E-200.
Abstract for Chandorkar et al. 'Population Pharmacokinetics (PPK) Meta-Analysis of Ceftolozane/Tazobactam in Healthy Volunteers and Patients'. Presented at the Annual Meeting of the American College of Clinical Pharmacy (ACCP 2013); Oct. 13-16, 2013; Albuquerque, NM. Poster# 120.
Abstract for Chandorkar et al. 'Pharmacokinetics and Safety of Ceftolozane/Tazobactam in Subjects with Severe Renal Impairment or End Stage Renal Disease on Hemodialysis'. To be presented at the 2nd Annual IDWeek (IDWeek 2013); Oct. 2-6, 2013; San Francisco, CA. Poster #723.
Abstract for Sader et al. 'Antimicrobial activity of ceftolozane/tazobactam and comparator agents tested against Pseudomonas aeruginosa isolates from United States (USA) medical centers (2011-2012)'. To be presented at the 2nd Annual IDWeek (IDWeek 2013); Oct. 2-6, 2013; San Francisco, CA. Poster #695.
Notice of Abandonment issued for U.S. Appl. No. 14/522,893. dated Aug. 27, 2015, 2 pages.
Notice of Abandonment issued for U.S. Appl. No. 14/213,997. dated Sep. 9, 2015, 2 pages.
Non Final Office Action issued for U.S. Appl. No. 14/212,590. dated Jun. 8, 2015, 9 pages.
Arin et al, 'The Comparative Stability of Different Types of Penicillin and Cephalosporin N-pyrryl derivatives'. Pharmazie 1988, vol. 43, pp. 18-19.
Cefazolin, (For Injection USP) Approved Dec. 1988, Product Label, B. Braun Medical Inc. Revised Jan. 2012.
Ceftazidime, (Systemic) Approved Nov. 1985, Product Label. American Society of Health-System Pharmacists Inc. 2004.
Claforan, (Sterile—Cefotaxime for injection, USP & Injection—Cefotaxime injection) Approved Prior to Jan. 1982, Product Label. Sanofi-Aventis U.S. LLC 2011.
Cubist Pharmaceuticals, 'Cubist Announces Positive Results from Two Phase 2 Trials, CXA-201 and CDAD Program'. Cubist Press Release. Jun. 2011.
Doribax, Approved Oct. 2007, Product Label. Ortho-McNeil-Janssen Pharmaceuticals, Inc. 2007.
Fortaz, (ceftazidime for Injection) (Ceftazidime Injection) Approved Jul. 1985, Product Label. GlaxoSmithKline 2007.
Maxipime, (Cefepime Hydrochloride, USP) Approved Jan. 1996, Product Label. Bristol-Myers Squibb Company, Revised Mar. 2009.
Yamana et al, 'Comparative Stability of Cephalosporins in Aqueous Solution: Kinetics and Mechanisms of Degradation'. Journal of Pharmaceutical Sciences 1976, vol. 65, No. 11, pp. 1563-1574.
Rocephin, (Ceftriaxone Sodium) Approved Aug. 1993, Product Label. Roche Laboratories, Copyright 1998.
Zithromax, (azithromycin injection) Approved Sep. 1994, Product Label. Pfizer Labs, Revised Feb. 2013.
Teflaro, (Ceftaroline fosamil) Approved Oct. 2010, Product Label. Forst Laboratories, Inc. 2010.
European Committee on Antimicrobial Sus Testing 2012.
Giske et al, 'Activity of Cephalosporin CXA-101 and Comparators against Extended-spectrum-beta-lactamase—producing Pseudomonas aeruginosa'. Journal of Antimicrobial Chemotherapy 2009, vol. 64, No. 2, pp. 430-431.
Jacqueline et al, 'Efficacy of Ceftolozane in a Murine Model of Pseudomonas aeruginosa acute pneumonia: in vivo Antimicrobial Activity and Impact on Host Inflammatory Response'. Journal of Antimicrobial Chemotherapy 2012, vol. 58, No. 1, pp. 1-7.
Livermore et al, 'Activity of Cephalosporin CXA-101 against Pseudomonas aeruginosa and Burkholderia cepacia strains and Isolates'. International Journal of Antimicrobial Agents 2009, vol. 34, No. 5, pp. 402-406.

Takeda et al, 'Stability of FR264205 against AmpC beta-lactamase of Pseudomonas aeruginoas'. International Journal Antimicrobial Agents, 2007. vol. 30, No. 5, pp. 443-445.
Takeda et al., In vitro and in vivo activities of a new cephalosporin, FR264205, against Pseudomonas aeruginosa. Antimicrob Agents Chemother. 2007; 51(3):826-30.
Titelman et al, 'In vitro Activity of CXA-101 Plus Tazobactum against CTX-M-14 and CTX-M-15-producing *Escherichia* and *Klebsiella pneumoniae*'. Diagnostic Microbiology and Infectious Disease. 2011, vol. 70, No. 1, pp. 137-141.
Toda et al, 'Synthesis and SAR of Novel Parenteral Antipseudomonal cephalosporins: Discovering of FR264205. Med Chem Lett. 2008, vol. 18, No. 17, pp. 4849-4852.
Anderegg et al: Quality Control Guidelines for BAL9141 (Ro 63/9141), an Investigational Cephalosporin, When Reference MIC and Standardized Disk Diffusion Susceptibility Test Methods Are Used; Journal of Clinical Microbiology. (2004), pp. 3356-3358.
Farrell: Antimicrobial Activity of Ceftolozane-Tazobactam Tested against Enterobacteriaceae with Various Resistance Patterns Isolated in U.S. Hospitals; Antimicrobial Agents and Chemotherapy; (2013) vol. 57 No. 12 pp. 6305-6310.
International Preliminary Report on Patentability for for PCT/US2012/054191, dated Mar. 12, 2014, 8 pages.
International Search Report for PCT/US2012/054191, dated Feb. 20, 2013, 4 pages.
Marunaka: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H), in Aqueous Solutions and Alkaline MEthanol Solution: Pathway and Structural Elucidation of Products; Chem. Pharm. Bull.; 1988, vol. 36, pp. 4478-4487.
Matsushima: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H) in Solid State: Structural Eldcidation; Chem. Pharm. Bull.; 1988, vol. 36, pp. 4593-4596.
Murano: Structural requirements for the stability of novel cephalosporins to AmpC beta-lactamase based on 3-D structure; Bioorg. Med, Chem. Lett.; 2007, vol. 16, pp. 2261-2275.
Search Request Confirmation; Science IP; Dec. 6, 2010, 3 pages.
Sutcliffe et al: Multidrug-Resistant Gram-Negative Pathogens: New Strategies; Tetraphase Pharmaceuticals . Retrieved online from: http://www.tuffs.edu/med/apua/practitioners/resources_23_2817980013.pdf Retrieved Mar. 19, 2014.
U.S. National Institutes of Health, 'Safety and Efficacy Study of Ceftolozane/Tazobactam to Treat Ventilated Nosocomial Pneumonia (ASPECT-NP)'. Sponsored by Cubist Pharmaceuticals. http://www.clinicaltrials.gov/ct2/show/NCT02070757?term=ceftolozane&rank=1 Updated Feb. 21, 2014. ClinicalTrials.gov Identifier: NCT02070757 (Study not yet open for participant recruitment).
U.S. National Institutes of Health, 'Safety and Efficacy Study of IV CXA-101 and IV Ceftazidime in Patients with Complicated Urinary Tract Infections'. Sponsored by Cubist Pharmaceuticals. http://www.clinicaltrials.gov/ct2/show/NCT00921024?term=ceftolozane&rank=4 Updated Aug. 5, 2010. ClinicalTrials.gov Identifier: NCT00921024 (Study has been completed).
U.S. National Institutes of Health, 'Safety and Efficacy Study to Compare IV CXA 101/Tazobactam and Metronidazole With Meropenem in Complicated Intraabdominal Infections'. Sponsored by Cubist Pharmaceuticals. http://www.clinicaltrials.gov/ct2/show/NCT01147640?term=ceftolozane&rank=2 Updated May 5, 2011. ClinicalTrials.gov Identifier: NCT01147640 (Study has been completed).
U.S. National Institutes of Health, 'Study of Intravenous Ceftolozane/Tazobactam vs. Piperacillin/Tazobactam in Ventilator Associated Pneumonia'. Sponsored by Cubist Pharmaceuticals. http://www.clinicaltrials.gov/ct2/show/NCT01853982?term=ceftolozane&rank=3 Updated Jan. 28, 2014. ClinicalTrials.gov Identifier: NCT01853982 (Study has been terminated).
Wootton et al: BAL 9141, a new borad-spectrum pyrrolidinone cephalosporin: activity against clinically significant anaerobes in comparison with 10 other antimicrobials; Journal of Antimicrobial Chemotherapy; (2002) vol. 49, pp. 535-539.

(56) References Cited

OTHER PUBLICATIONS

Written Opinion of the International Searching Authority for PCT/US2012/054191, dated Feb. 20, 2013, 7 pages.
Yoshizawa: New broad-spectrun parenteral cephalosporins exhibiting potent activity against both methicilln-resistant *Staphlococcus aureus* (MRSA) and Pseudomonas aeruginosa. Part 3: &Beta-[2-(5-Amino-1,2,4-thiadiazol-3-yl)-2-ethoxtiminoacetamido] cephalosporins bearing 4-[3-(aminoalkyl)-ureido]-1-pyridinium at C3; Bioorg. Med. Chem. Lett.; 2004, vol. 12, pp. 4221-4231.
Brown, R.F. et al. 'Synthesis and Biological Evaluation of a Series of Parental 3'-Quaternary Ammonium Cephalosporins.sup.1' Journal of Medicinal Chemistry. 1990, vol. 33, No. 8, pp. 2114-2121.
Sakagami, K. et al. 'Synthetic Cephalosporins. VI..sup.1) Synthesis and Antibacterial Activity of 7-[(Z)-2-(2-Aminothiazol-4-YL)-2-(1-Carboxy-1-Methyl)Ethoxyiminoacetamido- ]-3-(3-Hydroxy-4-Pyridon-1-YL)Methyl-3-Cephem-4-Carboxylic Acid and Related Compounds'. Chemical and Pharmaceutical Bulletin. 1990, vol. 38, No. 8, pp. 2271-2273.
English Translation of Abstract for Japanese Patent No. JP 04-288286, published Oct. 13, 1992, 3 pages.
Clinical and Laboratory Standards Institute CLSI Document M07-A9; Jan. 2012, vol. 32, No. 2 (88 pages).
Clinical and Laboratory Standards Institute CLSI Document M100-S22; Jan. 2012, vol. 32, No. 3 (188 pages).
Extended European Search Report for Application No. 14160151.8, dated May 13, 2014, 9 pages.
Notification of Transmittal of the International Search Report and the Written Opinion of the International Searching Authority for International Application No. PCT/US2014/028642, dated Aug. 7, 2014, 14 pages.
Cubist Pharmaceuticals (Business Wire. Cubist Pharmaceuticals Announces Approval of Second Bulk Drug Manufacturing Facility. 2005).
FDA CGMP Guidance (Guidance for Industry: Non-Penicillin Beta-Lactam Drugs: A CGMP Framework for preventing Cross Contamination. FDA. Apr. 1-10, 2013).
FDA Compliance Policy Guides, "CPG Sec 430.100 Unit Dose Labeling for Solid and Liquid Oral Dosage Forms," Jun. 7, 2011. Online [http://web.archive.org/web/2011 0607033315 /http://www.fda.gov/ICECl/ ComplianceManuals/CompliancePolicyGuidanceManual/ucm074377.htm].
Cabot et al. 'Pseudomonas aeruginosa Ceftolozane-Tazobactam Resistance Development Requires Multiple Mutations Leading to Overexpression and Structural Modification of AmpC'. Antimicrob Agents Chemother. Mar. 17, 2014. [Epub ahead of print] PubMed PMID: 24637685.
Craig et al. 'In-Vivo Activity of Ceftolozane, a New Cephalosporin, with and without Tazobactam against Pseudomonas aeruginosa and Enterobacteriaceae, including Strains with Extended-Spectrum B-Lactamases, in the Thighs of Neutropenic Mice'. Antimicrob Agents Chemother. 2013 vol. 57, No. 4, pp. 1577-1582.
Ge et al. 'Pharmacokinetics and safety of CXA-1 01, a new antipseudomonal cephalosporin, in healthy adult male and female subjects receiving single- and multiple-dose intravenous infusions'. Antimicrob Agents Chemother. 2010 vol. 54, No. 8, pp. 3427-3431.
Hayakawa et al. 'Epidemiology and Risk Factors for Isolation of *Escherichia coli* Producing CTX-M-Type Extended-Spectrum B-Lactamase in a Large U.S. Medical Center'. Antimicrob Agents Chemother. 2013 vol. 57, No. 8, pp. 4010-4018.
Hong et al. 'Ceftolozane/tazobactam: a novel antipseudomonal cephalosporin and B-lactamase-inhibitor combination'. Infect Drug Resist. 2013 vol. 29, No. 6, pp. 215-223.
Jacqueline et al. 'Efficacy of ceftolozane in a murine model of Pseudomonas aeruginosa acute pneumonia: in vivo antimicrobial activity and impact on host inftammatory response'. J Antimicrob Chemother. 2013 vol. 63, No. 1, pp. 177-183.
Juan et al. 'Activity of a new antipseudomonal cephalosporin, CXA-1 01, against carbapenem-resistant and multidrug-resistant Pseudomonas aeruginosa clinical strains'. Antimicrob Agents Chemother. 2010, vol. 54, No. 2, pp. 846-851.

Miller et al. 'CXA-201 dose selection based on probability of target attainment and drug exposure in subjects with varying degrees of renal impairment'. 51st Annual Interscience Conference on Antimicrobial Agents and Chemotherapy (ICAAC 2011 ); Sep. 17-20, 2011; Chicago, IL. Oral Presentation A-1 099.
Nicasio et al. 'PK-PD ofTazobactam (TAZ) in Combination with Piperacillin (PIP) in an In Vitro Infection Model (IVIM)'. 53rd Annual Interscience Conference on Antimicrobial Agents and Chemotherapy (ICAAC 2013); Sep. 10-13, 2013; Denver, CO. Oral Presentation.
Sader et al. 'Post-B-Lactamase-Inhibitor Effect of Tazobactam in Combination with Ceftolozane on Extended-Spectrum-B-Lactamase-Producing Strains'. Antimicrob Agents Chemother. 2014 vol. 58 No. 4, pp. 2434-243.
Sader et al. 'Antimicrobial Activity of Ceftolozane!Tazobactam Tested Against Gram-Negative Bacterial Isolates from Hospitalized Patients with Pneumonia in European Hospitals (2011 )'. 23rd Annual Meeting of the European Congress of Clinical Microbiology (ECCMID 2013); Apr. 27-30, 2013; Berlin, Germany. Oral Presentation O-181.
Shanley, Agnes. (2013) Pharmaceutical Manufacturing. Facilities of the Future. <http://www.phrmamanufacturing.com/articles/2013/011 />.
Snydman et al. 'Activity of Ceftolozane/Tazobactam Against a Broad Spectrum of Recent Clinical Anaerobic Isolates'. Antimicrob Agents Chemother. 2014 vol. 58, No. 2, pp. 1218-1223.
Titelman et al. 'In vitro activity of CXA-101 plus tazobactam against CTX-M-14- and CTX-M-15-producing *Escherichia coli* and Klebsiella pneumoniae'. Diagn MicrobiolInfect Dis. 2011 vol. 70, No. 1, pp. 137-141.
Toda et al. 'FR264205, A Novel Parenteral Antipseudomonal Cephem: Synthesis and SAR of 3-(2,4-Disubstituted 3-Aminopyrazolio)methyl Cephalosporins'. 46th AnnualInterscience Conference on Antimicrobial Agents and Chemotherapy (ICAAC 2006); Sep. 27-30, 2006; San Francisco, CA. Oral Presentation F1-0240.
Vanscoy et al. 'Pharmacological basis of B-lactamase inhibitor therapeutics: tazobactam in combination with Ceftolozane'. Antimicrob Agents Chemother. 2013. vol. 57 No. 12, pp. 5924-5930.
Vanscoy et al. 'Relationship between Ceftolozane!Tazobactam Exposure and Drug-Resistance Amplification in a Hollow-Fiber Infection Model'. Antimicrob Agents Chemother. Jun. 17, 2013. vol. 57 No. 9, pp. 4134-4138.
Walkty et al. 'In vitro activity of ceftolozane-tazobactam against Pseudomonas aeruginosa isolates obtained from patients in Canadian hospitals in the CANWARD study, 2007 to 2012'. Antimicrob Agents Chemother. 2013, vol. 57, No. 11, pp. 5707-5709.
Wooley et al. 'Impact of renal function on the pharmacokinetics and safety of ceftolozane-tazobactam'. Antimicrob Agents Chemother. 2014 vol. 58, No. 4, pp. 2249-2255.
Zhanel et al. 'Ceftolozane/Tazobactam: A Novel Cephalosporin/B-Lactamase Inhibitor Combination with Activity Against Multidrug-Resistant Gram-Negative Bacilli'. Drugs. 2014 vol. 74 No. 1, pp. 31-51.
Zilberberg et al. 'Prevalence of multidrug-resistant Pseudomonas aeruginosa and carbapenem-resistant Enterobacteriaceae among specimens from hospitalized patients with pneumonia and bloodstream infections in the United States from 2000 to 2009'. J Hasp Med. 2013 vol. 8, No. 10, pp. 559-563.
Zilberberg et al. 'Secular Trends in Gram-Negative Resistance among Urinary Tract Infection Hospitalizations in the United States, 2000-2009'. Infect Control Hasp Epidemiol. 2013, vol. 34, No. 9, pp. 940-946.
Bulik et al, In vivo comparison of CXA-101 with and without tazobactam versus piperacillin-tazobactam using human simulated exposures against phenotypicaliy diverse gram-negative organisms. Antirnicrob Agent Chemother 2012 56 (1):544-9.
Bulik et al., In vitro potency of CXA-101, a novel cephalosporin, against Pseudomonas aeruginosa displaying various resistance phenotypes, including multidrug resistance. Antimicrob Agents Chemother. 2010;54(1):557-9.
Chandorkar et al., Intrapulmonary penetration of ceftolozaneltazobactam and piperacillin/tazobactam in healthy adult subjects. J Antimicrob Chemother. 2012, 67, 2463.

(56) References Cited

OTHER PUBLICATIONS

Clinical and Laboratory Standards Institute CLSI Document M07-A9.
Clinical and Laboratory Standards Institute CLSI Document M100-S22.
Ge et al., Pharmacokinetics and safety of CXA-101, a new antipseudomonal cephalosporin, in healthy adult male and female subjects receiving single- and multiple-dose intravenous infusions. Antimicrob Agents Chemother. 2010 , 54: 3427-31
Juan et al., Activity of a new antipseudomonal cephalosporin, CXA-101, against carbapenem-resistant and multidrug-resistant Pseudomonas aeruginosa clinical strains, Antimicrob Agents Chemother, 2010;54(2):846-51.
Livermore et al., Chequerboard titration of cephalosporin CXA-101 and tazobactam versus beta-lactamase-producing Enterobacteriaceae. J Antimicrob Chemother. 2010 65 1972-4.
Miller et al,, Pharmacokinetics and Safety of Intravenous Ceftolozane/tazobactam in Healthy Adult Subjects following Single and Multiple Ascending Doses. Antimicrob Agents Chemother. 2012 56:3086-91.
Moya et al.; Activity of a new cephalosporin, CXA-101 (FR264205), against beta-lactam-resistant Pseudomonas aeruginosa mutants selected in vitro and after antipseudomonal treatment of intensive care unit patients. Antimicrob Agents Chemother. 2010 ;54(3):1213-7.
Moya et al., Affinity of the New Cephalosporin CXA-101 to Penicillin-Binding Proteins of Pseudomonas aeruginosa. Antimicrob Agents Chemother, 2010; 54: 3933-3937.
Moya et al., Pan-Beta-Lactam Resistance Development in Pseudomonas aeruginosa Clinical Strains: Molecular Mechanisms, Penicillin-Binding Protein Profiles, and Binding Affinities. Antimicrob Agents Chemother. 2012 56 4771-8.
Perletti et al., CXA-101—Cephalosporin Antibiotic, Drugs of the Future 2010; 35(12): 977-986.
Riera et al., Anti-biofilm and resistance suppression activities of CXA-101 against chronic respiratory infection phenotypes of Pseudomonas aeruginosa strain PAO1. J Antimicrob Chemother. 2010;65(7):1399-1404.
Sader et al., Antimicrobial activity of CXA-101, a novel cephalosporin tested in combination with tazobactam against Enterobacteriaceae, Pseudomonas aeruginosa, and Bacteroides fragilis strains having various resistance phenotypes. Agents Chemother. 2011 55(5):2390-4.
Zamorano et al., Activity of the new cephalosporin CXA-101 against Pseudomonas aeruginosa isolates from chronically-infected cystic fibrosis patients. Clin Microbiol Infect. 2010 16(9):1482-7.
U.S. Appl. No. 14/285,185, filed Apr. 11, 2014. 77 pages.
Miller et al. 'Pharmacokinetics and Safety of Intravenous Ceftolozane-Tazobactum in Healthy Adult Subjects following Single and Multiple Ascending Doses'. Antimicrobial Agents and Chemotherapy. 2012. vol. 56, No. 6, pp. 3086-3091.
Office Action issued for U.S. Appl. No. 14/285,185. dated Jul. 25, 2014. 10 pages.
U.S. Appl. No. 14/250,879, filed May 22, 2014, 74 pages.
Office Action issued for U.S. Appl. No. 14/250,879. dated Jul. 8, 2014. 40 pages.
Lehr et al. 'Particulate Matter Contamination of Intravenous Antibiotics Aggravates Loss of Functional Capillary Density in Postischemic Striated Muscle'. Am. J. Respir. Crit. Care Med. 2002, vol. 165, pp. 514-520.
Non-Final Office Action for U.S. Appl. No. 14/214,324, dated Jul. 7, 2014. (16 Pages).
Abstract for Sader et al. 'Antimicrobial Activity of Ceftolozane!Tazobactam Tested Against Gram-negative Bacterial Isolates from Hospitalized Patients with Pneumonia in United States (USA) and European (EU) Hospitals (2012)'. 53rd AnnualInterscience Conference on Antimicrobial Agents and Chemotherapy (ICAAC 2013); Sep. 10-13, 2013; Denver, CO. Poster C2-1633.
Abstract for Sader et al. 'Post Beta-Lactamase Inhibitor Effect of Tazobactam When Associated with Ceftolozane and Tested against ESBL—Producing Strains'. 53rd Annual Interscience Conference on Antimicrobial Agents and Chemotherapy (ICAAC 2013); Sep. 10-13, 2013; Denver, CO. Poster A-1030.
Abstract for Vanscoy et al. 'Relationship between Ceftolozane!Tazobactam (TOL!TAZ) Exposure and E. coli Resistance Amplification Prevention in a Hollow Fiber Infection Model (HFIM)'. 53rd Annual Interscience Conference on Antimicrobial Agents and Chemotherapy (ICAAC 2013); Sep. 10-13, 2013; Denver, CO. Poster A-1031.
Abstract for Vanscoy et al. 'Identification of a Translational Relationship Between Tazobactam (TAZ) Exposure in combination with Ceftolozane (TOL) and Efficacy Against ESBL-Producing Enterobacteriaceae'. 53rd Annual Interscience Conference on Antimicrobial Agents and Chemotherapy (ICAAC 2013); Sep. 10-13, 2013; Denver, CO. Poster A-1032.
Abstract for Zhanel et al. 'In Vitro Activity of Ceftolozane!Tazobactam Against 5,715 Gram-Negative and Gram-Positive Pathogens Isolated from Patients in Canadian Hospitals in 2011 and 2012: CANWARD Surveillance Study'. 53rd Annual Interscience Conference on Antimicrobial Agents and Chemotherapy (ICAAC 2013); Sep. 10-13, 2013; Denver, CO. Poster E-1689.
Abstract for Zilberberg et al. 'Multidrug resistant Pseudomonas aeruginosa among hospitalized patients with pneumonia, US 2000-2009'. Making a Difference in Infectious Diseases Pharmacotherapy Conference (MAD-ID 2013); May 9-11, 2013; Orlando, FL. Encore Presentation from ISICEM 2013.
Abstract for Zilberberg et al. 'Gram-negative resistance and need for ICU among urinary tract infections in the US'. Making a Difference in Infectious Diseases Pharmacotherapy Conference (MAD-ID 2013); May 9-11, 2013; Orlando, FL. Encore Presentation from ISICEM 2013.
Abstract for Zilberberg et al.'Multidrug resistance among P. aeruginosa and Enterobacteriaceae in the US hospitals, 2000-2009'. Making a Difference in Infectious Diseases Pharmacotherapy Conference (MAD-ID 2013); May 3-11, 2013; Orlando, FL. Encore Presentation from SCCM 2013.
Abstract for Chandorkar et al. Target Attainment Rates (TAR) and Cumulative Fraction of Response (CFR) in Plasma for Ceftolozane in a Simulated Population of Patients with Complicated Intra-abdominal (ciAI) and Urinary Tract Infection (cUTl)'. 23rd Annual Meeting of the European Congress of Clinical Microbiology (ECCMID 2013); Apr. 27-30, 2013; Berlin, Germany.
Abstract for Halimi et al. 'Comparative Evaluation of Ceftolozane/tazobactam MIG testing with Etest® and CLSI Broth Microdilution Methods'. 23rd Annual Meeting of the European Congress of Clinical Microbiology (ECCMID 2013); Apr. 27-30, 2013; Berlin, Germany. Poster P1606.
Abstract for Reynolds et al. 'Pseudomonas aeruginosa in the UK and Ireland: Susceptibility to Old and New Agents'. 23rd Annual Meeting of the European Congress of Clinical Microbiology (ECCMID 2013); Apr. 27-30, 2013; Berlin, Germany. Poster P1519.
Abstract for Sader et al. 'Antimicrobial activity of ceftolozane/tazobactam and comparator agents tested against Pseudomonas aeruginosa strains from 14 European countries and Israel'. 23rd Annual Meeting of the European Congress of Clinical Microbiology (ECCMID 2013); Apr. 27-30, 2013; Berlin, Germany. Poster P1630.
Abstract for Noel et al. 'Pharmacodynamics of Ceftolozane/Tazobactam Against Gram Negative Bacilli'. 53rd Annual Interscience Conference on Antimicrobial Agents and Chemotherapy (ICAAC 2013); Sep. 10-13, 2013; Denver, CO. Poster A-1029.
Abstract for Melchers et al. 'Pharmacokinetics of Tazobactam and Ceftolozane Alone and in Combination in Mice'. 53rd Annual Interscience Conference on Antimicrobial Agents and Chemotherapy (ICAAC 2013); Sep. 10-13, 2013; Denver, CO. Poster A-1033.
Abstract for Melchers et al. 'Pharmacodynamics of Ceftolozane Combined with Tazobactam in a Neutropenic Mouse Thigh Model'. 53rd AnnualInterscience Conference on Antimicrobial Agents and Chemotherapy (ICAAC 2013); Sep. 10-13, 2013; Denver, CO. Poster A-1034.
Abstract for Lucasti et al. 'A Multicenter, Double-Blind, Randomized, Phase 2 Study to Assess the Safety and Efficacy of Ceftolozane/Tazobactam (TOLITAZ) plus Metronidazole (MTZ) Compared to Meropenem (MER) in Adult Patients with Complicated Intra-

(56) References Cited

OTHER PUBLICATIONS abdominal Infections (clAl)'. 53rd AnnualInterscience Conference on Antimicrobial Agents and Chemotherapy (ICAAC 2013); Sep. 10-13, 2013; Denver, CO. Poster K-1709.
Abstract for Estabrook et al. 'In vitro Activity of CXA-201 (Ceftolozane-Tazobactam) Against 200 CTX M-Producing *Escherichia coli* Clinical Isolates'. 53rd Annual Interscience Conference on Antimicrobial Agents and Chemotherapy (ICAAC 2013); Sep. 10-13, 2013; Denver, CO. Poster E-1169.
Abstract for Bulik et al. 'In vitro activity of CXA-101, a novel cephalosporin, against resistant phenotypes of Pseudomonas aeruginosa'. 47th Annual Meeting of the Infectious Diseases Society (IDSA 2009); Oct. 29-Nov. 1, 2009; Philadelphia, PA. Poster 209.
Abstract for Moya et al. 'Activity of CXA-101 against Pseudomonas aeruginosa beta-lactam resistance mechanisms: ampD, ampDh2, ampDh2, dacB, and oprD mutations'. 49th Annual Interscience Conference on Antimicrobial Agents and Chemotherapy (ICAAC 2009); Sep. 12-15, 2009; San Francisco, CA. Poster F1-1989.
Abstract for Livermore et al. 'Chequerboard titrations of cephalosporin CXA-101 and tazobactam vs. beta-lactamase producing Enterobacteriaceae'. 49th AnnualInterscience Conference on Antimicrobial Agents and Chemotherapy (ICAAC 2009); Sep. 12-15, 2009; San Francisco, CA. Poster F1-1994.
Abstract for Jacqueline et al. 'ED50 Determination of CXA-101 Alone and in Combination with Tazobactam for Treating Experimental Peritonitis in Mice Due to ESBL-Producing Klebsiella pneumoniae strains: Comparison with Ceftazidime and Piperacillin/ Tazobactam'. 50th AnnualInterscience Conference on Antimicrobial Agents and Chemotherapy (ICAAC 2010); Sep. 12-15, 2010; Boston, MA. Poster B-708.
Abstract for Cabot et al. 'Pseudomonas aeruginosa Ceftolozane/ Tazobactam Resistance Development Requires Multiple Mutations Leading to Overexpression and Structural Modification of AmpC'. 53rd Annual Interscience Conference on Antimicrobial Agents and Chemotherapy (ICAAC 2013); Sep. 10-13, 2013; Denver, CO. Poster C1-060.
Abstract for Jacqueline. 'In vivo Activity of CXA-101 against Pseudomonas aeruginosa in a Rabbit Experimental Pneumonia: Comparison with Ceftazidime Piperacillin-Tazobactam and Imipenem'. 51st AnnualInterscience Conference on Antimicrobial Agents and Chemotherapy (ICAAC 2011 ); Sep. 17-20, 2011; Chicago, IL. Poster B-590.
Abstract for Reynolds et al. 'Enterobacteriaceae in the UK and Ireland: Susceptibility to Old and New Agents'. 52nd AnnualInterscience Conference on Antimicrobial Agents and Chemotherapy (ICAAC 2012); Sep. 9 12, 2012; San Francisco, CA. Poster C2-152.
Abstract for Miller et al. 'Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population'. 52nd Annual Interscience Conference on Antimicrobial Agents and Chemotherapy (ICAAC 2012); Sep. 9-12, 2012; San Francisco, CA. Poster A-641.
Abstract for Melchers et al. 'In vitro Activity of CXA-101 Alone and in Combination With Tazobactam Against Extended Spectrum Beta-lactamase Harbouring Enterobacteriaceae'. 52nd AnnualInterscience Conference on Antimicrobial Agents and Chemotherapy (ICAAC 2012); Sep. 9-12, 2012; San Francisco, CA. Poster E 198.
Abstract for Zilberberg et al. 'Prevalence of beta-lactam resistance among P. aeruginosa in US hospitals, 2000-2009'. To be presented at the 2nd AnnuaiiDWeek (IDWeek 2013); Oct. 2-6, 2013; San Francisco, CA. Poster #1580.
Abstract for Cabot et al. 'Dynamics and mechanisms of resistance development to ceftazidime, meropenem and ceftolozane-/ tazobactam in wild-type and mutator P. aeruginosa strains'. 52nd Annual Interscience Conference on Antimicrobial Agents and Chemotherapy (ICAAC 2012); Sep. 9-12, 2012; San Francisco, CA. Poster C1-1970.
Abstract for Sader et al. 'Frequency of occurrence and antimicrobial susceptibility of Gram-negative organisms isolated from health care associated urinary tract infections: Results from the Program to Assess Ceftolozane/Tazobactam Susceptibility (PACTS)'. To be presented at the 2nd Annual IDWeek (IDWeek 2013); Oct. 2-6, 2013; San Francisco, CA. Poster 699.
Abstract for Zilberberg et al. 'Secular trends in gram-negative resistance among urinary tract infection hospitalizations in the US, 2000-2009'. 23rd Annual Meeting of the European Congress of Clinical Microbiology (ECCMID 2013); Apr. 27-30, 2013; Berlin, Germany. Poster P1517.
Abstract for Vanscoy et al. 'Pharmacokinetics-Pharmacodynamics (PK-PD) of Tazobactam in Combination with Ceftolozane in an In Vitro Infection Model'. 23rd Annual Meeting of the European Congress of Clinical Microbiology (ECCMID 2013); Apr. 27-30, 2013; Berlin, Germany. Poster P900.
Abstract for Sader et al. 'Ceftolozane/tazobactam activity tested against aerobic Gram-negative organisms isolated from intraabdominal infections in European and United States hospitals (2012)'. To be presented at the 2nd Annual IDWeek (IDWeek 2013); Oct. 2-6, 2013; San Francisco, CA. Poster #698.
Abstract for Sader et al. 'Antimicrobial susceptibility of gram-negative bacteria causing urinary tract infections in European and United States hospitals (2009-2011)'. 23rd Annual Meeting of the European Congress of Clinical Microbiology (ECCMID 2013); Apr. 27-30, 2013; Berlin, Germany. Poster P1516.
Alexov et al. Efficacy of Ampicillin-Sulbactam Is not Dependent upon Maintenance of a Critical Ratio between Components: Sulbactam Pharmacokinetics in Pharmacodynamic Interactions. Antimcirobial Agents Chemotherapy 1996;40:2468.
Bush et al. Kinetic Interactions of Tazobactam with Beta-Lactamases from All Major Structural Classes. Antimicrobial Agents and Chemotherapy 1993;37:851.
Hatano et al. In vivo Anti-Pseudomonas Aeruginosa Activity of Novel Parenteral Cephalosporin, FR264205. 45th Annual Interscience Conference on Antimicrobial Agents and Chemotherapy (ICAAC 2005); Dec. 16-19, 2005. Oral Presentation F-1165.
Kurpiel. Point Mutations in the Inc Antisense RNA Gene Are Associated with Increased Plasmid Copy Number, Expression of BlaCMY-2 and Resistance to Piperacillin/Tazobactam in *Escherichia coli*. Journal of Antimicrobial Chemotherapy 2012;67:339.
Lister et al. Importance of Beta-Lactamase Inhibitor Pharmacokinetics in the Pharmacodynamics of Inhibitor-Drug Combinations: Studies with Piperacillin-Tazobactam and Piperacillin-sulbactam. Antimicrobial Agents and Chemotherapy 1997;41:721.
Louie et al., Pharmacodynamics of b-Lactamase Inhibition by NXL104 in Combination with Cefaroline: Examining Organisms with Multiple Types of b-Lacramases. Antimicrobial Agents and Chemotherapy. 2012, 56, 258.
Miller et al. CXA-201 dose selection based on probability of target attainment and drug exposure in subjects with varying degrees of renal impairment ICAAC 2011. Oral Presentation A-1099.
Seetulsingh et al. Activity of Clavulanate Combinations against TEM-1 b-Lactamase-Producing *Escherichia coli* Isolates Obtained in 1982 and 1989. Journal of Antimicrobial Chemotherapy 1991;27:749.
Soon et al. A Novel Mathematical Modeling Approach to Characterize the Pharmacodynamics of Ceftolozane/Tazobactam, a β-lactam & β-lactannase Inhibitor Combination. 52nd Annual Interscience Conference on Antimicrobial and Chemotherapy (ICAAC 2012); Sep. 9-12, 2012. Oral Presentation A-1762.
Steenbergen et al. Potency of CXA-101Tazobactam for Pathogens from ICU and non-ICU Correlated to Probability of Pharmacokinetic/ Pharmacodynamic (PK/PD) Target Attainment. ICAAC 2011. Oral Presentation A-1689.
Strayer et al. Pharmacodynamics of Piperacillin Alone and in Combination with Tazobactam against Piperacillin-Resistant and -Susceptible Organisms in an In Vitro Model of Infection. Antimicrobial Agents and Chemotherapy 1994;38:2351.
Thomson et al. Beta-Lactamase Production in Memebers of the Family Enterobacteriaceae and Resistance to Beta-Lactam-Enzyme Inhibitor Combinations. Antimicrobial Agents and Chemotherapy 1990;34:622.

(56) References Cited

OTHER PUBLICATIONS

FDA CGMP Guidance (Guidance for Industry: Non-Penicillin Beta-Lactam Drugs: A CGMP Framework for preventing Cross Contamination. FDA. Apr. 2013.1-10).

FDA Compliance Policy Guides, "CPG Sec 430.100 Unit Dose Labeling for Solid and Liquid Oral Dosage Forms," Jun. 7, 2011. Online [http://web.archive.org/web/2011 0607033315 /http://www.fda.gov/ICECI/ ComplianceManuals/CompliancePolicyGuidanceManual/ucm074377.htm].

Niicasio et al. 'PK-PD of Tazobactam (TAZ) in Combination with Piperacillin (PIP) in an In Vitro Infection Model (IVIM)'. 53rd Annual Interscience Conference on Antimicrobial Agents and Chemotherapy (ICAAC 2013); Sep. 10-13, 2013; Denver, CO. Oral Presentation.

Vanscoy et al. 'Pharmacological basis of B-lactamase inhibitor therapeutics: tazobactam in combination with aeftolozane'. Antimicrob Agents Chemother. 2013. vol. 57 No. 12, pp. 5924-5930.

Vanscoy et al. 'Pharmacokinetics-Pharmacodynamics of Tazobactam in Combination with Ceftolozane in an In Vitro Infection Model'. Antimicrob Agents Chemother. 2013 vol. 57, No. 6, pp. 2809-2814.

Ambrose, et al: Pharmacokinetic-pharmacodynamic considerations in the design of hospital-acquired or ventilator-associated bacterial pneumonia studies: look before you leap!; Clin Infect Dis, 2010, vol. 51, Suppl 1, pp. 5103-S110.

American Thoracic Society; Infectious Diseases Society of America; Guidelines for the management of adults with hospital-acquired, ventilator-associated, and healthcare-associated pneumonia; Am J Respir Crit Care Med., 2005, vol. 171(4), pp. 388-416.

Baughman, et al: The diagnosis and treatment challenges in nosocomial pneumonia; Diagn Microbiol Infect Dis, vol. 33(2), pp. 131-139.

Bergogne-Berezin: Predicting the efficacy of antimicrobial agents in respiratory infections: is tissue concentration valid measure?; J Antimicrob Chemother, 1995, vol. 35, pp. 363-371.

Boselli, et al: Steady-state plasma and intrapulmonary concentrations of piperacillin/tazobactam 4 g10.5 g administered to critically ill patients with severe nosocomial pneumonia; Intensive Care Med, 2004, vol. 30, pp. 976-979.

Boselli, et al: Alveolar concentrations of piperacillin/tazobactam administered in continuous infusion to patients with associated pneumonia; Crit Care Med, 2008, vol. 36, pp. 1500-1506.

Chastre, et al: Ventilator-associated pneumonia; Am J Respir Crit Care Med, 2002, vol. 165(7), pp. 867-903.

Chastre, et al: Comparison of 8 vs 15 days of antibiotic therapy for ventilator-associated pneumonia in adults: a randomized trial; JAMA, 2003, vol. 290(19), pp. 2588-2598.

El Solh: Update on the treatment of Pseudomonas aeruginosa pneumonia; J Antimicrob Chemother, 2009, vol. 64, pp. 229-238.

Freire, et al: Comparison of tigecycline with imipenem/cilastatin for the treatment of hospital-acquired penumonia; Diag Microbio and Infec Dis, 2010, vol. 68, pp. 140-151.

Harrison's Principles of Internal Medicine: Hospital-Acquired (Nosocomial) Pneumonia; ed. Kasper, et al.; 16th ed. New York: McGraw-Hill, Medical Pub. Division. 2005, pp. 1538-1541.

Jones, et al: Microbial etiologies of hospital-acquired bacterial pneumonia and ventilator-associated bacterial pneumonia; Clin Infect Dis; 2010, Suppl 1, pp. S81-S87.

Joseph, et al: Ventilator-associated pneumonia: A Review; EurJ Intern Med; 2010, vol. 21(5), pp. 360-368.

Klevens, et al: Estimating health care-associated infections and deaths in U.S. hospitals, 2002; Public Health Rep, 2007, vol. 122, pp. 160-166.

Knaus, et al: APACHE II: A severity of disease classification system; Crit Care Med, 1985, vol. 13, pp. 818-829.

Komuro, et al: Inhibition of the renal excretion of tazobactam by piperacillin; J Antimicrob Chemother, 1994, vol. 34, pp. 555-564.

Lucasti: A Phase 3, Randomized, Double-Blind Study of Ceftobiprole Medocaril Versus Linezolid Plus Ceftazidime in the Treatment of Nosocomial Pneumonia; Ceftobiprole: Clinical Study Report Synopsis BAP00248/307; Issue Date: Jul. 14, 2010; Document No. EDMS-PSDB-6906024:3.0, (8 pages).

Mesaros,, et al: Pseudomonas aeruginosa: resistance and therapeutic options at the turn of the new millennium; Clin Microbiol Infect, 2007, vol. 13, pp. 560-578.

Occhipinti, et al: Pharmacokinetics and pharmacodynamics of two multiple-dose piperacillin-tazobactam regimens; Antimicrob Agents Chemother, 1997, vol. 41, pp. 2511-2517.

Pankey: Tigecycline; J Antimicrob Chemotherapy, 2005, vol. 56, pp. 470-480.

Pea: The antimicrobial therapy puzzle: could pharmacokinetic-pharmacodynamic relationships be helpful in addressing the issue of appropriate pneumonia treatment in critically ill patients?; Clin Infect Dis, 2006, vol. 42, pp. 1764-1771.

Richards, et al: Nosocomial infections in medical intensive care units in the United States. National Nosocomial Infections Surveillance System; Crit Care Med, 1999, vol. 27(5), pp. 887-892.

Schulgen, et al: Estimation of extra hospital stay attributable to nosocomial infections: heterogeneity and timing of events; J Clin Epidemiol; Apr. 2000, vol. 53(4), pp. 409-417.

Singh:et al: Short-course empiric antibiotic therapy for patients with pulmonary infiltrates in the intensive care unit. A proposed solution for indiscriminate antibiotic prescription; Am J Respir Crit Care Med, Aug. 2000, vol. 162(2, Pt 1), pp. 505-511.

Udy, et al: Augmented renal clearance: implications for antibacterial dosing in the critically ill; Clin Pharmacokinet, 2010, vol. 49(1), pp. 1-16.

Vincent, et al: Use of the SOFA score to assess the incidence of organ dysfunction/failure in intensive care units: results of a multicenter, prospective study. Working group on "sepsis-related problems" of the European Society of Intensive Care Medicine; Crit Care Med, 1998, vol. 26(11), pp. 1793-1800.

Wunderink, et al: Linezolid in methicillin-resistant *Staphylococcus aureus* nosocomial pneumonia: a randomized, controlled study; Clin Infect Dis, 2012, vol. 54(5), pp. 621-629.

Zilberberg, et al: Epidemiology of healthcare-associated pneumonia (HCAP); Semin Respir Crit Care Med, 2009, vol. 30, pp. 10-15.

Zosyn®. Prescribing Information. Wyeth Pharmaceuticals, Inc., Philadelphia, PA, USA; http://labeling.pfizer.com/showlabeling.aspx?id=416 (Apr. 23, 2012, date last accessed), 26 pages.

* cited by examiner

CEFTOLOZANE ANTIBIOTIC COMPOSITIONS

CROSS-REFERENCE TO RELATED APPLICATIONS

This application is a continuation of U.S. application Ser. No. 14/856,075, filed Sep. 16, 2015, which claims the benefit of U.S. Provisional Application No. 62/051,859, filed Sep. 17, 2014 and is a continuation-in-part application of U.S. application Ser. No. 14/251,381, filed Apr. 11, 2014, which is a continuation application of International Application No. PCT/US2014/028642, filed Mar. 14, 2014, which claims priority to U.S. Provisional Application No. 61/792,092, filed Mar. 15, 2013; U.S. Provisional Application No. 61/793,007, filed Mar. 15, 2013; U.S. Provisional Application No. 61/882,936, filed Sep. 26, 2013; and U.S. Provisional Application No. 61/893,436, filed Oct. 21, 2013. The contents of these applications are incorporated hereby by reference in their entirety.

TECHNICAL FIELD

This disclosure relates to pharmaceutical compositions comprising ceftolozane, pharmaceutical compositions comprising tazobactam and ceftolozane, methods of preparing those compositions, and related methods and uses thereof.

BACKGROUND

Ceftolozane is a cephalosporin antibacterial agent. The antibacterial activity of ceftolozane is believed to result from its interaction with penicillin binding proteins (PBPs) to inhibit the biosynthesis of the bacterial cell wall which acts to stop bacterial replication. Ceftolozane is also referred to as "CXA-101", FR264205, (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadizol-3-yl)-2-[(1-carboxy-1-methylethoxy)imino]acetyl}amino)-8-oxo-5-thia-1-azabicyclo[4.2.0]oct-2-ene-2-carboxylate, or (6R,7R)-3-[5-Amino-4-[3-(2-aminoethyl)ureido]-1-methyl-1H-pyrazol-2-ium-2-ylmethyl]-7-[2-(5-amino-1,2,4-thiadiazol-3-yl)-2-[(Z)-1-carboxy-1-methylethoxyimino]acetamido]-3-cephem-4-carboxylic acid). As used herein, the term "ceftolozane" means (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate or (6R,7R)-3-[5-Amino-4-[3-(2-aminoethyl)ureido]-1-methyl-1H-pyrazol-2-ium-2-ylmethyl]-7-[2-(5-amino-1,2,4-thiadiazol-3-yl)-2-[(Z)-1-carboxy-1-methylethoxyimino]acetamido]-3-cephem-4-carboxylic acid in its free-base or salt form, including a sulfate form. Unless otherwise indicated, the term "CXA-101" as used herein can refer to ceftolozane in any pharmaceutically acceptable form, e.g., ceftolozane in its free-base or salt form, including a ceftolozane sulfate salt form. Ceftolozane sulfate is a pharmaceutically acceptable salt of ceftolozane that can be combined with sodium chloride and other components to obtain an antibiotic composition suitable for administration by injection or infusion.

Antibacterial pharmaceutical compositions can include ceftolozane as a pharmaceutically acceptable salt formulated for intravenous administration. Ceftolozane sulfate is a pharmaceutically acceptable ceftolozane salt of formula (I) that can be formulated for intravenous administration or infusion.

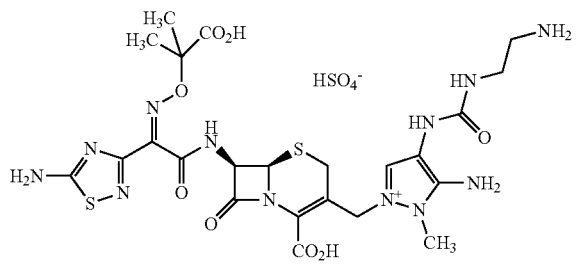

(I)

U.S. Pat. No. 7,129,232 discloses ceftolozane and various ceftolozane salts. For example, a ceftolozane hydrogen sulfate salt is disclosed among ceftolozane salts that can be formed "with a base or an acid addition salt such as a salt with an inorganic base, for example, an alkali metal salt [e.g., sodium salt, potassium salt, etc.], an alkaline earth metal salt [e.g., calcium salt, magnesium salt, etc.], an ammonium salt; a salt with an organic base, for example, an organic amine salt [e.g., trimethylamine salt, triethylamine salt, pyridine salt, picoline salt, ethanolamine salt, triethanolamine salt, dicyclohexylamine salt, N,N'-dibenzylethylenediamine salt, etc.]; an inorganic acid addition salt [e.g., hydrochloride, hydrobromide, sulfate, hydrogen sulfate, phosphate, etc.]; an organic carboxylic or sulfonic acid addition salt [e.g., formate, acetate, trifluoroacetate, maleate, tartrate, citrate, fumarate, methanesulfonate, benzenesulfonate, toluenesulfonate, etc.]; and a salt with a basic or acidic amino acid [e.g., arginine, aspartic acid, glutamic acid, etc.]."

Antibiotic pharmaceutical compositions comprising a beta-lactam antibiotic compound (e.g., a cephalosporin) (i.e., an antibiotic compound possessing one or more beta-lactam moieties) can be administered with a beta-lactamase inhibitor (BLI) compound. For example, beta-lactam antibiotic compounds such as ceftolozane or other cephalosporin antibiotic compounds can be formulated with, and/or administered in combination with beta-lactamase inhibiting compounds (e.g., tazobactam and salts thereof) in order to mitigate the effects of bacterial beta-lactamase enzymes that can lead to bacterial resistance to antibiotic therapy. Tazobactam is a BLI compound approved for use in fixed dose combination with piperacillin in an injectable antibacterial product available under commercial names ZOSYN (U.S.) and TAZOCIN (e.g., in Canada, and the United Kingdom). Tazobactam sodium, a derivative of the penicillin nucleus, is a penicillanic acid sulfone having the chemical name sodium (2S,3S,5R)-3-methyl-7-oxo-3-(1H-1,2,3-triazol-1-ylmethyl)-4-thia-1-azabicyclo[3.2.0]heptane-2-carboxylate-4,4-dioxide. The chemical formula is $C_{10}H_{11}N_4NaO_5S$ and the molecular weight is 322.3. The chemical structure of tazobactam sodium is:

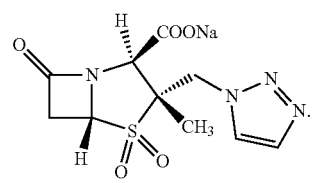

Ceftolozane can be formulated with tazobactam in antibiotic compositions called CXA-201 (ceftolozane/tazobactam for injection), comprising ceftolozane and tazobactam in a 2:1 weight ratio between the amount of ceftolozane active and the amount of tazobactam acid, regardless of the salt forms of these compositions (e.g., 1,000 mg of ceftolozane active can be included in about 1,147 mg of ceftolozane sulfate). CXA-201 compositions include an amount of tazobactam in a pharmaceutically acceptable form providing 500 mg of tazobactam acid per 1,000 mg of ceftolozane active as a composition formulated for injection, or for reconstitution prior to parenteral administration. In one product presentation, CXA-201 can be provided in a single container comprising ceftolozane sulfate and tazobactam sodium, administered by reconstituting a container-unit dosage form container of solid CXA-201 to form a reconstituted injectable formulation. In one presentation (e.g., for treatment of certain urinary tract infections and/or certain intr-abdominal infections), each unit dosage form container of CXA-201 can contain 1000 mg of ceftolozane active (free base equivalent weight, e.g., provided as a pharmaceutically acceptable salt such as ceftolozane sulfate) and sterile tazobactam sodium at a quantity equivalent of 500 mg of tazobactam free acid, in a solid form. In another presentation (e.g., for treatment of hospital acquired/ventilator-associated bacterial pneumonia (HABP/VABP)), a CXA-201 product can include a unit dosage form container providing 2,000 mg of ceftolozane active (e.g., as an equivalent amount of ceftolozane sulfate) and 1,000 mg of tazobactam acid (e.g., as an equivalent amount of tazobactam sodium). CXA-201 compositions display potent antibacterial activity against various gram-negative infections such as, for example, complicated intra-abdominal infection (cIAI), complicated urinary tract infection (cUTI), or hospital acquired/ventilator-associated bacterial pneumonia (HABP/VABP).

As disclosed herein, ceftolozane was initially found to be chemically unstable in certain lyophilized compositions evaluated during the development of CXA-101 and CXA-201 pharmaceutical compositions. For example, ceftolozane had a residual rate of about 51% in the absence of a stabilizing agent during both a 3 day stability test at 70 degrees C., indicating loss of almost half of the ceftolozane during the test (Example 2, Table 2A control sample), and a 5.88% reduction in ceftolozane purity during a 7 day stability test at 60 degrees C. in the absence of a stabilizing agent (Example 2, Table 2B control sample). Second, the formation of a number of additional ceftolozane degradation products formed during the preparation of initial compositions was observed by additional peaks using high performance liquid chromatography (HPLC) during stability tests of ceftolozane alone (e.g., Peak P12 in Table 4 of Example 3, and the RT63' peak in Table 15 of Example 8), and testing of compositions with tazobactam and ceftolozane formed by co-lyophilization of ceftolozane and tazobactam (e.g., RRT 1.22 peak in Tables 12 and 13 of Example 7a). Accordingly, there remains an unmet need to identify formulations and manufacturing methods that effectively stabilize ceftolozane both in a solid and liquid form to provide suitably stable pharmaceutical compositions comprising ceftolozane and tazobactam (both in a powder form for reconstitution and in a reconstituted form for parenteral delivery). These formulations should address the need to provide pharmaceutical compositions having desired levels of ceftolozane and tazobactam potency, as well as levels of impurities that are therapeutically acceptable for parenteral administration.

SUMMARY

As provided herein, ceftolozane can be stabilized in pharmaceutical composition comprising ceftolozane and a stabilizing effective amount of a stabilizing agent selected from the group consisting of: sodium chloride, dextran 40, lactose, maltose, trehalose and sucrose. The pharmaceutical compositions provided herein are based in part on the surprising discovery that ceftolozane pharmaceutical compositions comprising these stabilizing agents demonstrate improved ceftolozane residual rates (e.g., % ceftolozane remaining after 3 days at 70° C. as measured by HPLC) and/or chemical stability (e.g., lower reduction in ceftolozane purity measured by HPLC after 7 days at 60° C. in a stability test) compared control samples comprising ceftolozane without a stabilizing agent.

Accordingly, preferred pharmaceutical antibiotic compositions can include ceftolozane sulfate and a stabilizing agent (e.g., 300 to 500 mg of a stabilizing agent per 1,000 mg ceftolozane active) in a lyophilized unit dosage form (e.g., powder in a container). The unit dosage form can be dissolved with a pharmaceutically acceptable carrier (e.g., 0.9% sodium chloride aqueous isotonic saline and/or water for injection), and then intravenously administered. In certain ceftolozane compositions, the stabilizing agent can be selected from the group consisting of: sodium chloride, lactose, maltose and dextran 40, and/or selected from the group consisting of: sodium chloride, trehalose and sucrose.

In addition, the present disclosure provides ceftolozane pharmaceutical compositions based in part on the surprising discovery that ceftolozane pharmaceutical compositions comprising about 1000 mg of ceftolozane active per 189 mg sodium from sodium chloride demonstrate improved chemical stability and purity compared with pharmaceutical compositions comprising ceftolozane with comparatively less sodium chloride. For example, the invention is based in part on the discovery of the absence of the "RT63 Impurity" (also referred to herein as "Formula III") in HPLC analysis of pharmaceutical compositions comprising about 1,000 mg of ceftolozane and 189 mg sodium from sodium chloride. By comparison, reducing the amount of sodium chloride relative to ceftolozane in tested compositions resulted in at least 1.5-fold greater impurity at RT=63 minutes (observed by HPLC using the method described in Example 1). The ceftolozane formulations with reduced levels of sodium were not as stable as the ceftolozane formulation containing about 1,000 mg of ceftolozane per 189 mg sodium from sodium chloride per. Ceftolozane formulations containing about 1,000 mg of ceftolozane effective per stabilizing-effective amount of sodium from sodium chloride maintained the level of RT63 Impurity below the detection limit (e.g., 0.03%) measured by HPLC using the method described in Example 1, i.e.:

| Column | Develosil ODS-UG-5, 5 μm, 250 × 4.6 mm |
|---|---|
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

In a further embodiment provided herein, ceftolozane sulfate is stabilized in pharmaceutical compositions by incorporation of an effective amount of an inorganic salt stabilizing agent, in particular 125 to 500 mg (e.g., 480 to 500 mg) of sodium chloride per gram of ceftolozane active. This is based in part on the surprising discovery that ceftolozane pharmaceutical compositions comprising 125 to 500 mg (e.g., 480 to 500 mg) of sodium chloride per 1000 mg of ceftolozane active demonstrate improved ceftolozane purity and chemical stability compared to pharmaceutical compositions comprising ceftolozane with comparatively less sodium chloride. For example, the disclosed pharmaceutical compositions have an improved stability as a decrease in the rate of ceftolozane purity and/or a decrease in the rate of formation of substances characterized by HPLC peaks 1 and 7 identified during a 7-day stability study in Example 5. The disclosed ceftolozane pharmaceutical compositions comprise a stabilizing amount of sodium chloride (e.g., 125 to 500 mg of sodium chloride [more specifically, 480 to 500 mg] per 1000 mg of ceftolozane active). Certain preferred compositions demonstrate improved ceftolozane purity (e.g., Table 6) and chemical stability (e.g., with respect to the composition of HPLC peak 1 in Table 7) compared with pharmaceutical compositions comprising ceftolozane with comparatively less sodium chloride. For example, the disclosed pharmaceutical compositions typically comprise less than about 4% total impurity after being stored for seven days at 60° C., as determined by HPLC using the method described in Example 1. Alternatively, the disclosed pharmaceutical compositions comprise less than about 2% of the impurity represented by Peak 1 after being stored for seven days at 60° C., as determined by HPLC using the method described in Example 1, where Peak 1 has a retention time relative to ceftolozane of 0.1, i.e.:

| Column | Develosil ODS-UG-5, 5 µm, 250 × 4.6 mm | | |
|---|---|---|---|
| Column temperature | 45° C. ± 2° C. | | |
| Wavelength: | 254 nm for ceftolozane and ceftolozane-related substances in Table 1A | | |
| Mobile phase A | 50 mM Sodium Perchlorate Monohydrate in water, adjusted to pH 2.5 with Diluted Perchloric Acid | | |
| Mobile phase B | 63 mM Sodium Perchlorate Monohydrate in water, adjusted to pH 2.5 with Diluted Perchloric Acid:Acetonitrile, 4:1 (v/v) | | |
| | Time (min.) | % A | % B |
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

In an embodiment, pharmaceutical antibiotic compositions provided herein can include ceftolozane sulfate and stabilizing amount of sodium chloride (e.g., 125 to 500 mg more specifically 480 to 500 mg of sodium chloride and 1,000 mg ceftolozane active) in a unit dosage form (e.g., powder in a container). The unit dosage form can be dissolved with a pharmaceutically acceptable carrier, and then intravenously administered.

In another aspect, provided herein is a pharmaceutical composition comprising 125 mg to 500 mg sodium chloride per 1,000 mg of ceftolozane active, wherein the decrease in ceftolozane total purity is not greater than about 4% after storing the pharmaceutical composition for seven days in a sealed container at 60° C., as determined by HPLC using the method described in Example 1, i.e.:

| Column | Develosil ODS-UG-5, 5 µm, 250 × 4.6 mm | | |
|---|---|---|---|
| Column temperature | 45° C. ± 2° C. | | |
| Wavelength: | 254 nm for ceftolozane and ceftolozane-related substances in Table 1A | | |
| Mobile phase A | 50 mM Sodium Perchlorate Monohydrate in water, adjusted to pH 2.5 with Diluted Perchloric Acid | | |
| Mobile phase B | 63 mM Sodium Perchlorate Monohydrate in water, adjusted to pH 2.5 with Diluted Perchloric Acid:Acetonitrile, 4:1 (v/v) | | |
| | Time (min.) | % A | % B |
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

In another aspect, provided herein is a pharmaceutical composition comprising 125 mg to 500 mg sodium chloride per 1,000 mg of ceftolozane active, wherein the increase in the amount of the impurity represented by Peak 1 is not greater than about 2% after storing the pharmaceutical composition for seven days at 60° C., as determined by HPLC using the method described in Example 1, where Peak 1 has a retention time relative to ceftolozane of about 0.1, i.e.:

| Column | Develosil ODS-UG-5, 5 µm, 250 × 4.6 mm | | |
|---|---|---|---|
| Column temperature | 45° C. ± 2° C. | | |
| Wavelength: | 254 nm for ceftolozane and ceftolozane-related substances in Table 1A | | |
| Mobile phase A | 50 mM Sodium Perchlorate Monohydrate in water, adjusted to pH 2.5 with Diluted Perchloric Acid | | |
| Mobile phase B | 63 mM Sodium Perchlorate Monohydrate in water, adjusted to pH 2.5 with Diluted Perchloric Acid:Acetonitrile, 4:1 (v/v) | | |
| | Time (min.) | % A | % B |
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

In embodiments of these aspects, the pharmaceutical composition further comprises L-arginine, or citric acid. In other embodiments, the pharmaceutical composition is formulated for parenteral administration. In another embodiment, the compositions can be in a unit dosage form comprising 125 mg to 500 mg sodium chloride, 1,000 mg of ceftolozane in the form of ceftolozane sulfate, L-arginine and citric acid.

In other embodiments of these aspects, the pharmaceutical composition is lyophilized. In another embodiment, the ceftolozane is ceftolozane sulfate.

In another aspect, provided herein is a unit dosage form injectable pharmaceutical composition comprising 125 mg to 500 mg sodium chloride and 1,000 mg of ceftolozane active present as a composition of formula (I)

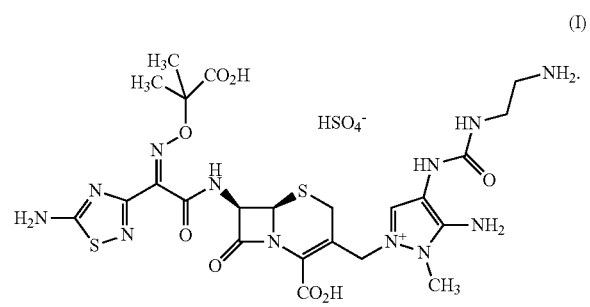 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1]

(I)

In another aspect, provided herein is a pharmaceutical composition comprising 125 mg to 500 mg sodium chloride per 1,000 mg of ceftolozane active present as ceftolozane sulfate, wherein the ceftolozane total purity is at least about 94% after storing the pharmaceutical composition for three days at 60° C., as determined by HPLC using the method described in Example 1, i.e.:

| Column | Develosil ODS-UG-5, 5 µm, 250 × 4.6 mm |
|---|---|
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

Applicants have further discovered pharmaceutical compositions comprising ceftolozane and tazobactam with reduced and even undetectable amounts of the compound RRT 1.22, and methods of manufacturing these compositions. This is based in part on the discovery that the formation of RRT 1.22 can be reduced if not completely suppressed by lyophilizing ceftolozane in the absence of tazobactam and then blending the lyophilized ceftolozane with a dry tazobactam composition, such as a tazobactam composition lyophilized in the absence of ceftolozane (See Example 10 and the results reported in Tables 23 and 24). Based on these results, pharmaceutical compositions comprising ceftolozane and tazobactam, and pharmaceutical compositions prepared using ceftolozane and tazobactam are provided herein. In particular, these pharmaceutical compositions can include ceftolozane and/or tazobactam with reduced or even undetectable amounts of the compound RRT 1.22:

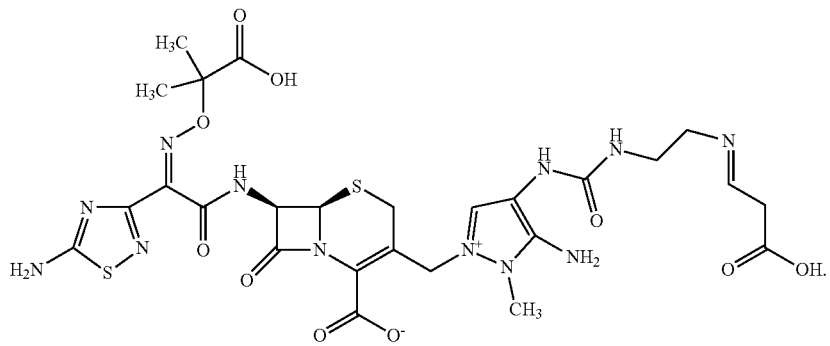 [SMILES: Cn1c(N)c(NC(=O)NCC/N=C/CC(=O)O)c[n+]1CC1=C(C(=O)[O-])N2C(=O)[C@@H](NC(=O)/C(=N\OC(C)(C)C(=O)O)c3nsc(N)n3)[C@H]2SC1]

In one embodiment, a pharmaceutical composition can include ceftolozane and tazobactam with less than 0.15%, 0.10%, 0.05% or 0.03% by weight; or from 0.03-0.05%, 0.03-0.1% or 0.03-0.15% by HPLC or even undetectable amounts of RRT 1.22 (e.g., less than about 0.03% of the compound RRT 1.22 measured by HPLC). These pharmaceutical compositions can be obtained by a process comprising the steps of (a) lyophilizing ceftolozane in the absence of tazobactam to obtain a lyophilized ceftolozane composition; and (b) combining the lyophilized ceftolozane with tazobactam under conditions suitable to obtain said pharmaceutical composition with the aforementioned purity levels. The combination of the lyophilized ceftolozane composition with tazobactam can include blending the lyophilized ceftolozane composition with lyophilized or crystalline tazobactam material.

Also provided herein is a pharmaceutical composition comprising a blend of separately lyophilized tazobactam and ceftolozane sulfate in an amount providing 1,000 mg of ceftolozane active per 500 mg of tazobactam active, further comprising less than 0.15%, 0.10%, 0.05% or 0.03% by weight; from 0.03-0.05%, 0.03-0.1% or 0.03-0.15% by HPLC; or even undetectable amounts (e.g., less than about 0.03% by HPLC) of a compound of formula (III) detectable at a retention time relative to ceftolozane of 1.22 by high performance liquid chromatography (HPLC) using the method of Example 1, i.e.:

| Column | Develosil ODS-UG-5, 5 μm, 250 × 4.6 mm |
|---|---|
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

CXA-201 compositions comprising less than about 0.15%, 0.10%, 0.05% or 0.03% by weight; or from 0.03-0.05%, 0.03-0.1% or 0.03-0.15% by HPLC of the compound of formula (III) can be obtained by a process comprising the steps of: (a) forming a first aqueous solution comprising ceftolozane (e.g., in a pharmaceutically acceptable salt such as formula (I)), (b) lyophilizing the first aqueous solution to obtain a lyophilized ceftolozane composition, and (c) blending the lyophilized ceftolozane composition with a tazobactam composition (e.g., tazobactam acid lyophilized in the absence of ceftolozane) in an amount that provides a 2:1 weight ratio between the amount of ceftolozane active and tazobactam active.

In yet another aspect, provided herein is a method for the treatment of a bacterial infection in a mammal, comprising administering to said mammal a therapeutically effective amount of any one of the pharmaceutical compositions provided herein. In an embodiment, the bacterial infection is caused by the bacterial infection is caused by bacteria selected from the group consisting of: *Staphylococcus aureus*, *Escherichia coli*, *Acinetobacter baumanii*, *Haemophilus influenzae*, *Klebsiella pneumonia*, and *Pseudomonas aeruginosa*. In another embodiment, the bacterial infection is selected from the group consisting of nosocomial pneumonia, complicated intra-abdominal infection and complicated urinary tract infection.

In yet another aspect, any of the pharmaceutical compositions provided herein may be used for the manufacture of a medicament for the treatment of complicated intra-abdominal infection (cIAI), complicated urinary tract infection (cUTI), or hospital acquired/ventilator-associated bacterial pneumonia (HABP/VABP).

In still another aspect provided herein, an antibiotic pharmaceutical composition comprises ceftolozane (or a pharmaceutically acceptable salt thereof) and tazobactam (or a pharmaceutically acceptable salt thereof) in a fixed dose combination of 1,000 mg of ceftolozane active per 500 mg of tazobactam active, and a ceftolozane-stabilizing amount of 125 mg to 500 mg sodium chloride per 1,000 mg of ceftolozane active.

In a further aspect disclosed herein, a pharmaceutical composition comprising stabilized ceftolozane sulfate is obtained by a process comprising lyophilizing an aqueous solution comprising 125 mg to 500 mg sodium chloride with an amount of ceftolozane sulfate providing 1,000 mg of ceftolozane active, to obtain the lyophilized stabilized ceftolozane sulfate composition.

Yet another aspect provided herein discloses an antibacterial pharmaceutical composition comprising ceftolozane sulfate and tazobactam in a ratio of 1,000 mg ceftolozane active per 500 mg of tazobactam active, the pharmaceutical composition obtained by a process comprising the steps of:

a) lyophilizing a first aqueous solution in the absence of tazobactam, the first aqueous solution comprising ceftolozane sulfate prior to lyophilization to obtain a first lyophilized ceftolozane composition; and b) blending the first lyophilized ceftolozane composition with tazobactam to obtain an antibacterial composition comprising less than 0.13% by HPLC of a compound of formula (III) detectable at a retention time relative to ceftolozane of 1.22 by high performance liquid chromatography using the method described in Example 1, i.e.:

| Column | Develosil ODS-UG-5, 5 μm, 250 × 4.6 mm |
|---|---|
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 | to detect:

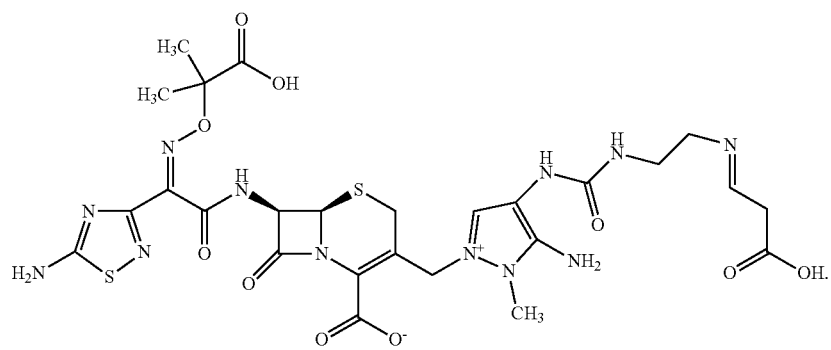

(III)

DETAILED DESCRIPTION

I. Stabilizing Ceftolozane

Figure 1:
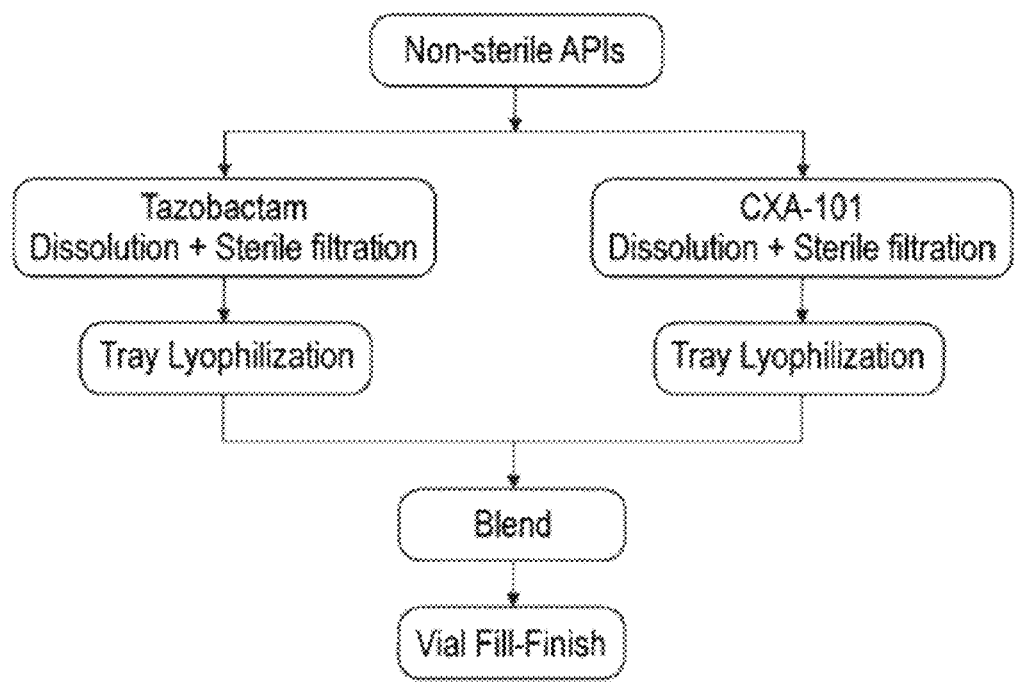
FIG. 1 is a flowchart showing the steps for preparing a CXA-201 composition comprising ceftolozane (referred to as CXA-101) and tazobactam using a blending process, wherein the ceftolozane and tazobactam are lyophilized separately prior to blending as described herein.

Ceftolozane can be stabilized in a pharmaceutical composition comprising ceftolozane and a stabilizing effective amount of a stabilizing agent selected from the group consisting of: sodium chloride, dextran 40, lactose, maltose, trehalose and sucrose. The stabilizing agent and the stabilizing effective amount of the stabilizing agent for combination with ceftolozane were determined by high performance liquid chromatography (HPLC) analysis, for example by detecting the ratio of peak areas obtained for ceftolozane compared to peaks for other substances.

Preferred stabilized ceftolozane compositions have a ceftolozane residual rate of greater than the residual rate measured for a comparable ceftolozane composition without the stabilizing agent. Unless otherwise indicated, the residual rate is measured by detecting the amount of ceftolozane in a sample before and after a stability test using HPLC, and determining the percentage of ceftolozane last during the stability test.

Referring to Example 2 (including Table 2A), the residual rate of ceftolozane in the control sample without a stabilizing agent (i.e., 100 mg of ceftolozane) after 3 days at 70 degrees C. was 51.2%, meaning that the HPLC peak area after the stability test for ceftolozane was about 51.2% of the HPLC peak area for ceftolozane at the start of the stability test (i.e., 3 days at 70 degrees C.). Sodium chloride, dextran 40, lactose and maltose all showed higher ceftolozane residual rates than the control in Example 2, while ceftolozane was less stable than the control when combined with fructose, xylitol, sorbitol and glucose (e.g., as evidenced by a residual rate lower than that of the control). In one embodiment, stabilized ceftolozane compositions comprise ceftolozane (e.g., ceftolozane sulfate) and a stabilizing effective amount of a stabilizing agent selected from the group consisting of: sodium chloride, dextran 40, lactose and maltose, where the stabilizing effective amount provides a residual rate of at least 51.2% for the ceftolozane in the stabilized ceftolozane composition after 3 days at 70 degrees C. Preferably, the stabilized ceftolozane pharmaceutical compositions after 3 days at 70 degrees C. can comprise at least about 70% of an initial amount of the stabilized ceftolozane in the pharmaceutical composition (i.e., a residual rate of about 70% or greater, as shown in Example 2), where the % of ceftolozane is measured by high performance liquid chromatography (HPLC) according to Example 1, i.e.:

| | |
|---|---|
| Column | Develosil ODS-UG-5, 5 μm, 250 × 4.6 mm |
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |

| | | |
|---|---|---|
| 85.1 | 75 | 25 |
| 110 | 75 | 25 |

Referring to Example 2 (Table 2A), stabilized ceftolozane compositions are characterized by a reduction in ceftolozane of less than about 5% after 7 days at 60 degrees C., where the % reduction of ceftolozane is measured by HPLC according to Example 1. The stabilized ceftolozane pharmaceutical composition comprising ceftolozane and a stabilizing agent selected from the group consisting of: sodium chloride, trehalose and sucrose can lose less than 5% of the amount of ceftolozane after 7 days at 60 degrees C., where the % loss of ceftolozane is measured by HPLC according to Example 1. Sodium chloride, trehalose and sucrose all showed reduced reductions in ceftolozane purity after a 7 day stability test at 60 degrees C. (as measured by the % HPLC peak corresponding to ceftolozane before and after the stability test). In one embodiment, stabilized ceftolozane compositions comprise ceftolozane (e.g., ceftolozane sulfate) and a stabilizing effective amount of a stabilizing agent selected from the group consisting of: sodium chloride, trehalose and sucrose, where the stabilizing effective amount provides a reduction in ceftolozane purity of not more than about 5% (e.g, not more than about 4%) for the ceftolozane in the stabilized ceftolozane composition after 3 days at 70 degrees C.

Accordingly, in one aspect, provided herein is a pharmaceutical composition comprising stabilized ceftolozane obtained by a process comprising lyophilizing a composition including ceftolozane and a stabilizing agent selected from the group consisting of: sodium chloride, dextran 40, lactose, maltose, tehalose and sucrose, to obtain a lyophilized stabilized ceftolozane pharmaceutical composition. In an embodiment, the stabilizing agent is selected from the group consisting of: sodium chloride, trehalose and sucrose. In another aspect, provided herein is a pharmaceutical composition comprising stabilized ceftolozane and a stabilizing agent selected from the group consisting of: sodium chloride, dextran 40, lactose, maltose, tehalose and sucrose, wherein the pharmaceutical composition after 3 days at 70 degrees C. comprises at least about 70% of an initial amount of the stabilized ceftolozane in the pharmaceutical composition.

In another aspect, provided herein is a container containing a unit dosage form of a pharmaceutical composition formulated for parenteral administration for the treatment of complicated intra-abdominal infections or complicated urinary tract infections, the pharmaceutical composition comprising 1,000 mg of ceftolozane active, L-arginine, citric acid and about 300-500 mg of a stabilizing agent selected from the group consisting of: sodium chloride, trehalose, and sucrose, wherein the pharmaceutical composition after 3 days at 70 degrees C. comprises at least about 70% of an initial amount of the ceftolozane active in the pharmaceutical composition.

Various ceftolozane compositions are described herein. One stabilized ceftolozane composition comprises ceftolozane (e.g., ceftolozane sulfate), L-arginine, citric acid, and a stabilizing agent. Preferably, the stabilized ceftolozane composition comprises 1,000 mg of ceftolozane active, L-arginine and stabilizing-effective amount of the stabilizing agent. The stabilizing effective amount can be readily determined using HPLC and a stability test as disclosed herein. The stabilizing-effective amount can be effective to provide: (1) a residual rate measured by HPLC of ceftolozane of at least about 51.2% (including, e.g., at least about 70%, and at least about 80%) after 3 days at 70 degrees C. and/or (2) a reduction in ceftolozane purity measured by HPLC of not more than about 5.11% (including, e.g., reductions of not more than about 5%, or 4%) after 7 days at 60 degrees C. Examples of stabilizing effective amounts include 100 mg-500 mg of the stabilizing agent per 1,000 mg of the ceftolozane active, more preferably about 300-500 mg of the stabilizing agent per 1,000 mg of the ceftolozane active.

In the screening of ceftolozane stabilizing agents, it has been found that, surprisingly, a preferred amount of sodium chloride can improve the stability of ceftolozane, including ceftolozane in the ceftolozane sulfate form. For example, in one experiment, a ceftolozane composition comprising about 100 mg (about 1.71 mmol) sodium chloride per 100 mg (about 0.15 mmol) of ceftolozane was more stable compared to many ceftolozane compositions comprising known stabilizing sugars, such as fructose, xylitol, sorbitol, glucose, and D-mannitol, and as stable as other ceftolozane compositions comprising the same amount of certain sugars, such as dextran 40, lactose, and maltose (see Example 2). Interestingly, additional experiments demonstrated that the use of maltose in a ceftolozane composition resulted in a significant amount of additional compounds (see Example 3).

Surprisingly, pharmaceutical compositions comprising ceftolozane and 125 to 1000 mg sodium chloride per 1000 mg of ceftolozane have been observed to exhibit better chemical stability over the course of time and/or in the presence of heat, and fewer additional compounds than those pharmaceutical compositions comprising ceftolozane and less sodium chloride (i.e., less than 125 mg sodium chloride per 1000 mg of ceftolozane) (see, e.g., Example 5). In particular embodiments described herein, the pharmaceutical compositions comprising ceftolozane and 125 to 500 mg sodium chloride per 1000 mg of ceftolozane have been found to be more stable than the compositions comprising ceftolozane and less than 125 mg sodium chloride per 1000 mg of ceftolozane.

Ceftolozane compositions having 50-481 mg of sodium chloride per 1,000 mg ceftolozane active were prepared as described in Table 5 and tested for stability as described in Example 5. Ceftolozane was more stable in compositions containing at least 125 mg of sodium chloride per 1,000 mg of ceftolozane active, as measured by high performance liquid chromatography (HPLC) analysis by detecting the ratio of peak areas obtained for ceftolozane compared to peaks for other substances. Unless otherwise indicated, HPLC measurements reported herein are obtained using the conditions described in Example 1, i.e.:

| | | | |
|---|---|---|---|
| Column | Develosil ODS-UG-5, 5 µm, 250 × 4.6 mm | | |
| Column temperature | 45° C. ± 2° C. | | |
| Wavelength: | 254 nm for ceftolozane and ceftolozane-related substances in Table 1A | | |
| Mobile phase A | 50 mM Sodium Perchlorate Monohydrate in water, adjusted to pH 2.5 with Diluted Perchloric Acid | | |
| Mobile phase B | 63 mM Sodium Perchlorate Monohydrate in water, adjusted to pH 2.5 with Diluted Perchloric Acid:Acetonitrile, 4:1 (v/v) | | |
| | Time (min.) | % A | % B |
| Gradient Profile | 0 | 75 | 25 |
| | 30 | 70 | 30 |
| | 60 | 0 | 100 |
| | 85 | 0 | 100 |

-continued

| | | |
|---|---|---|
| 85.1 | 75 | 25 |
| 110 | 75 | 25 |

During the stability test of Example 5, ceftolozane samples containing 125 mg, 190 mg and 481 mg of sodium chloride per 1,000 mg of ceftolozane active showed a decrease in ceftolozane total purity measured by HPLC that was at least about 35% less than reductions in ceftolozane total purity observed for formulations containing 50 mg or 75 mg sodium chloride per 1,000 mg ceftolozane active. Thus, ceftolozane compositions having at least 125 mg or more sodium chloride relative to the fixed amount of ceftolozane were about 35-90% more stable than comparable ceftolozane compositions having less than 125 mg sodium chloride (e.g., the % decrease in ceftolozane for the sample containing 75 mg sodium chloride was about 35% greater than the comparable % decrease in ceftolozane for the sample containing 190 mg sodium chloride). In addition, samples obtained from ceftolozane compositions containing 125 mg, 190 mg and 481 mg of sodium chloride per 1,000 mg of ceftolozane active showed a decrease in ceftolozane that was up to about 90% less than reductions in ceftolozane observed for formulations containing 50 mg or 75 mg sodium chloride per (e.g., the % decrease in ceftolozane for the sample containing 50 mg sodium chloride was about 90% greater than the comparable % decrease in ceftolozane for the sample containing 481 mg sodium chloride).

Figure 4:
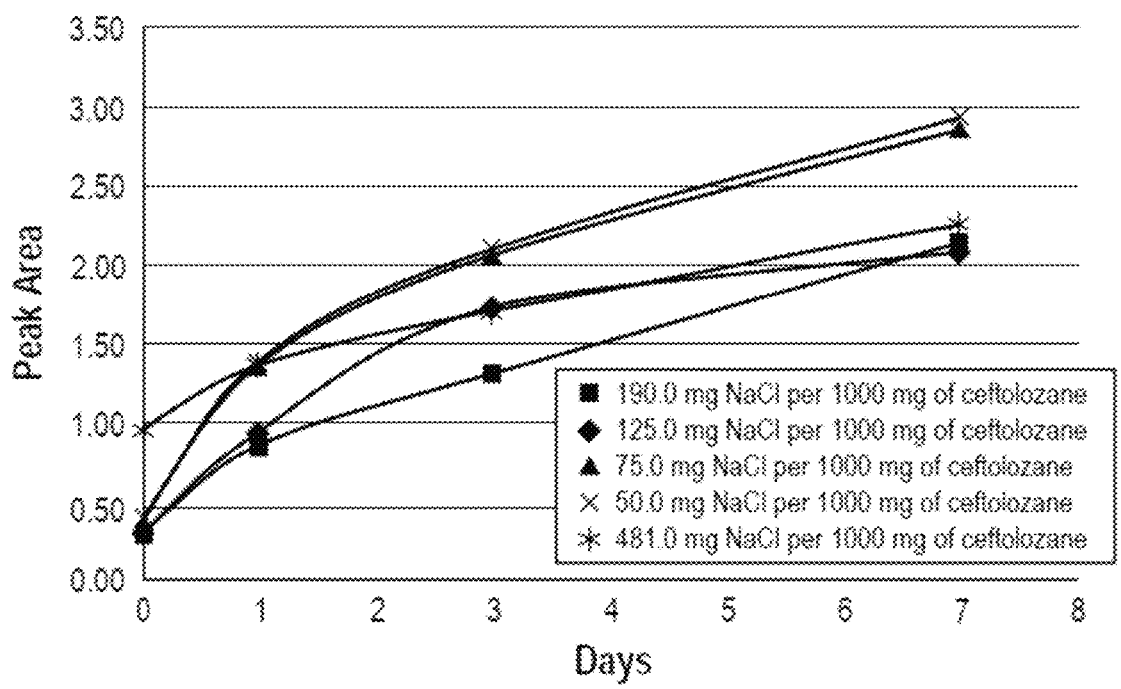
FIG. 4 is a plot of the data points from Table 7, showing the peak area of the composition peak 1 in CXA-101 compositions at 60° C. on day 0, day 1, day 3, and day 7, as measured by HPLC, wherein the CXA-101 compositions comprise ceftolozane and sodium chloride.
Figure 5:
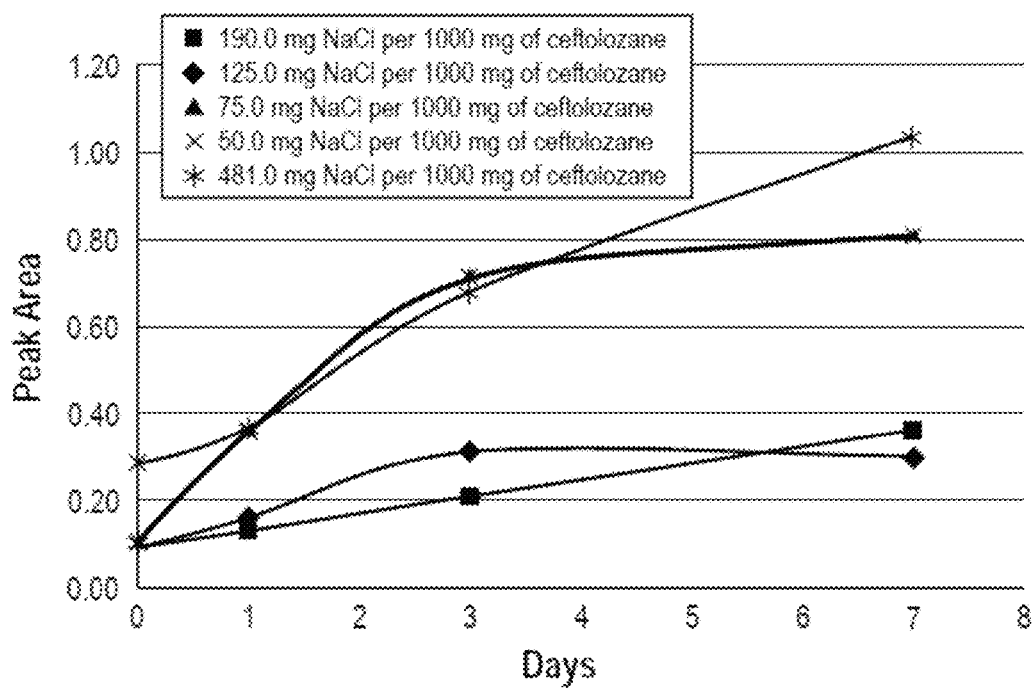
FIG. 5 is a plot of the data points from Table 8A, showing the total peak area of the composition with a RRT of 0.43 and the composition peak 3 in CXA-101 compositions at 60° C. on day 0, day 1, day 3, and day 7, as measured by HPLC, wherein the CXA-101 compositions comprise ceftolozane and sodium chloride.
Figure 6:
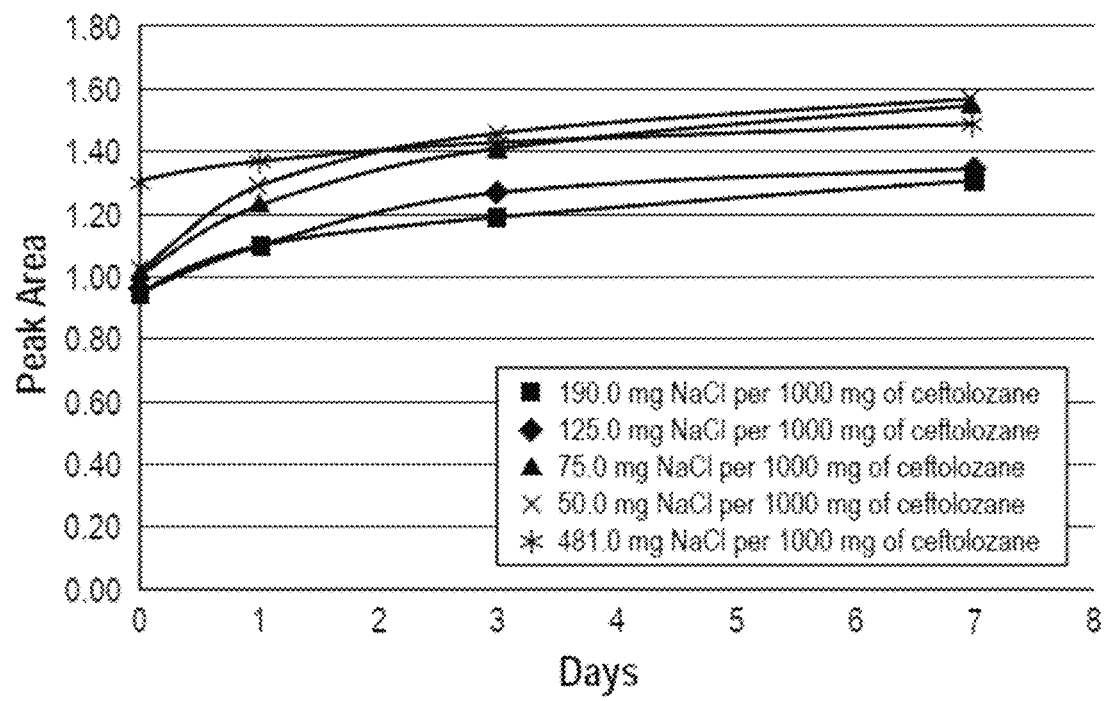
FIG. 6 is a plot of the data points from Table 8B, showing the peak area of the composition peak 7 in CXA-101 compositions at 60° C. on day 0, day 1, day 3, and day 7, as measured by HPLC, wherein the CXA-101 compositions comprise ceftolozane and sodium chloride.
Figure 7:
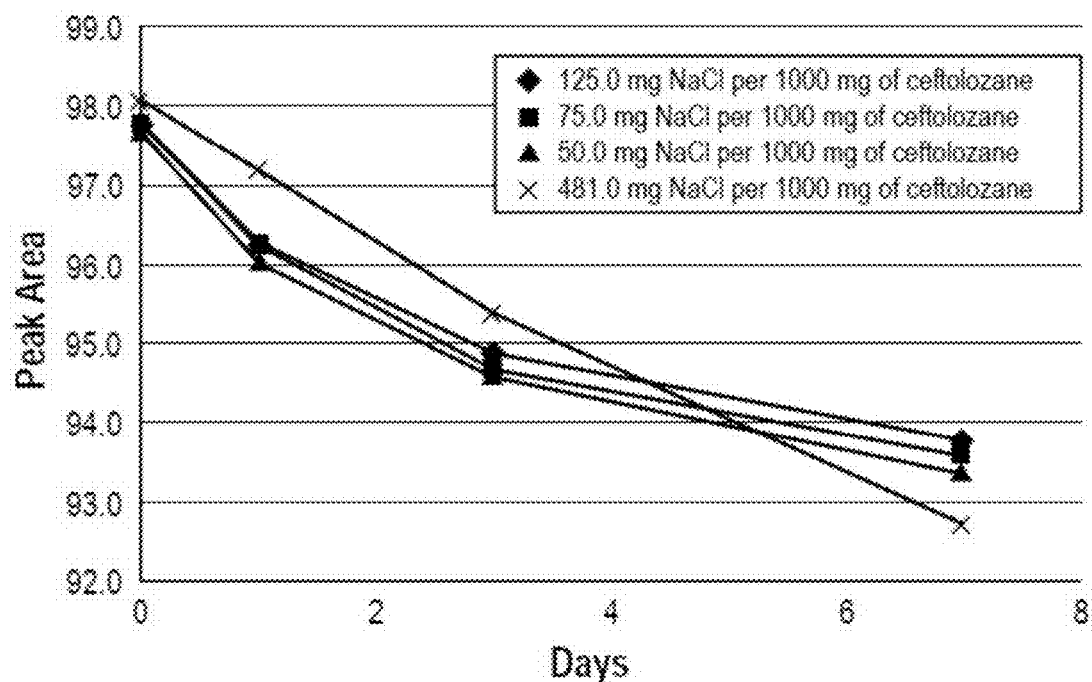
FIG. 7 is a plot of the data points from Table 17, showing the purity of ceftolozane in CXA-201 compositions at 60° C. on day 0, day 1, day 3, and day 7, as measured by HPLC, wherein the CXA-201 compositions comprise ceftolozane, tazobactam, and sodium chloride.
Figure 8:
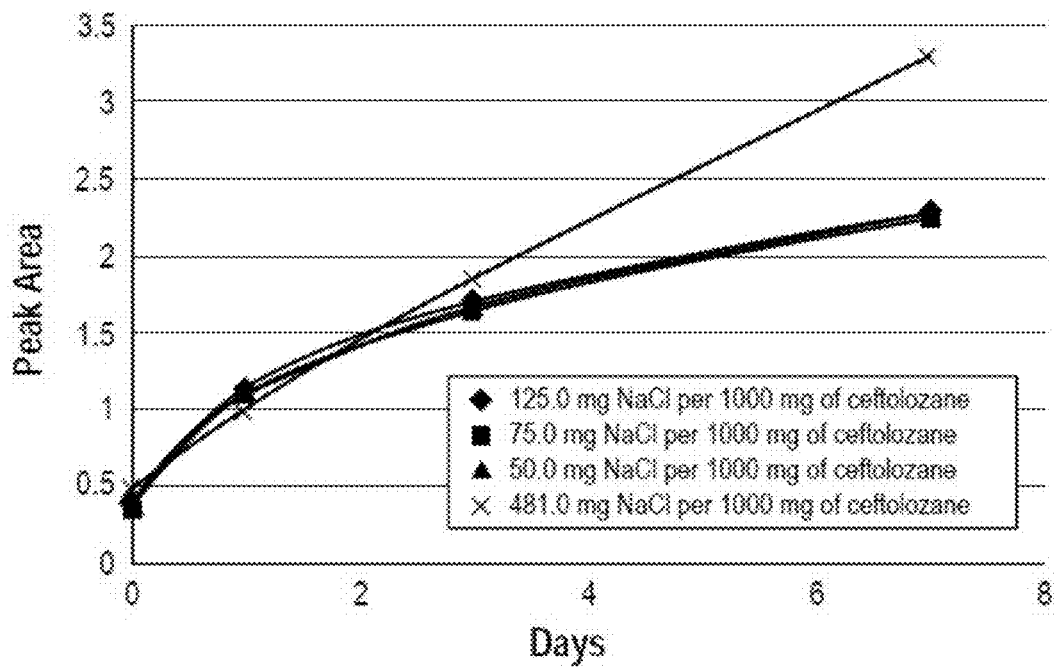
FIG. 8 is a plot of the data points from Table 18, showing the peak area of the composition peak 1 in CXA-201 compositions at 60° C. on day 0, day 1, day 3, and day 7, as measured by HPLC, wherein the CXA-201 compositions comprise ceftolozane, tazobactam, and sodium chloride.
Figure 9:
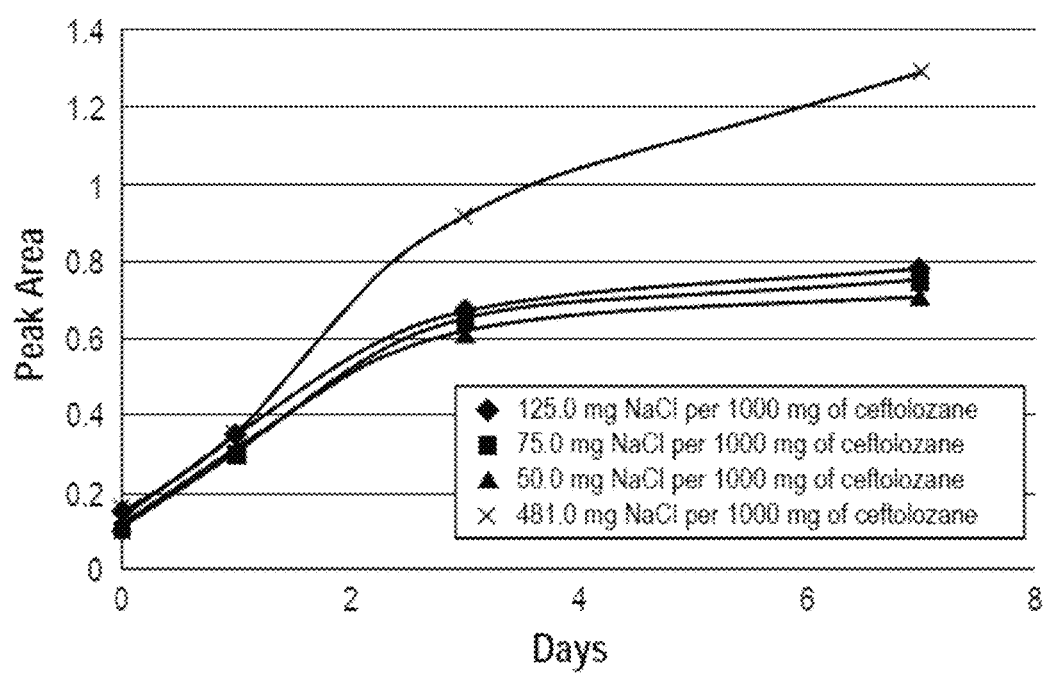
FIG. 9 is a plot of the data points from Table 19, showing the total peak area of the composition with a RRT of 0.43 and the composition peak 3 in CXA-201 compositions at 60° C. on day 0, day 1, day 3, and day 7, as measured by HPLC, wherein the CXA-201 compositions comprise ceftolozane, tazobactam, and sodium chloride.
Figure 10:
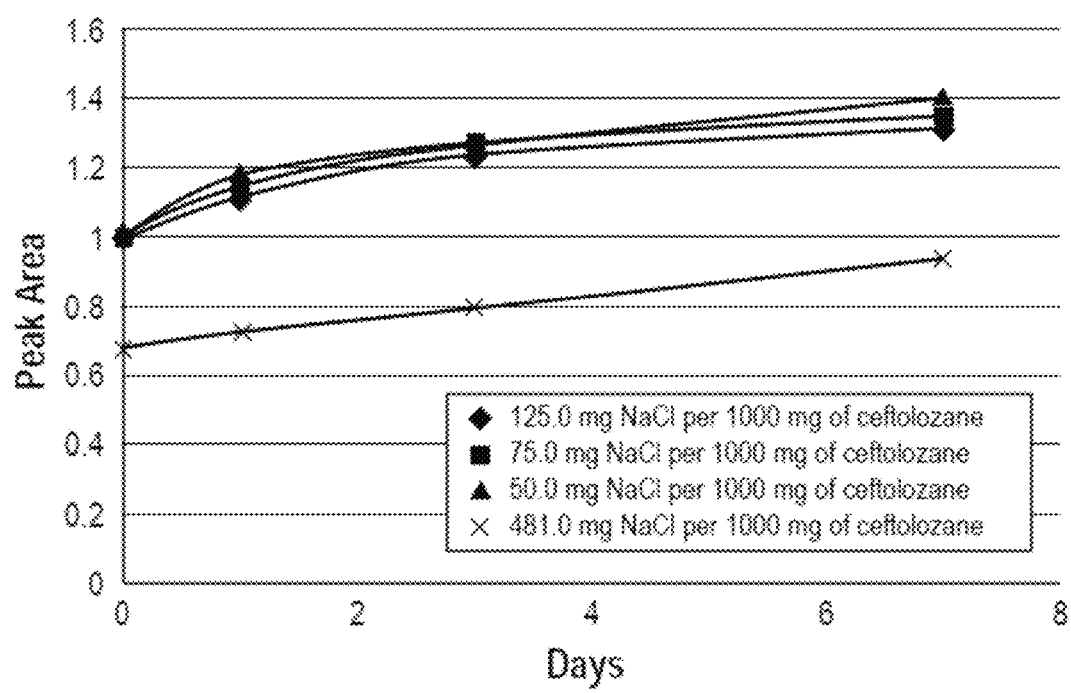
FIG. 10 is a plot of the data points from Table 20, showing the peak area of the composition peak 7 in CXA-201 compositions at 60° C. on day 0, day 1, day 3, and day 7, as measured by HPLC, wherein the CXA-201 compositions comprise ceftolozane, tazobactam, and sodium chloride.
Figure 11:
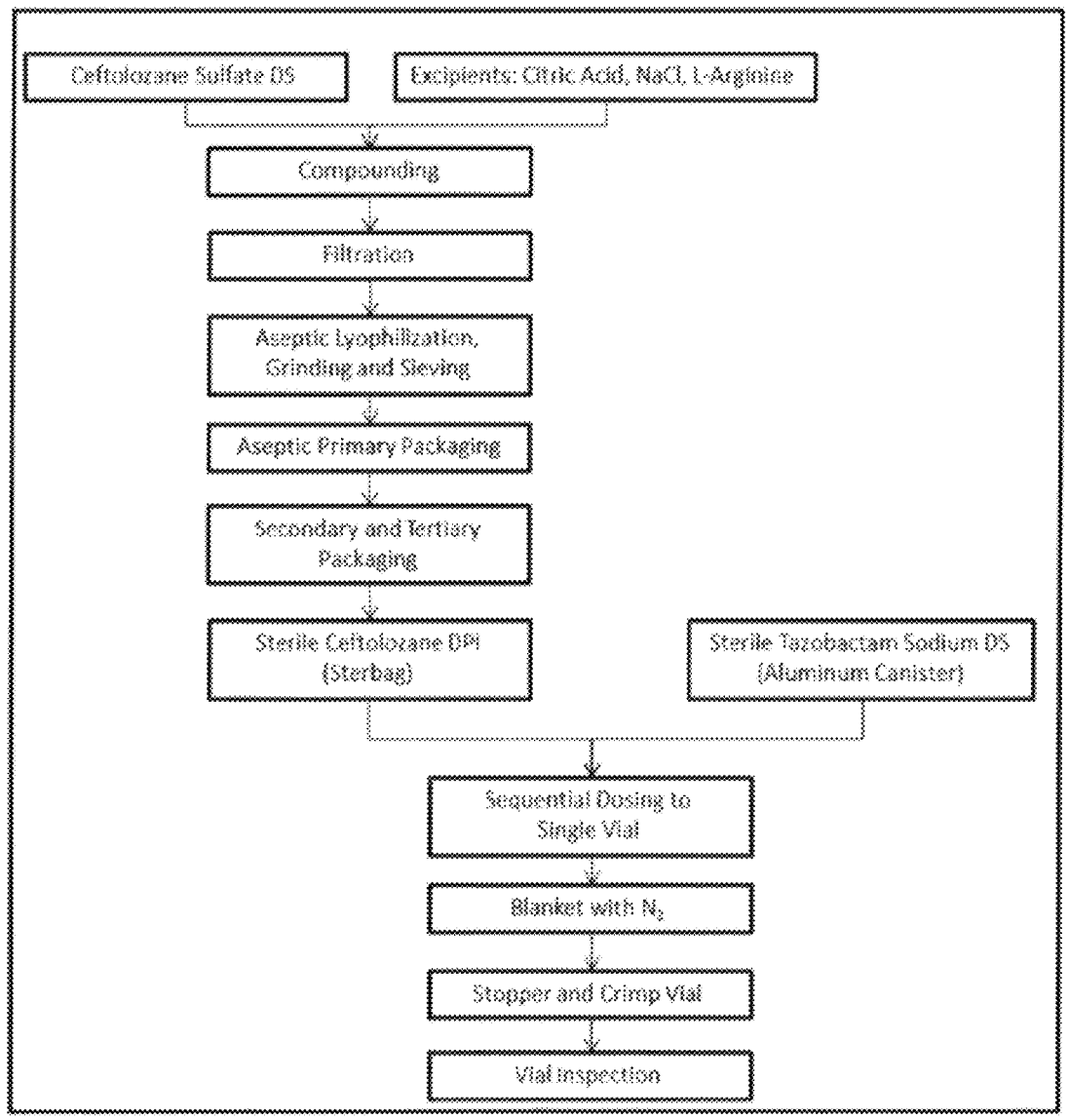
FIG. 11 is a flowchart showing the manufacturing process for a ceftolozane/tazobactam composition via co-filling.

The ceftolozane sodium-stabilized compositions having 125 mg or more sodium chloride relative to the fixed amount of 1,000 mg ceftolozane active also had lower quantities of additional substances identified by peaks 1 and 7 having characteristic retention times measured by HPLC (see Table 1, indicating retention times of about 0.1 for peak 1 and about 1.3 for peak 7 relative to ceftolozane measured according to the HPLC method of Example 1). In particular, these sodium chloride stabilized ceftolozane compositions were characterized by about 37-94% less of the material of peak 1 and about 38-306% less of the material of peak 7 (measured by corresponding HPLC peak areas) than comparable ceftolozane compositions having less than 125 mg sodium chloride (e.g., see 7-day stability study in Example 5). Referring to the data in Table 7 (FIG. 4), the amount of the composition of peak 1 (measured by HPLC according to Example 1) was measured by the % increase in the peak 1 HPLC peak during the 7-day stability test of Example 5.

In particular, samples containing 125 mg, 190 mg and 481 mg of sodium chloride per 1,000 mg of ceftolozane active showed at least a 37% reduction in the amount of the peak 1 composition observed for these formulations containing at least 125 mg sodium chloride per 1,000 mg ceftolozane active, compared to the compositions with 50 mg or 75 mg sodium chloride per 1,000 mg of ceftolozane active (e.g., the % increase in peak 1 for the sample containing 75 mg sodium chloride was about 37% greater than the comparable % decrease in ceftolozane for the sample containing 190 mg sodium chloride). In addition, compositions containing 125 mg, 190 mg and 481 mg of sodium chloride per 1,000 mg of ceftolozane active showed up to a 94% reduction in the amount of the peak 1 composition observed for these formulations containing at least 125 mg sodium chloride per 1,000 mg ceftolozane active, compared to the compositions with 50 mg or 75 mg sodium chloride per 1,000 mg of ceftolozane active (e.g., the % increase in peak 1 for the sample containing 50 mg sodium chloride was about 94% greater than the comparable % decrease in ceftolozane for the sample containing 481 mg sodium chloride).

The formulation of pharmaceutical compositions can be selected to minimize decomposition of the constituent drug substances and to produce a composition that is stable under a variety of storage conditions.

Provided herein are pharmaceutical compositions useful for the treatment of bacterial infections comprising ceftolozane and sodium chloride, wherein the sodium chloride is present in an amount sufficient to stabilize the ceftolozane. Also provided herein are pharmaceutical compositions comprising ceftolozane, tazobactam, and sodium chloride, wherein the sodium chloride is present in an amount sufficient to stabilize the ceftolozane. Advantageously, these pharmaceutical compositions have fewer additional compounds and are more chemically stable, and can therefore be stored for longer periods of time.

In one embodiment, provided herein is a pharmaceutical composition comprising ceftolozane and 125 mg sodium chloride per 1000 mg of ceftolozane, e.g., 125 to 500 mg sodium chloride per 1000 mg of ceftolozane, 200-500 mg sodium chloride per 1000 mg of ceftolozane, 300-500 mg sodium chloride per 1000 mg of ceftolozane, 400-500 mg sodium chloride per 1000 mg of ceftolozane, 450-500 mg sodium chloride per 1000 mg of ceftolozane, 460-500 mg sodium chloride per 1000 mg of ceftolozane, or about 476 mg sodium chloride per 1000 mg of ceftolozane, wherein the purity of the ceftolozane in the composition is 75% or greater after 3 days at 70° C. In another embodiment, provided herein is a pharmaceutical composition comprising ceftolozane and about 487 mg sodium chloride per 1000 mg of ceftolozane, wherein the purity of the ceftolozane in the composition is 75% or greater after 3 days at 70° C. In certain embodiments, the purity of the ceftolozane in the composition is 80% or greater, 85% or greater, 90% or greater, 95% or greater, 97% or greater, or 99% or greater after 3 days at 70° C.

In another embodiment, provided herein is a pharmaceutical composition comprising ceftolozane and 125 mg sodium chloride per 1000 mg of ceftolozane, e.g., 125 to 500 mg sodium chloride per 1000 mg of ceftolozane, 200-500 mg sodium chloride per 1000 mg of ceftolozane, 300-500 mg sodium chloride per 1000 mg of ceftolozane, 400-500 mg sodium chloride per 1000 mg of ceftolozane, 450-500 mg sodium chloride per 1000 mg of ceftolozane, 460-500 mg sodium chloride per 1000 mg of ceftolozane, or about 476 mg sodium chloride per 1000 mg of ceftolozane, wherein the purity of the ceftolozane in the composition is 94.8% or greater after 3 days at 60° C. In another embodiment, provided herein is a pharmaceutical composition comprising ceftolozane and about 487 mg sodium chloride per 1000 mg of ceftolozane, wherein the purity of the ceftolozane in the composition is 94.8% or greater after 3 days at 60° C. In certain embodiments, the purity of the ceftolozane in the composition is 95% or greater, 96% or greater, 97% or greater, 98% or greater, or 99% or greater after 3 days at 60° C.

In still another embodiment, provided herein is a pharmaceutical composition comprising ceftolozane and 125 mg sodium chloride per 1000 mg of ceftolozane, e.g., 125 to 500 mg sodium chloride per 1000 mg of ceftolozane, 200-500 mg sodium chloride per 1000 mg of ceftolozane, 300-500 mg sodium chloride per 1000 mg of ceftolozane, 400-500 mg sodium chloride per 1000 mg of ceftolozane, 450-500 mg sodium chloride per 1000 mg of ceftolozane, 460-500 mg sodium chloride per 1000 mg of ceftolozane, or about 476 mg sodium chloride per 1000 mg of ceftolozane, wherein the purity of the ceftolozane in the composition decreases by 3.1% or less after 3 days at 60° C. In another embodiment, provided herein is a pharmaceutical composition comprising ceftolozane and about 487 mg sodium chloride per 1000 mg of ceftolozane, wherein the purity of the ceftolozane in the composition decreases by 3.1% or less after 3 days at 60° C. In certain embodiments, the purity of the ceftolozane in the composition decreases by 3.0% or less, 2.5% or less, 2.0% or less, 1.5% or less, or 1% or less after 3 days at 60° C.

In another aspect, provided herein is a pharmaceutical composition comprising about 1,000 mg of ceftolozane active per 189 mg sodium from sodium chloride, and not more than 0.03% by high performance liquid chromatography (HPLC) of a RT63 Impurity at a retention time of about 63 minutes observed by HPLC using the method described in Example 1, the pharmaceutical composition obtained by a process comprising the step of lyophilizing an aqueous solution comprising 189 mg sodium from sodium chloride per 1,000 mg of ceftolozane active in the form of ceftolozane sulfate to obtain a lyophilized ceftolozane composition, and formulating the pharmaceutical composition from the lyophilized ceftolozane composition.

In one embodiment, the pharmaceutical composition comprises a total of 1,000 mg of ceftolozane active. In another aspect, provided herein is a pharmaceutical composition obtained by a process comprising the step of lyophilizing an aqueous solution comprising 189 mg sodium from sodium chloride per 1,000 mg of ceftolozane in the form of ceftolozane sulfate to obtain a lyophilized ceftolozane composition.

In one embodiment, the pH of the aqueous solution is 5.0 to 7.0, e.g., 6.0 to 7.0, and the aqueous solution further comprises L-arginine. In another embodiment, the pharmaceutical composition is formulated for parenteral administration and further comprises citric acid. In another embodiment, the composition is a unit dosage form in a container comprising tazobactam and 189 mg sodium from sodium chloride per 1,000 mg of ceftolozane active in the form of ceftolozane sulfate.

In another embodiment, the aqueous solution further comprises L-arginine and citric acid; the pH of the aqueous solution is 6.0 to 7.0 prior to lyophilization; and the pharmaceutical composition further comprises tazobactam blended with the lyophilized ceftolozane composition.

In still another aspect, provided herein is a container containing a unit dosage form of a pharmaceutical composition formulated for parenteral administration for the treatment of complicated intra-abdominal infections or complicated urinary tract infections, the pharmaceutical composition comprising 189 mg sodium from sodium chloride, and 1,000 mg ceftolozane active in the form of ceftolozane sulfate.

In one embodiment, the container comprises the ceftolozane sulfate, tazobactam and the sodium chloride and not more than 0.03% by high performance liquid chromatography (HPLC) of a RT63 Impurity at a retention time of about 63 minutes observed by HPLC using the method described in Example 1, i.e.:

| | |
|---|---|
| Column | Develosil ODS-UG-5, 5 µm, 250 × 4.6 mm |
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

Typically, antibiotic compositions do not contain sodium chloride or contain only a small amount of sodium chloride. For example, MAXIPIME®, which is approved for pneumonia, empiric therapy for febrile neutropenic patients, uncomplicated and complicated urinary tract infections, uncomplicated skin and skin structure infections, and complicated intra-abdominal infections, is a dry mixture of cefepime hydrochloride and L-arginine, wherein the mixture does not contain sodium chloride. CEFAZOLIN® for injection, which is approved for respiratory tract infections, urinary tract infections, skin and skin structure infections, biliary tract infections, bone and joint infections, genital infections, septicemia, and endocarditis and perioperative prophylaxis, comprises lyophilized cefazolin sodium that does not contain additional sodium salt. Furthermore, ROCEPHIN®, which is approved for lower respiratory tract infections, acute bacterial otitis media, skin and skin structure infections, urinary tract infections, uncomplicated gonorrhea, pelvic inflammatory disease, bacterial septicemia, bone and joint infections, intra-abdominal infections, meningitis, and surgical prophylaxis, comprises ceftriaxone sodium that only comprises 13.5 mg of free sodium per 1000 mg of ceftriaxone sodium, which equals about 34 mg sodium chloride per 1000 mg of ceftriaxone sodium if the free sodium is in sodium chloride form. In contrast, the pharmaceutical compositions provided herein (compositions comprising ceftolozane and sodium chloride, and compositions comprising ceftolozane, tazobactam, and sodium chloride), have high amounts of sodium chloride, e.g., 125-1000 mg sodium chloride per 1000 mg of ceftolozane.

Ceftolozane

The compound 5-amino-4-{[(2-aminoethyl)carbamoyl]amino}-2-{[(6R,7R)-7-({(2Z)-2-(5-amino-1,2,4-thiadiazol-3-yl)-2-[(1-carboxy-1-methylethoxy)imino]acetyl}amino)-2-carboxy-8-oxo-5-thia-1-azabicyclo[4.2.0]oct-2-en-3-yl]methyl}-1-methyl-1H-pyrazolium monosulfate (also known also as ceftolozane sulfate, FR264205, "CXA-101") is a cephalosporin compound (shown below), the synthesis of which is described in U.S. Pat. No. 7,129,232, wherein the compound is also named 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane has the chemical formula below and CAS registry number 689293-68-3. "Ceftolozane" can be provided as the salt, ceftolozane sulfate.

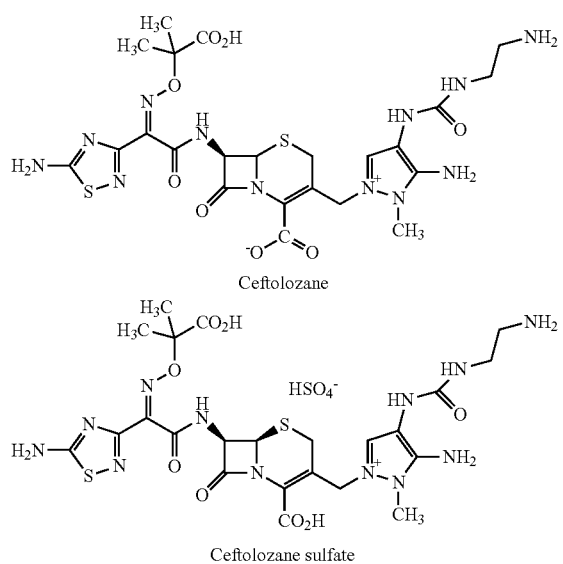

Ceftolozane

Ceftolozane sulfate

Unless otherwise indicated herein, the phrase "1000 mg ceftolozane" or "1 g ceftolozane" refers to an amount of ceftolozane containing the free base equivalent weight of ceftolozane provided in the free base form or any suitable salt form, as appropriate. For example, a composition containing 1000 mg of ceftolozane in the ceftolozane sulfate solid form will include greater than 1000 mg of material (e.g., due to at least the additional weight of the sulfate counter ion). Preferably, the ceftolozane is present as ceftolozane sulfate. If a ceftolozane sulfate composition contains "1000 mg of ceftolozane" then it includes an amount of ceftolozane sulfate comprising 1000 mg of the ceftolozane molecule in free base equivalent form. For example, as shown in Table 29, 1147 mg ceftolozane sulfate corresponds to 1000 mg of ceftolozane free base.

In another embodiment, "1000 mg ceftolozane" refers to an amount of ceftolozane that is considered a bioequivalent by the United States Food and Drug Administration (FDA), i.e. for which 90% CI of the relative mean Cmax, AUC(0-t) and AUC(0-∞) is within 80.00% to 125.00% of the reference formulation in the fasting state (see: "Guidance for Industry: Bioavailability and Bioequivalence Studies for Orally Administered Drug Products—General Considerations". Center for Drug Evaluation and Research, United States Food and Drug Administration, 2003).

"Ceftolozane active" refers to the active portion of a salt form of ceftolozane, i.e., the free base form of ceftolozane.

As used herein, "125 to 1000 mg sodium chloride per 1000 mg of ceftolozane" refers to a ratio of sodium chloride to ceftolozane free base equivalent. For example, "125 to 1000 mg sodium chloride per 1000 mg of ceftolozane" includes, for example, 62.5 to 500 mg sodium chloride per 500 mg of ceftolozane, as well as, for example, 25 to 200 mg sodium chloride per 200 mg ceftolozane, etc.

In another aspect, provided herein is a method for the treatment of bacterial infections in a mammal, comprising administering to said mammal a therapeutically effective amount of a pharmaceutical composition comprising ceftolozane as described herein.

II. Ceftolozane in the Presence of Tazobactam

It has also been observed that pharmaceutical compositions comprising ceftolozane, tazobactam, and 125 to 1000 mg sodium chloride per gram of ceftolozane exhibit better chemical stability and fewer additional compounds than those pharmaceutical compositions comprising ceftolozane and tazobactam, but less sodium chloride (see, e.g., Example 8). In particular embodiments described herein, the pharmaceutical compositions comprising ceftolozane, tazobactam, and 125 to 500 mg sodium chloride per 1000 mg of ceftolozane have been found to be more stable than the compositions comprising ceftolozane, tazobactam, and less than 125 mg sodium chloride per gram of ceftolozane.

Adding high amounts of sodium chloride to CXA-201 compositions (e.g., 125-1000 mg sodium chloride per 1000 mg of ceftolozane, 125-500 mg sodium chloride per 1000 mg of ceftolozane, 200-500 mg sodium chloride per 1000 mg of ceftolozane, 300-500 mg sodium chloride per 1000 mg of ceftolozane, 400-500 mg sodium chloride per 1000 mg of ceftolozane, 450-500 mg sodium chloride per 1000 mg of ceftolozane, 460-500 mg sodium chloride per 1000 mg of ceftolozane, or about 476 mg sodium chloride per 1000 mg of ceftolozane) also inhibits the formation of certain additional compounds. Adding about 487 mg sodium chloride per 1000 mg of ceftolozane to CXA-201 composition can also inhibit the formation of certain additional compounds. For example, in one experiment, CXA-201 compositions comprising 125-481 mg sodium chloride per 1000 mg ceftolozane developed a reduced amount of a composition having a retention time of 63 minutes ("RT 63") after three months at 25° C. (see the HPLC measurements shown in Example 8A).

Accordingly, in one aspect, provided herein is a pharmaceutical composition comprising ceftolozane, tazobactam, and 125-1000 mg sodium chloride per 1000 mg of ceftolozane, e.g., 125-500 mg sodium chloride per 1000 mg of ceftolozane, 200-500 mg sodium chloride per 1000 mg of ceftolozane, 300-500 mg sodium chloride per 1000 mg of ceftolozane, 400-500 mg sodium chloride per 1000 mg of ceftolozane, 450-500 mg sodium chloride per 1000 mg of ceftolozane, 460-500 mg sodium chloride per 1000 mg of ceftolozane, or about 476 mg sodium chloride per 1000 mg of ceftolozane. In another embodiment, provided herein is a pharmaceutical composition comprising ceftolozane, tazobactam, and about 487 mg sodium chloride per 1000 mg of ceftolozane.

In another embodiment, provided herein is a pharmaceutical composition comprising ceftolozane, tazobactam, and 125-1000 mg sodium chloride per 1000 mg of ceftolozane, e.g., 125-500 mg sodium chloride per 1000 mg of ceftolozane, 200-500 mg sodium chloride per 1000 mg of ceftolozane, 300-500 mg sodium chloride per 1000 mg of ceftolozane, 400-500 mg sodium chloride per 1000 mg of ceftolozane, 450-500 mg sodium chloride per 1000 mg of ceftolozane, 460-500 mg sodium chloride per 1000 mg of ceftolozane, or about 476 mg sodium chloride per 1000 mg of ceftolozane, wherein the purity of the ceftolozane in the composition is 94.9% or greater after 3 days at 60° C. In another embodiment, provided herein is a pharmaceutical composition comprising ceftolozane, tazobactam, and about 487 mg sodium chloride per 1000 mg of ceftolozane, wherein the purity of the ceftolozane in the composition is 94.9% or greater after 3 days at 60° C. In certain embodiments, the purity of the ceftolozane in the composition is 95% or greater, 96% or greater, 97% or greater, 98% or greater, or 99% or greater after 3 days at 60° C.

Tazobactam

The compound (2S,3S,5R)-3-methyl-7-oxo-3-(1H-1,2,3-triazol-1-ylmethyl)-4-thia-1-azabicyclo[3.2.0]heptane-2-carboxylic acid 4,4-dioxide (also known as tazobactam) is a β-lactamase inhibitor of the following structure:

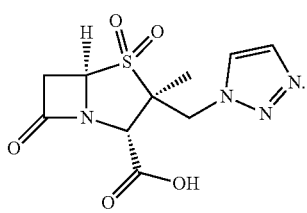 [SMILES: C[C@]1(Cn2ccnn2)[C@H](C(=O)O)N2C(=O)C[C@H]2S1(=O)=O]

As used herein, tazobactam can be a free acid, a sodium salt, an arginine salt, or a hydrate or solvate thereof. The phrases "250-750 mg tazobactam", "250-700 mg tazobactam," "300-700 mg tazobactam", "300-650 mg tazobactam", "350-650 mg tazobactam", "350-600 mg tazobactam", "400-600 mg tazobactam", "400-550 mg tazobactam", "450-550 mg tazobactam" or "about 500 mg tazobactam" refer to an amount of tazobactam containing the free acid equivalent weight of tazobactam provided in the free acid form or any suitable salt form. For example, a composition containing 500 mg of tazobactam in the tazobactam sodium solid form will include greater than 500 mg of material (e.g., due to at least the additional weight of the sodium counter ion). For example, as shown in Table 29, 537 mg tazobactam sodium corresponds to 500 mg of tazobactam free acid. Preferably, the tazobactam is present as tazobactam sodium. If a tazobactam sodium composition contains "500 mg of tazobactam" then it includes an amount of tazobactam sodium comprising 500 mg of the tazobactam molecule in free acid equivalent form.

In an embodiment, the tazobactam is tazobactam sodium sterile powder. In yet a further embodiment, the tazobactam sodium sterile powder is generated by neutralizing tazobactam acid with sodium bicarbonate followed by lyophilization.

As used herein, the term "tazobactam active" refers to the active portion of a salt form of tazobactam, i.e., tazobactam free acid.

In certain embodiments, the pharmaceutical compositions further comprise tazobactam sodium at a quantity equivalent of 500 mg of tazobactam free acid in a lyophilized powder form per 1000 mg of ceftolozane (anhydrous, free base equivalent).

III. Liquid Pharmaceutical Compositions or Formulations

In another aspect, provided herein is a liquid pharmaceutical composition (e.g., an intravenous infusion solution) comprising ceftolozane and tazobactam, wherein the composition is suitable for intravenous administration. In one embodiment, the composition further comprises 125-1000 mg sodium chloride per 1000 mg of ceftolozane. In another embodiment, the composition further comprises 125-500 mg sodium chloride per 1000 mg of ceftolozane. In an embodiment, the liquid pharmaceutical composition (e.g., an intravenous infusion solution) is prepared by reconstitution of a ceftolozane and tazobactam composition with sterile water and/or normal sterile saline, followed by dilution with sterile water and/or normal sterile saline. In an embodiment, the liquid pharmaceutical composition (e.g., an intravenous infusion solution) is prepared by reconstitution of a ceftolozane and tazobactam composition with normal sterile saline, followed by dilution with normal sterile saline. In another embodiment, the liquid pharmaceutical composition (e.g., an intravenous infusion solution) has an osmolality between about 300 mOsm/kg and 900 mOsm/kg, including injectable formulations with an osmolality of 350-900 mOsm/kg to 350-800 mOsm/kg, 400-500 mOsm/kg and 500-600 mOsm/kg. In a further embodiment, the liquid pharmaceutical composition (e.g., an intravenous infusion solution) comprising 1,000 mg ceftolozane active and 500 mg of tazobactam active (as pharmaceutically acceptable salts thereof) has an osmolality that is between about 400 mOsm/kg and 500 mOsm/kg (e.g., 446-478 mOsm/kg, 440-480 mOsm/kg, 420-490 mOsm/kg). In a further embodiment, the liquid pharmaceutical composition (e.g., an intravenous infusion solution) comprising 2,000 mg ceftolozane active and 1000 mg of tazobactam active (as pharmaceutically acceptable salts thereof) has an osmolality that is between about 500 mOsm/kg and 650 mOsm/kg. In yet a further embodiment, the liquid pharmaceutical composition (e.g., an intravenous infusion solution) has an osmolality that is less than about 600 mOsm/kg (e.g., 290-610 mOsm/kg, 350-605 mOsm/kg, 550-605 mOsm/kg, 589-604 mOsm/kg). In another embodiment, the ceftolozane and tazobactam of the liquid pharmaceutical composition (e.g., an intravenous infusion solution) are controlled to pH 5 to 7. In a further embodiment, the ceftolozane and tazobactam of the liquid pharmaceutical composition (e.g., an intravenous infusion solution) are controlled to about pH 6.

In one embodiment, the methods further comprise reconstituting the lyophilized mixture in an aqueous solvent, such that the resulting solution is suitable for infusion. The mixture can be reconstituted in saline and/or sterile water for injection.

Methods of Preparing Pharmaceutical Compositions Comprising Ceftolozane and Sodium Chloride Pharmaceutical compositions comprising ceftolozane and stabilizing-effective amount of a stabilizing agent can be obtained by lyophilization. As is known to those skilled in the art, lyophilization is a process of freeze-drying in which water is sublimed from a frozen solution of one or more solutes. Specific methods of lyophilization are described in Remington's Pharmaceutical Sciences, Chapter 84, page 1565, Eighteenth Edition, A. R. Gennaro, (Mack Publishing Co., Easton, Pa., 1990). A pharmaceutical composition comprising ceftolozane can be prepared by adding a stabilizing amount of sodium chloride in a fixed ratio to ceftolozane in an aqueous solution prior to lyophilization, then lyophilizing the solution to obtain a lyophilized composition comprising sodium chloride and ceftolozane.

In particular, the pharmaceutical antibiotic compositions can include stabilized ceftolozane sulfate obtained by a process comprising the steps of lyophilizing an aqueous solution containing ceftolozane and a stabilizing-effective amount of a stabilizing agent, where the stabilizing-effective amount of the stabilizing agent is about 100 to 500 mg (preferably 300-500 mg) of the stabilizing agent per 1,000 mg ceftolozane active in the aqueous solution prior to lyophilization. A therapeutically effective amount of ceftolozane (e.g., ceftolozane sulfate) and a stabilizing-effective amount of the stabilizing agent can dissolved in an aqueous solution that can be lyophilized to obtain a stabilized ceftolozane pharmaceutical composition.

The method can further comprise the steps of: (1) forming a solution comprising sodium chloride and ceftolozane or a salt thereof followed by lyophilizing the solution; and (2) combining the lyophilized ceftolozane with other components (e.g., a β-lactamase inhibitor, such as tazobactam, or a lyophilized β-lactamase inhibitor, such as a lyophilized tazobactam) to obtain the pharmaceutical composition. The resulting pharmaceutical composition can be a powder for reconstitution to obtain an injectable pharmaceutical composition that can be intravenously administered to a patient. In yet a further embodiment, the method comprises adding 189 mg sodium from sodium chloride per 1000 mg of ceftolozane active in an aqueous solution, then lyophilizing the solution to obtain a lyophilized material comprising sodium chloride and ceftolozane sulfate in a ratio effective to provide a product with less than 0.03% of the RT63 Impurity as detected by the HPLC method of Example 1, i.e.:

| Column | Develosil ODS-UG-5, 5 µm, 250 × 4.6 mm |
|---|---|
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

A. Blending

In other embodiments, pharmaceutical compositions comprising ceftolozane can be obtained by methods that include the steps of: (1) adding a stabilizing amount of sodium chloride to ceftolozane optionally followed by co-lyophilizing or spray drying the ceftolozane and sodium chloride; and (2) combining the product of step (1) with other components. For example, the product of step (1) can be combined with a β-lactamase inhibitor, such as tazobactam (CAS#: 89786-04-9), avibactam (CAS#1192500-31-4), Sulbactam (CAS#68373-14-8) and/or clavulanate (CAS#58001-44-8). The beta lactamase inhibitor can be included in a crystalline or amorpous form, such as a lyophilized tazobactam or crystalline tazobactam (e.g., U.S. Pat. Nos. 8,476,425 and 5,763,603) to obtain the pharmaceutical composition.

Pharmaceutical compositions comprising ceftolozane and tazobactam with reduced or even undetable levels of the compound of RRT 1.22 (e.g., including levels of RRT 1.22 that are not detectable by HPLC according to Example 1 and/or comprise less than 0.15%, 0.10%, 0.05% or 0.03% by weight; or from 0.03-0.05%, 0.03-0.1% or 0.03-0.15% by HPLC according to Example 1) can be obtained by blending a first composition comprising a therapeutically effective amount of ceftolozane in the absence of tazobactam with a second composition comprising a therapeutically effective amount of tazobactam in the absence of ceftolozane to form a blended pharmaceutical composition.

Without being bound by theory, the compound RRT 1.22 can be formed by a reaction between ceftolozane and formylacetic acid, a by-product of tazobactam as illustrated in Marunaka et al. (Chem. Pharm. Bull. 1988, Vol. 36 (11), pp. 4478-4487.

FIG. 1 is a flowchart showing the steps for preparing a CXA-201 composition comprising ceftolozane (referred to as CXA-101) and tazobactam using a blending process, wherein the ceftolozane and tazobactam are lyophilized separately prior to blending as described herein.

The (first) ceftolozane composition can be prepared in the absence of tazobactam by forming a first aqueous solution comprising ceftolozane sulfate and other components including excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust pH of the aqueous solution (e.g., to pH 6-7) and to increase the solubility of ceftolozane; and citric acid is used to prevent discoloration of the product, due to its ability to chelate metal ions. Preferably, the first aqueous solution comprises about 125 mg-500 mg sodium chloride per 1,000 mg of ceftolozane active. The ceftolozane can be included as an amount of ceftolozane sulfate of formula (I) containing at least about 1,000 mg ceftolozane active. The (first) aqueous solution is then lyophilized to form a first lyophilized ceftolozane composition, which is combined with tazobactam, e.g., the lyophilized tazobactam (e.g., lyophilized tazobactam sodium) or crystalline tazobactam.

The (second) tazobactam composition can be prepared in the absence of ceftolozane by forming a second solution comprising tazobactam. The tazobactam can be included in an amount providing about 500 mg of tazobactam active per 1,000 mg ceftolozane active (i.e., a 1:2 weight ratio of tazobactam active to ceftolozane active). Unless otherwise indicated, tazobactam can be a free acid, a sodium salt, an arginine salt, or a hydrate or solvate thereof. In one embodiment, the tazobactam in the (second) tazobactam composition is tazobactam acid and the second composition further comprises sodium bicarbonate or sodium hydroxide. Lyophilizing tazobactam in the presence of sodium bicarbonate or sodium hydroxide forms a lyophilized tazobactam sodium, which can then be further blended with the (first) lyophilized ceftolozane composition.

Pharmaceutical compositions with reduced or undetectable amounts of the compound of RRT 1.22 can be obtained by lyophilizing ceftolozane without formylacetic acid and/or tazobactam under conditions that prevent formation of RRT 1.22 (e.g., Example 9). The presence of RRT 1.22 can be detected by HPLC (e.g., Examples 1 and 7). Specific methods of lyophilization are described in Remington's Pharmaceutical Sciences, Chapter 84, page 1565, Eighteenth Edition, A. R. Gennaro, (Mack Publishing Co., Easton, Pa., 1990). The formation of the compound of formula (III) can be avoided by preventing the reaction of ceftolozane and formylacetic acid. In one embodiment, the compound of formula (III) can be suppressed by separately lyophlizing ceftolozane sulfate and tazobactam in separate solutions, and then blending the lyophilized compositions to form a pharmaceutical composition.

In one aspect, antibiotic pharmaceutical compositions comprising ceftolozane and tazobactam with less than about 0.15%, 0.10%, 0.05% or 0.03% by weight; or from 0.03-0.05%, 0.03-0.1% or 0.03-0.15% by HPLC of the compound of formula (III) are obtained by a process comprising the steps of: (a) lyophilizing ceftolozane in the absence of tazobactam to obtain a lyophilized ceftolozane composition, and (b) blending the lyophilized ceftolozane composition with a composition comprising tazobactam under conditions suitable for attaining the aforementioned purity levels, e.g., by blending with crystalline tazobactam or lyophilized tazobactam.

In another aspect, antibiotic pharmaceutical compositions comprising ceftolozane and tazobactam and less than about 0.15%, 0.10%, 0.05% or 0.03% by weight; or from 0.03-0.05%, 0.03-0.1% or 0.03-0.15% by HPLC of the compound of formula (III) are obtained by a process comprising the steps of: (a) lyophilizing tazobactam in the absence of ceftolozane to obtain a lyophilized tazobactam composition, and (b) blending the lyophilized tazobactam composition with a composition comprising ceftolozane (e.g., lyophilized ceftolozane sulfate).

In a third aspect, antibiotic pharmaceutical compositions comprising ceftolozane and tazobactam and less than about 0.15%, 0.10%, 0.05% or 0.03% by weight; or from 0.03-0.05%, 0.03-0.1% or 0.03-0.15% by HPLC of the compound of formula (III) are obtained by a process comprising the steps of: (a) lyophilizing tazobactam in the absence of ceftolozane to obtain a lyophilized tazobactam composition, (b) lyophilizing ceftolozane in the absence of tazobactam to obtain a lyophilized ceftolozane composition, and (c) blending the lyophilized tazobactam composition with the lyophilized ceftolozane composition.

Pharmaceutical compositions comprising the compound of formula (III), ceftolozane and tazobactam can be formulated to treat infections by parenteral administration (including subcutaneous, intramuscular, and intravenous) administration. Pharmaceutical compositions may additionally comprise excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust pH and to increase the solubility of ceftolozane; and citric acid is used to prevent discoloration of the product, due to its ability to chelate metal ions. In one particular embodiment, the pharmaceutical compositions described herein are formulated for administration by intravenous injection or infusion.

Other pharmaceutical antibiotic compositions can include ceftolozane sulfate and the compound of formula (III). For example, pharmaceutical compositions comprising 0.13%, 0.15%, 0.30%, 0.38%, 0.74% or 0.97% of the compound of formula (III) are herein. The pharmaceutical antibiotic compositions can be provided in a unit dosage form (e.g., in a container). The unit dosage form can be dissolved with a pharmaceutically acceptable carrier, and then intravenously administered. The unit dosage form comprises 1000 mg of ceftolozane active and 500 mg tazobactam, typically 1000 mg ceftolozane active as ceftolozane sulfate and 500 mg of tazobactam active as tazobactam sodium, argininate or free acid. The unit dosage forms are commonly stored in containers.

In another aspect, provided herein is a unit dosage form of a pharmaceutical composition comprising 1,000 mg ceftolozane and 500 mg tazobactam, the pharmaceutical composition formulated for parenteral administration for the treatment of complicated intra-abdominal infections or complicated urinary tract infections, the pharmaceutical composition comprising ceftolozane sulfate and tazobactam, obtained by a process comprising the steps of: lyophlizing an aqueous solution to obtain a lyophilized ceftolozane composition, wherein the aqueous solution comprises water, ceftolozane sulfate, 125-500 mg sodium chloride per 1,000 mg ceftolozane active in the aqueous solution, an amount of L-arginine to provide a pH of 6-7 in the solution prior to lyophilization; and blending the lyophilized ceftolozane composition with a lyophilized tazobactam composition in an amount providing the ratio of about 500 mg tazobactam free acid per 1,000 mg of ceftolozane active to obtain the unit dosage form.

Another embodiment of the invention is a container containing a unit dosage form of a pharmaceutical composition formulated for parenteral administration for the treatment of complicated intra-abdominal infections or complicated urinary tract infections. The container can be obtained by a process comprising the steps of: a) lyophilizing an aqueous solution comprising 189 mg sodium from sodium chloride per 1000 mg ceftolozane active in the form of ceftolozane sulfate and further comprising citric acid, and L-arginine to obtain a lyophilized ceftolozane composition; and b) filling a sufficient quantity of the lyophilized composition into a container to obtain a unit dosage form comprising 189 mg sodium from sodium chloride and 1,000 mg of ceftolozane active in the form of ceftolozane sulfate. In one aspect, the pH of the aqueous solution is 6.0 to 7.0. In another aspect the pharmaceutical composition is formulated for parenteral administration by reconstituting the pharmaceutical composition in the container (e.g., with 10 mL of diluent such as water for injection or isotonic saline) followed by addition of the reconstituted pharmaceutical composition to a carrier for injection (e.g., about 100 mL of isotonic saline or other pharmaceutically acceptable carrier for intravenous administration). Optionally, the container is also filled with tazobactam (e.g., a lyophilized tazobactam such as tazobactam sodium). In yet another aspect, the pharmaceutical composition is a liquid composition comprising 189 mg sodium from sodium chloride, 1,000 mg of ceftolozane active and tazobactam in an amount providing about 500 mg tazobactam acid equivalent per 1,000 mg of ceftolozane active, formulated for parenteral administration and the pH of the aqueous solution is 6.0 to 7.0.

The pharmaceutical composition in the container can also be a Ceftolozane/Tazobactam for Injection Drug Product, 1000 mg/500 mg. It is presented as a combination of two sterile active powders in a single container intended for reconstitution and intravenous infusion. In an embodiment, the drug product is prepared by converting ceftolozane sulfate to a sterile drug product intermediate (composition) powder with excipients citric acid, sodium chloride and L-arginine. This can be done by lyophilization, as described herein. Tazobactam sodium drug substance can be presented as a sterile powder without any excipients. The tazobactam sodium drug substance can be lyophilized, spray dried or provided as a crystalline material. The drug product is then prepared by aseptically filling the two powders (e.g., the two separately lyophilized drug powders) sequentially into a single container.

In an embodiment, the container of ceftolozane/tazobactam for injection contains approximately 2255 mg ceftolozane sterile composition powder that contains 1147 mg ceftolozane sulfate, which is equivalent to 1000 mg ceftolozane free base, as well as approximately 537 mg tazobactam sodium sterile drug substance, equivalent to 500 mg tazobactam free acid. At the time of administration, the container is reconstituted with 10 mL vehicle, sterile 5% Dextrose Injection USP, Water for Injection or 0.9% Sodium Chloride Injection USP, then the container contents further diluted in an infusion bag of 0.9% Sodium Chloride Injection USP or 5% Dextrose Injection USP, for administration. The constituents are shown in Table 29.

A pharmaceutical composition can include ceftolozane sulfate and tazobactam in an amount providing 1,000 mg of ceftolozane active per 500 mg of tazobactam active, and 0.03% to 0.15% by HPLC of a compound of formula (III) detectable at a retention time relative to ceftolozane of 1.22 by high performance liquid chromatography using the method described in Example 1. Optionally, the pharmaceutical composition can further include 125 mg to 500 mg of sodium chloride per 1,000 mg of ceftolozane active, and L-arginine. The tazobactam in the composition can be tazobactam sodium.

In one embodiment of these methods of preparing, 125-500 mg sodium chloride per 1000 mg of ceftolozane is combined. In another embodiment of these methods of preparing, the amount of the sodium chloride combined is 200-500 mg sodium chloride per 1000 mg of ceftolozane, 300-500 mg sodium chloride per 1000 mg of ceftolozane, 400-500 mg sodium chloride per 1000 mg of ceftolozane, 450-500 mg sodium chloride per 1000 mg of ceftolozane, 460-500 mg sodium chloride per 1000 mg of ceftolozane, or about 476 mg sodium chloride per 1000 mg of ceftolozane. In another embodiment of these methods of preparing, the amount of the sodium chloride combined is about 487 mg sodium chloride per 1000 mg of ceftolozane.

In another embodiment of these methods of preparing, the method further comprises lyophilizing the ceftolozane in the absence of the tazobactam. In yet another embodiment, the method can further comprise lyophilizing the tazobactam in the absence of the ceftolozane.

Accordingly, in one aspect, provided herein is a pharmaceutical composition comprising ceftolozane and tazobactam, wherein the composition comprises less than 0.5%, 0.4%, 0.3%, 0.25%, 0.2%, 0.15%, 0.1%, or 0.05% by weight of the compound RRT 1.22. In another aspect, provided herein is a pharmaceutical composition comprising ceftolozane and tazobactam, wherein the composition comprises less than 0.1% by weight of the compound RRT 1.22. In one embodiment, the pharmaceutical composition comprises less than 0.05% by weight of the compound RRT 1.22. In another embodiment, the pharmaceutical composition comprises less than 0.15% by weight of the compound RRT 1.22. In yet another embodiment, the pharmaceutical composition comprises no detectable amount of the compound RRT 1.22 as measured by HPLC.

In contrast, a greater amount of compound RRT 1.22 was found in compositions of ceftolozane and tazobactam, wherein the compositions were formed through co-lyophilization, i.e., the ceftolozane and tazobactam were combined and co-lyophilized together (see, e.g., Examples 6, 7a, and 7b), as opposed to being individually lyophilized and blended together (see, e.g., Examples 9 and 10).

In one aspect, provided herein is an antibacterial pharmaceutical composition comprising ceftolozane sulfate and tazobactam in a ratio of 1,000 mg ceftolozane active per 500 mg of tazobactam active, the pharmaceutical composition obtained by a process comprising the steps of: lyophilizing a first aqueous solution in the absence of tazobactam, the first aqueous solution comprising ceftolozane sulfate prior to lyophilization to obtain a first lyophilized ceftolozane composition; and blending the first lyophilized ceftolozane composition with tazobactam to obtain an antibacterial composition comprising less than 0.13% by HPLC of a compound of formula (III) (compound RRT 1.22) detectable at a retention time relative to ceftolozane of 1.22 by high performance liquid chromatography using the method described in Example 1, i.e.:

| Column | Develosil ODS-UG-5, 5 µm, 250 × 4.6 mm |
|---|---|
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

In one embodiment, the antibacterial composition comprises less than 0.03% of the compound of formula (III) detected by HPLC. In another embodiment, the first aqueous solution further comprises L-arginine in an amount effective to adjust the pH of the first aqueous solution to 6-7 prior to lyophilization to obtain a first lyophilized ceftolozane composition.

In another embodiment, the antibacterial pharmaceutical composition is obtained by a process further comprising the steps of: lyophilizing a second solution comprising tazobactam in the absence of ceftolozane to form a second lyophilized tazobactam composition; and blending the first lyophilized ceftolozane composition and the second lyophilized tazobactam composition to obtain the antibacterial composition.

In another embodiment, the tazobactam in the second solution is tazobactam acid, and wherein the tazobactam acid in the second solution is lyophilized in the presence of sodium bicarbonate to form the second lyophilized tazobactam solution.

In another embodiment, the first aqueous solution comprises L-arginine in an amount effective to provide a pH of about 5-7, e.g., 6-7. In another embodiment, the first aqueous solution comprises 125 mg to 500 mg of sodium chloride per 1,000 mg of ceftolozane active.

In another embodiment, the first aqueous solution further comprises citric acid. In another embodiment, the first aqueous solution consists of ceftolozane sulfate, citric acid, sodium chloride, L-arginine, and water.

In another aspect, provided herein is a unit dosage form of a pharmaceutical composition formulated for parenteral administration for the treatment of complicated intra-abdominal infections or complicated urinary tract infections, the pharmaceutical composition comprising ceftolozane sulfate and tazobactam in a ratio of 1,000 mg ceftolozane active per 500 mg of tazobactam active, the pharmaceutical composition obtained by a process comprising the steps of: lyophilizing a first aqueous solution in the absence of tazobactam, the first aqueous solution comprising ceftolozane sulfate, 125 mg to 500 mg of sodium chloride per 1,000 mg of ceftolozane active, at a pH of 6-7 prior to lyophilization to obtain a first lyophilized ceftolozane composition; lyophilizing a second solution comprising tazobactam in the absence of ceftolozane to form a second lyophilized tazobactam composition; and blending the first lyophilized ceftolozane composition and the second lyophilized tazobactam composition to obtain the antibacterial composition.

In another embodiment, the unit dosage form comprises a total of not more than 0.03% by HPLC of a compound of formula (III) detectable at a retention time relative to ceftolozane of 1.22 by high performance liquid chromatography using the method described in Example 1, i.e.:

| Column | Develosil ODS-UG-5, 5 µm, 250 × 4.6 mm |
|---|---|
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

| | Time (min.) | % A | % B |
|---|---|---|---|
| Gradient Profile | 0 | 75 | 25 |
| | 30 | 70 | 30 |
| | 60 | 0 | 100 |
| | 85 | 0 | 100 |
| | 85.1 | 75 | 25 |
| | 110 | 75 | 25 | to detect:

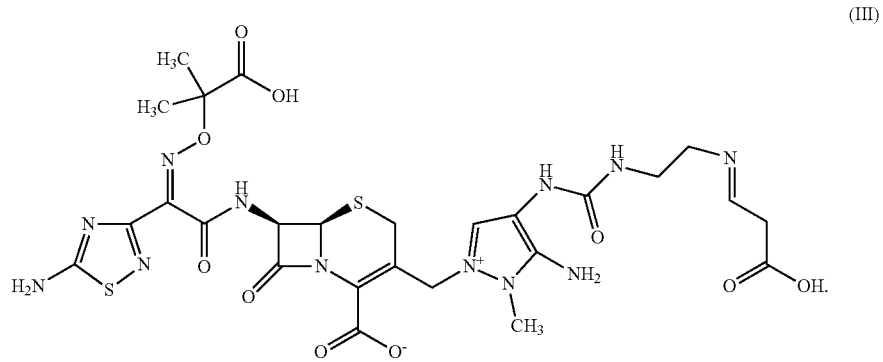 [SMILES: Cn1c(N)c(NC(=O)NCC/N=C/CC(=O)O)c[n+]1CC1=C(C(=O)[O-])N2C(=O)[C@@H](NC(=O)/C(=N\OC(C)(C)C(=O)O)c3nsc(N)n3)[C@H]2SC1]

(III)

In another embodiment, the unit dosage form comprises a total of 1,000 mg of ceftolozane active and a total of 500 mg of tazobactam active.

In another embodiment, the unit dosage form comprises a total of not more than 0.03% by HPLC of a compound of formula (III) detectable at a retention time relative to ceftolozane of 1.22 by high performance liquid chromatography using the method described in Example 1, i.e.:

| Column | Develosil ODS-UG-5, 5 µm, 250 × 4.6 mm |
|---|---|
| Column temperature | 45° C. ± 2° C. |
| Wavelength: | 254 nm for ceftolozane and ceftolozane-related substances in Table 1A |
| Mobile phase A | 50 mM Sodium Perchlorate Monohydrate in water, adjusted to pH 2.5 with Diluted Perchloric Acid |
| Mobile phase B | 63 mM Sodium Perchlorate Monohydrate in water, adjusted to pH 2.5 with Diluted Perchloric Acid:Acetonitrile, 4:1 (v/v) |

|  | Time (min.) | % A | % B |
|---|---|---|---|
| Gradient Profile | 0 | 75 | 25 |
|  | 30 | 70 | 30 |
|  | 60 | 0 | 100 |
|  | 85 | 0 | 100 |
|  | 85.1 | 75 | 25 |
|  | 110 | 75 | 25 | to detect:

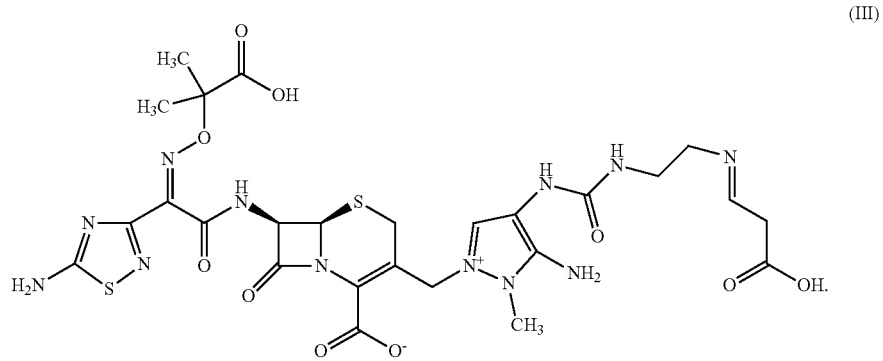 [SMILES: Cn1c(N)c(NC(=O)NCC/N=C/CC(=O)O)c[n+]1CC1=C(C(=O)[O-])N2C(=O)[C@@H](NC(=O)/C(=N\OC(C)(C)C(=O)O)c3nsc(N)n3)[C@H]2SC1]

(III)

In another aspect, provided herein is a compound of formula (III):

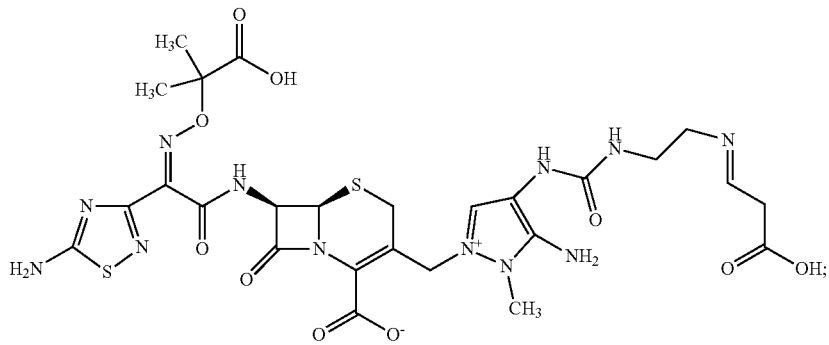

(III)

or a pharmaceutically acceptable salt thereof.

In still another aspect, provided herein is a pharmaceutical composition comprising a compound of formula (III):

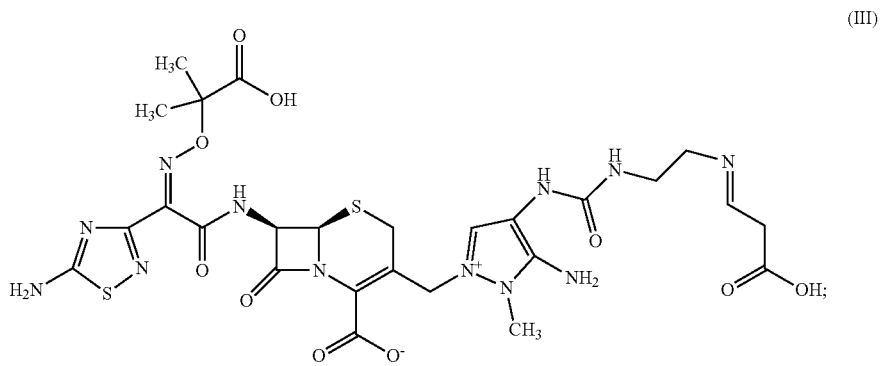 [SMILES: Cn1c(N)c(NC(=O)NCC/N=C/CC(=O)O)c[n+]1CC1=C(C(=O)[O-])N2C(=O)[C@@H](NC(=O)/C(=N\OC(C)(C)C(=O)O)c3nsc(N)n3)[C@H]2SC1]

(III)

or a pharmaceutically acceptable salt thereof.

In one embodiment, the pharmaceutical composition further comprises ceftolozane sulfate. In another embodiment, the pharmaceutical composition further comprises tazobactam.

In another embodiment, the compound of formula (III) is obtained by a process comprising the step of reacting ceftolozane and formylacetic acid to obtain the compound of formula (III). In another embodiment, the compound of formula (III) is obtained by a process comprising the step of reacting ceftolozane and tazobactam acid to obtain the compound of formula (III).

In another embodiment, the compound of formula (III) is obtained by a process comprising the steps of: forming an aqueous solution comprising ceftolozane and tazobactam acid; and lyophilizing the aqueous solution to obtain a lyophilized composition comprising the compound of formula (III). In another embodiment, the aqueous solution comprises ceftolozane sulfate and tazobactam acid in a 2:1 weight ratio between the amount of ceftolozane active and the amount of tazobactam acid. In another embodiment, the aqueous solution comprises sodium chloride, ceftolozane sulfate, tazobactam acid and L-arginine.

In another embodiment, the aqueous solution has a pH of about 5.0 to 7.0, e.g., 6.0 to 7.0. In another embodiment, the pharmaceutical composition is formulated for parenteral administration. In another embodiment, the compound of formula (III) is obtained by a process further comprising the step of performing high performance liquid chromatography (HPLC) on the lyophilized composition to isolate the compound of formula (III).

In another embodiment, the pharmaceutical composition comprises about 0.13-0.97% of the compound of formula (III). In another embodiment, the pharmaceutical composition comprises up to about 0.15% of the compound of formula (III). In another aspect, provided herein is a pharmaceutical composition comprising a compound of formula (III),

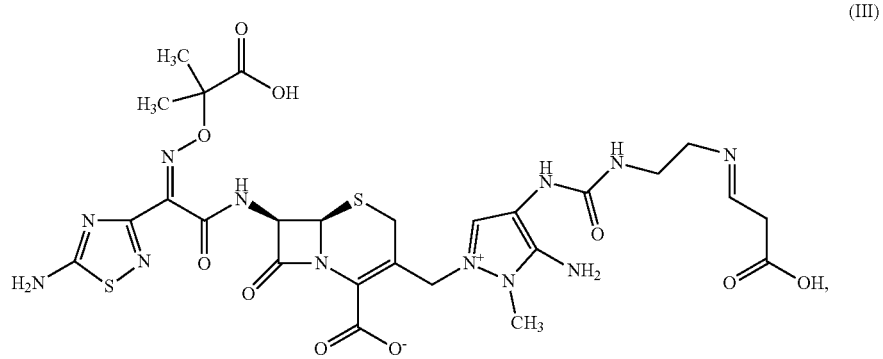 [SMILES: Cn1c(N)c(NC(=O)NCC/N=C/CC(=O)O)c[n+]1CC1=C(C(=O)[O-])N2C(=O)[C@@H](NC(=O)/C(=N\OC(C)(C)C(=O)O)c3nsc(N)n3)[C@H]2SC1]

(III)

the compound of formula (III) obtained by a process comprising the steps of: forming an aqueous solution comprising tazobactam acid and ceftolozane sulfate in an amount providing 1,000 mg of ceftolozane active per 500 mg of tazobactam acid in the aqueous solution; lyophilizing the aqueous solution of step (a) to obtain a lyophilized composition comprising a compound of formula (III); and formulating the lyophilized composition as a pharmaceutical composition for parenteral delivery.

In one embodiment, the pH of the aqueous solution is 5.0 to 7.0, e.g., 6.0 to 7.0. In another embodiment, the pharmaceutical composition is formulated for parenteral administration.

In another aspect, provided herein is a pharmaceutical composition formulated for parenteral administration for the treatment of complicated intra-abdominal infections or complicated urinary tract infections, the pharmaceutical composition comprising a compound of formula (III) in a lyophilized composition obtained by lyophilizing an aqueous solution comprising tazobactam and an amount of ceftolozane sulfate containing 1,000 mg of ceftolozane active per 500 mg of tazobactam acid.

B. Co-Lyophilization

In one aspect, provided herein is a method of preparing a composition comprising ceftolozane and sodium chloride, comprising combining sodium chloride with ceftolozane, wherein 125-1000 mg sodium chloride per 1000 mg of ceftolozane is combined, followed by lyophilization of the sodium chloride ceftolozane mixture. The process is referred to herein as "co-lyophilization". In another aspect, provided herein is a method of preparing a composition comprising sodium chloride, tazobactam, and ceftolozane, comprising combining sodium chloride, tazobactam, and ceftolozane, wherein 125-1000 mg sodium chloride per 1000 mg of ceftolozane is combined, followed by lyophilization of the mixture of sodium chloride, tazobactam, and ceftolozane.

Also provided herein is a method of preparing a pharmaceutical composition comprising sodium chloride, ceftolozane, and tazobactam, comprising combining sodium chloride, tazobactam, and ceftolozane, followed by spray-drying the mixture of sodium chloride, ceftolozane, and tazobactam.

Figure 2:
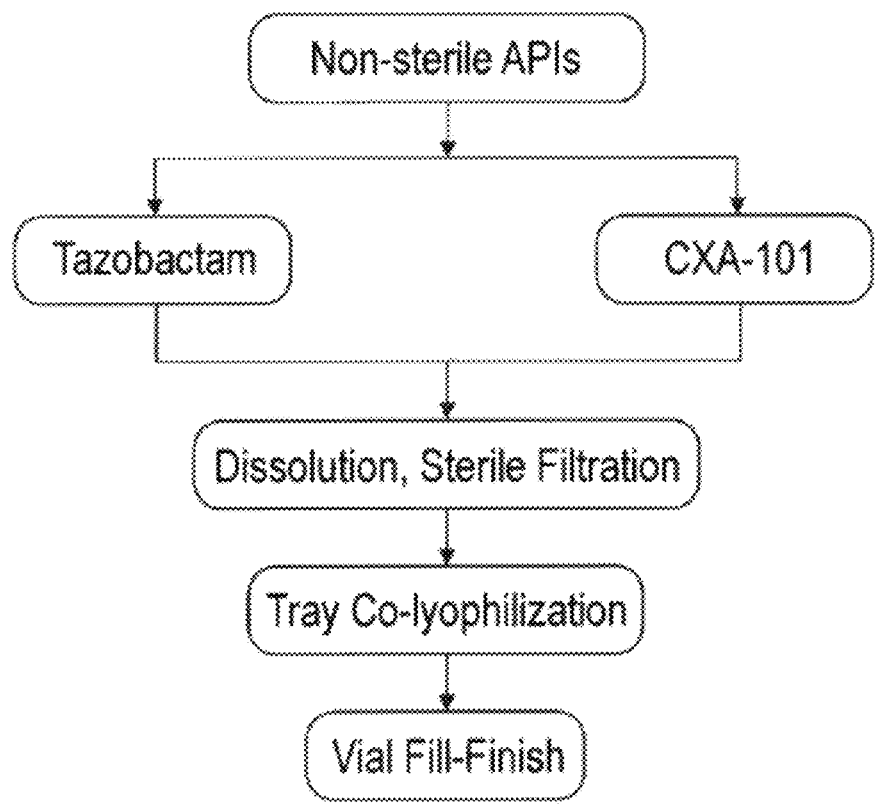
FIG. 2 is a flowchart showing the steps for preparing a CXA-201 composition comprising ceftolozane (referred to as CXA-101) and tazobactam using a co-lyophilization process, as described herein.
Figure 3:
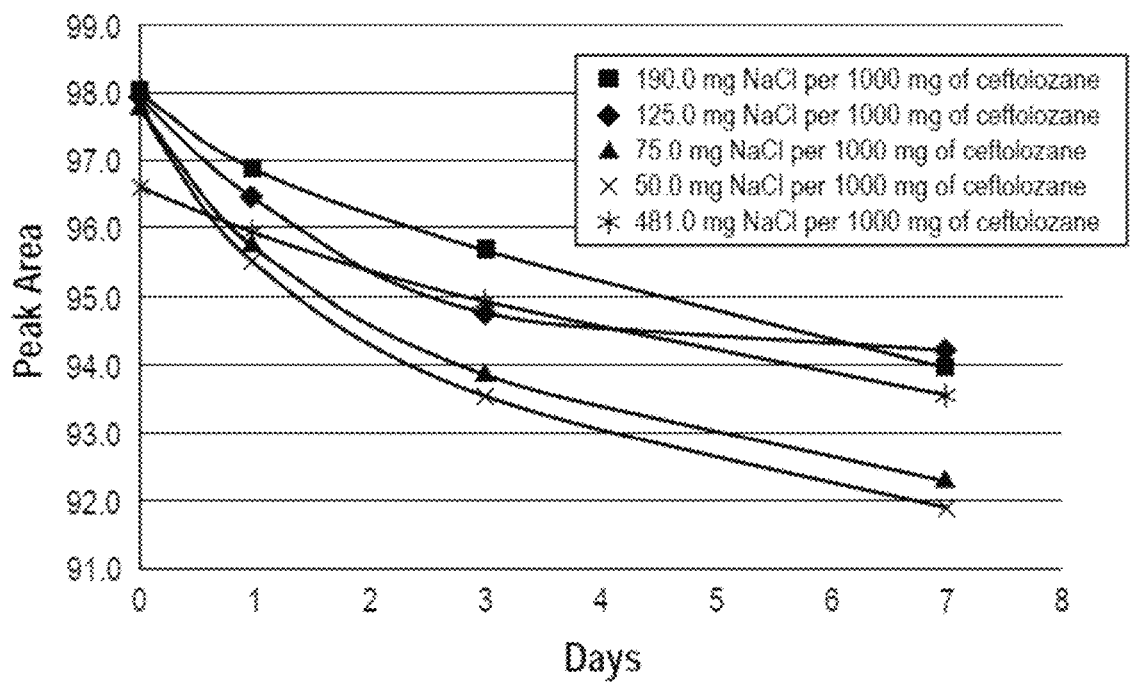
FIG. 3 is a plot of the data points from Table 6, showing the purity of the ceftolozane in CXA-101 compositions at 60° C. on day 0, day 1, day 3, and day 7, as measured by HPLC, wherein the CXA-101 compositions comprise ceftolozane and sodium chloride.

FIG. 2 is a flowchart showing the steps for preparing a CXA-201 composition comprising ceftolozane (referred to as CXA-101) and tazobactam using a co-lyophilization process, as described herein.

In another aspect, provided herein is a pharmaceutical composition comprising stabilized ceftolozane sulfate obtained by a process comprising lyophilizing an aqueous solution comprising 125 mg to 500 mg sodium chloride with an amount of ceftolozane sulfate providing 1,000 mg of ceftolozane active, to obtain the lyophilized stabilized ceftolozane sulfate composition.

In one embodiment, the stabilized ceftolozane is obtained by lyophilizing the sodium chloride and ceftolozane sulfate with L-arginine. In another embodiment, the stabilized ceftolozane is obtained by lyophilizing an aqueous solution having a pH of about 5.0 to 7.0, e.g., 6.0 to 7.0.

In another embodiment, the stabilized ceftolozane is obtained by lyophilizing the sodium chloride and ceftolozane sulfate with L-arginine and citric acid. In another embodiment, the pharmaceutical composition is formulated for parenteral administration. In another embodiment, the composition is a unit dosage form in a container comprising 125 mg to 500 mg sodium chloride, 1,000 mg of ceftolozane in the form of ceftolozane sulfate, and L-arginine. In another embodiment, the pharmaceutical composition is formulated for parenteral administration. In another embodiment, the pH of the aqueous solution is 6.0 to 7.0.

In another aspect, provided herein is a container comprising a pharmaceutical composition of stabilized ceftolozane sulfate, obtained by a process comprising the step of: lyophilizing an aqueous solution comprising 125 mg to 500 mg sodium chloride with an amount of ceftolozane sulfate providing 1,000 mg of ceftolozane active, to obtain the lyophilized stabilized ceftolozane sulfate composition; filling the lyophilized stabilized ceftolozane composition into a container.

IV. Manufacturing for the Prevention of Cross-Contamination

Recent FDA manufacturing guidance (published in April 2013) states that manufacturing facilities dedicated to manufacturing a sensitizing non-penicillin beta-lactam compound should be "completely and comprehensively separated" from areas in the facility in which any class of sensitizing beta-lactam is manufactured. See U.S. Department of Health and Human Services Food and Drug Administration, Center for Drug Evaluation and Research, Non-Penicillin Beta-Lactam Drugs: A CGMP Framework for Preventing Cross-Contamination (April 2013) ("FDA Guidance"). The FDA also considers separation of production facilities for penicillins to be good manufacturing practice. The FDA Guidance can be understood to require the use of a dedicated facility to manufacture antibiotic compounds comprising a non-penicillin beta-lactam compound (e.g., a cephalosporin) and a BLI compound with a beta-lactam ring (e.g., tazobactam). Accordingly, a facility that manufactures a product containing both cephalosporin and a beta-lactam containing BLI such as tazobactam for sale in the United States cannot be subsequently used to manufacture any other products containing beta-lactam ring, other than additional combinations of other cephalosporins with the same BLI compound (e.g., other non-penicillin beta-lactam compounds including other cephalosporin antibiotics cannot be subsequently manufactured in the facility).

Beta-lactam antibiotics, including penicillin and the non-penicillin classes, share a basic chemical structure that includes a three-carbon, one-nitrogen cyclic amine structure known as the beta-lactam ring. The side chain associated with the beta-lactam ring is a variable group attached to the core structure by a peptide bond; the side chain variability contributes to antibacterial activity. As of the date of this publication, FDA has approved over 34 beta-lactam compounds as active ingredients in drugs for human use. (see, e.g., FDA's Approved Drug Products with Therapeutic Equivalence Evaluations, generally known as the Orange Book) Beta-lactam antibiotics include the following five classes: penicillins (e.g., ampicillin, oxacillin); cephalosporins (e.g., cephalexin, cefaclor); penems (e.g., imipenem, meropenem); carbacephems (e.g., loracarbef); and monobactams (e.g., aztreonam). (Yao, JDC, and RC Moellering, Jr., Antibacterial agents, in Manual of Clinical Microbiology, 9th edition, edited by PR Murray et al., Washington D.C., ASM Press, 2007.)

Under the FDA Guidance, a manufacturing facility handling a product for sale in the United States containing both a cephalosporin (e.g, ceftolozane) and a penicillin nucleus (e.g., tazobactam) cannot be subsequently used in the manufacture of any other class of beta-lactam products, including all other penicillins, cephalosporins, penems, carbacephems and monobactams or in the manufacture of other finished pharmaceuticals or active pharmaceutical ingredients. The FDA Guidance states that (non-penicillin) cephalosporin beta-lactam compounds (e.g., such as ceftolozane) for sale in the United States must be "completely and comprehensively separated from" manufacturing areas that handle any other class of beta-lactam compound (e.g., compounds in the penicillin class).

A product containing ceftolozane and tazobactam includes both a non-penicillin beta-lactam cephalosporin (ceftolozane) and a beta-lactamase inhibitor with a beta-lactam moiety (tazobactam). Under the FDA Guidance, these two compounds must be "completely and comprehensively separated." Accordingly, there is a need for methods of manufacturing antibiotic compositions comprising ceftolozane and tazobactam for sale in the United States in compliance with the FDA Guidance, as well as antibiotic compositions manufactured in accordance with the FDA Guidance without affecting the purity, stability, and safety of the resulting composition.

Provided herein are methods of manufacturing or preparing pharmaceutical compositions containing two or more beta-lactam compounds in accordance with FDA Guidance, as well as pharmaceutical compositions manufactured in compliance with FDA Guidance. Specifically, certain manufacturing methods are provided herein that conform to standards recommended by FDA Guidance for the avoidance of cross-contamination of non-penicillin beta-lactam drugs.

In one aspect, provided herein is an antibacterial pharmaceutical composition formulated for parenteral administration for the treatment of infections, the pharmaceutical composition comprising a therapeutically effective amount of ceftolozane sulfate and tazobactam in a ratio of 1,000 mg ceftolozane active per 500 mg of tazobactam active, the pharmaceutical composition obtained by a process comprising the steps of:
  a. lyophilizing a first aqueous solution in the absence of tazobactam, the first aqueous solution comprising ceftolozane sulfate, to obtain a first lyophilized ceftolozane composition;
  b. blending the lyophilized ceftolozane composition with a tazobactam composition comprising tazobactam prepared and provided in the absence of ceftolozane;
wherein the process is completed in the absence of other non-cephalosporin beta-lactam compounds.

In another aspect, provided herein is a unit dosage form of a pharmaceutical composition formulated for parenteral administration for the treatment of complicated intra-abdominal infections or complicated urinary tract infections, the pharmaceutical composition comprising ceftolozane sulfate and tazobactam in a ratio of 1,000 mg ceftolozane active per 500 mg of tazobactam active, the pharmaceutical composition obtained by a process comprising the steps of
  a. lyophilizing a first aqueous solution in the absence of tazobactam, the first aqueous solution comprising ceftolozane sulfate, 125 mg to 500 mg of sodium chloride per 1,000 mg of ceftolozane active, to obtain a first lyophilized ceftolozane composition,
  b. lyophilizing a second solution comprising tazobactam in the absence of ceftolozane to form a second lyophilized tazobactam composition; and
  c. blending the first lyophilized ceftolozane composition and the second lyophilized tazobactam composition to obtain the antibacterial composition;
wherein the process is completed in the absence of other non-cephalosporin beta-lactam compounds.

V. Methods of Treatment

Pharmaceutical compositions comprising ceftolozane/tazobactam are being developed as an intravenous (IV) formulation for the treatment of complicated urinary tract infections (cUTIs) and complicated intra-abdominal infections (cIAIs).

Ceftolozane/tazobactam is an antibacterial composition including ceftolozane, a cephalosporin with potent antipseudomonal cephalosporinactivity, in combination with tazobactam, a beta (β)-lactamase inhibitor (BLI). Like other members of the cephalosporin class, ceftolozane is believed to exert its bactericidal activity by inhibiting essential penicillin-binding proteins (PBPs), resulting in inhibition of cell wall synthesis and subsequent cell death. Ceftolozane has activity against *Pseudomonas aeruginosa* including strains that are resistant to carbapenems, cephalosporins, fluoroquinolones, and aminoglycosides, and other common Gram-negative pathogens, including most extended-spectrum β-lactamase (ESBL)-producing *Enterobacteriaceae*. Tazobactam inhibits chromosomal- and plasmid-mediated bacterial class A and C β lactamases. Tazobactam is believed to protect ceftolozane from hydrolysis by covalently binding these enzymes, and broadens coverage to include most ESBL-producing *Escherichia coli, Klebsiella pneumoniae,* and other *Enterobacteriaceae*, including some *Enterobacteriaceae* overexpressing AmpC. Tazobactam inhibits or decreases the activity of beta-lactamases (e.g., bacterial beta-lactamases), and can be combined with beta-lactam compounds (e.g., antibiotics), thereby broadening the spectrum of the beta-lactam compound and increasing the beta-lactam compound's efficacy against organisms that produce beta-lactamase. A compound or a composition possesses efficacy against an organism if it kills or weakens the organism, or inhibits or prevents reproduction the organism.

The CXA-201 product (ceftolozane/tazobactam for injection) is undergoing regulatory review for the treatment of complicated intra-abdominal infections (cIAI) caused by susceptible isolates of the Gram-negative and Gram-positive microorganisms such as: *Citerobacter freundii, Escherichia coli, Enterobacter cloacae, Klebsiella pneumonia, Klebsiella oxytoca, Proteus mirabilis,* and *Pseudomonas aeruginosa*. In patients who are at risk of mixed aerobic-anaerobic infection, concurrent therapy with an anti-anaerobic agent can also be used.

The CXA-201 product (ceftolozane/tazobactam for injection) is undergoing regulatory review for the treatment of complicated urinary tract infections (cUTI), including pyelonephritis caused by susceptible isolates of the following Gram-negative microorganisms: *Enterobacter* spp, *Escherichia coli, Klebsiella pneumonia, Proteus mirabilis* and *Pseudomonas aeruginosa*. In one embodiment, a pharmaceutical composition comprising a CXA-201 product (e.g., the unit dosage container of Table 29 below) is reconstituted in a pharmaceutically acceptable carrier (e.g., a total volume of about 90-150 mL, preferably about 110 mL, of 0.9% aqueous sodium chloride for injection or in initial volume of 10-20 mL of water for injection or 0.9% aqueous sodium chloride for injection, followed by dilution of this solution into a 100 mL volume of 0.9% aqueous sodium chloride for injection). The resulting pharmaceutical composition can be infused into a patient in need thereof for treatment of a complicated intra-abdominal infection (e.g., using 1 hour infusion times) three times per day (e.g., once every 8 hours) for a recommended duration of treatment (e.g. 4-10 days).

The preferred dosage of (ceftolozane/tazobactam for injection) for cUTI and cIAI is 1.5 g administered every 8 hours by intravenous (IV) infusion over 1 hour in patients ≥18 years of age. The duration of therapy should be guided by the severity and site of infection and the patient's clinical and bacteriological progress. In one embodiment, a pharmaceutical composition comprising a CXA-201 product (e.g., the unit dosage container of Table 29 below) is reconstituted in a pharmaceutically acceptable carrier (e.g., a total volume of about 90-150 mL, preferably about 110 mL, of 0.9% aqueous sodium chloride for injection or in initial volume of 10-20 mL of water for injection or 0.9% aqueous sodium chloride for injection, followed by dilution of this solution into a 100 mL volume of 0.9% aqueous sodium chloride for injection). The resulting pharmaceutical composition can be infused into a patient in need thereof for treatment of a Complicated Urinary Tract Infections (cUTI), Including Pyelonephritis (e.g, using 1 hour infusion times) three times per day (e.g., once every 8 hours) for a recommended duration of treatment (e.g. 7 days).

Ceftolozane/tazobactam displays potent antibacterial activity against common Gram-negative organisms, including *Enterobacteriaceae* and *Pseudomonas aeruginosa*; select Gram-positive organisms, including *streptococci*; the majority of pathogenic enteric bacilli and select Gram-positive anaerobic species, thus making ceftolozane/tazobactam a potentially practical choice for pathogens involved in gastro-intestinal, urinary and community acquired as well as nosocomial respiratory infections. In general, the Gram-positive and Gram-negative spectrum of ceftolozane is similar to ceftazidime, but its antipseudomonal activity is the most potent among all currently available β-lactams, including the cephalosporins and carbapenems. Most importantly, ceftolozane has been shown to be active against strains of *P. aeruginosa* that are resistant to carbapenems, cephalosporins, fluoroquinolones, and aminoglycosides, including the majority of multi-drug resistant isolates. Indeed, the minimum inhibitory concentration (MIC) required to inhibit the growth of 90% of organisms (MIC90) for *P. aeruginosa* (MIC90≤2 μg/mL) is the lowest among all systemically administered antipseudomonal antibiotics.

In vitro studies have demonstrated that ceftolozane/tazobactam has a broad spectrum of activity against Gram-negative bacteria. The in vitro activity of ceftolozane and ceftolozane/tazobactam was evaluated against a broad range of Gram-positive and Gram-negative bacteria. It was observed that tazobactam potentiated the activity of ceftolozane against *Acinetobacter* spp. and common species of *Enterobacteriaceae*, including *Citrobacter* spp., *Enterobacter cloacae*, *E. coli*, *K. pneumoniae*, *Proteus mirabilis*, and *Serratia marcescens*. These surveillance data demonstrate that 88% to 100% of these *Enterobacteriaceae* species are inhibited at <8 μg/mL.

In one aspect, provided herein is a method for the treatment of bacterial infections in a mammal, comprising administering to said mammal a therapeutically effective amount of a pharmaceutical composition prepared according to the methods described herein. In another aspect, provided herein is a method for the treatment of bacterial infections in a mammal, comprising administering to said mammal a therapeutically effective amount of tazobactam and ceftolozane. In certain embodiments of the above methods, the bacterial infection is caused by an extended-spectrum beta-lactamase-producing organism. In certain embodiments, the bacterial infection is caused by an antibiotic-resistant organism. In yet another aspect, the invention is a method for the treatment of bacterial infections in a mammal, comprising administering to said mammal a therapeutically effective amount of a pharmaceutical composition comprising both tazobactam and ceftolozane. In certain embodiments of the above methods, the bacterial infection is caused by an extended-spectrum beta-lactamase-producing organism. In certain embodiments, the bacterial infection is caused by an antibiotic-resistant organism.

In another aspect, provided herein is a method for the treatment of bacterial infections in a mammal, comprising administering to said mammal a therapeutically effective amount of a pharmaceutical composition comprising tazobactam, ceftolozane, and less than 0.1% by weight of the compound RRT 1.22. In another embodiment of the treatment method, the pharmaceutical composition comprises tazobactam, ceftolozane, and less than 0.05% by weight of the compound RRT 1.22.

In certain embodiments of the treatment methods, the pharmaceutical composition further comprises 125 to 1000 mg sodium chloride per 1000 mg of ceftolozane, e.g., 125 to 500 mg sodium chloride per 1000 mg of ceftolozane, 200-500 mg sodium chloride per 1000 mg of ceftolozane, 300-500 mg sodium chloride per 1000 mg of ceftolozane, 400-500 mg sodium chloride per 1000 mg of ceftolozane, 450-500 mg sodium chloride per 1000 mg of ceftolozane, 460-500 mg sodium chloride per 1000 mg of ceftolozane, or about 476 mg sodium chloride per 1000 mg of ceftolozane. In one specific embodiment of the treatment methods, the pharmaceutical composition further comprises about 487 mg sodium chloride per 1000 mg of ceftolozane.

In other embodiments of the treatment methods, the pharmaceutical composition comprises 250-750 mg tazobactam per 1000 mg of ceftolozane, e.g., 250-700 mg tazobactam per 1000 mg of ceftolozane, 300-700 mg tazobactam per 1000 mg of ceftolozane, 300-650 mg tazobactam per 1000 mg of ceftolozane, 350-650 mg tazobactam per 1000 mg of ceftolozane, 350-600 mg tazobactam per 1000 mg of ceftolozane, 400-600 mg tazobactam per 1000 mg of ceftolozane, 400-550 mg tazobactam per 1000 mg of ceftolozane, 450-550 mg tazobactam per 1000 mg of ceftolozane, or about 500 mg tazobactam per 1000 mg of ceftolozane.

Non-limiting examples of the bacterial infections that can be treated by the methods of the invention include infections caused by: aerobic and facultative gram-positive microorganisms (e.g., *Staphylococcus aureus*, *Enterococcus faecalis*, *Staphylococcus epidermidis*, *Streptococcus agalactiae*, *Streptococcus pneumonia*, *Streptococcus pyogenes*, *Viridans group streptococci*), aerobic and facultative gram-negative microorganisms (e.g., *Acinetobacter baumanii*, *Escherichia coli*, *Haemophilus influenza*, *Klebsiella pneumonia*, *Pseudomonas aeruginosa*, *Citrobacter koseri*, *Moraxella catarrhalis*, *Morganella morganii*, *Neisseria gonorrhoeae*, *Proteus mirabilis*, *Proteus vulgaris*, *Serratia marcescens*, *Providencia stuartii*, *Providencia rettgeri*, *Salmonella enterica*), gram-positive anaerobes (*Clostridium perfringens*), and gram-negative anaerobes (e.g., *Bacteroides fragilis* group (e.g., *B. fragilis*, *B. ovatus*, *B. thetaiotaomicron*, and *B. vulgates*), *Bacteroides distasonis*, *Prevotella melaninogenica*).

In certain embodiments of the methods described herein, the bacterial infections resulting from beta-lactamase-producing organisms are treated or controlled. Non-limiting examples of beta-lactamase-producing organisms include:

(1) ESBL (extended-spectrum beta-lactamase)-producing organisms selected from the group consisting of *Enterobacteriaceae* spp.: *Escherichia coli, Klebsiella* spp. (including *K. pneumoniae* and *K. oxytoca*), *Proteus mirabilis, Proteus vulgaris, Enterobacter* spp., *Serratia* spp., *Citrobacter* spp., *Pseudomonas* spp., *Acinetobacter* spp.) and *Bacteroides* spp.;

(2) CSBL (conventional-spectrum beta-lactamase)-producing organisms, known to those of skill in the art; and (3) Inducible-AmpC-type beta-lactamases, such as *Citrobacter* spp., *Serratia* spp., *Morganella morganii, Proteus vulgaris*, and *Enterobacter cloacae*.

In certain embodiments of the methods described herein, the bacterial infection is associated with one or more of the following conditions:

Appendicitis (complicated by rupture or abscess) and peritonitis caused by piperacillin-resistant beta-lactamase producing strains of *Escherichia coli* or the following members of the *Bacteroides fragilis* group: *B. fragilis, B. ovatus, B. thetaiotaomicron*, or *B. vulgates;*

Uncomplicated and complicated skin and skin structure infections, including cellulitis, cutaneous abscesses, and ischemic/diabetic foot infections caused by piperacillin-resistant, beta-lactamase producing strains of *Staphylococcus aureus;*

Postpartum endometritis or pelvic inflammatory disease caused by piperacillin-resistant, beta-lactamase producing strains of *Escherichia coli;*

Community-acquired pneumonia (moderate severity only) caused by piperacillin-resistant, beta-lactamase producing strains of *Haemophilus influenza;*

Nosocomial pneumonia (moderate to severe) caused by piperacillin-resistant, beta-lactamase producing strains of *Staphylococcus aureus* and by *Acinetobacter baumanii, Haemophilus influenzae, Klebsiella pneumoniae*, and *Pseudomonas aeruginosa*. Nosocomial pneumonia is also known as hospital acquired/ventilator-associated bacterial pneumonia (HABP/VABP);

Complicated intra-abdominal infections (cIAI);
Complicated urinary tract infections (cUTIs);
Acute Pyelonephritis; and
Systemic Inflammatory Response Syndrome (SIRS).

Also provided herein is the use of tazobactam, and hydrates and solvates thereof, in combination with ceftolozane, for the preparation of a medicament for the treatment of bacterial infections. The bacterial infections can result from either gram-negative or gram-positive organisms.

The compositions provided herein can be used in the treatment of infections caused by *Pseudomonas aeruginosa, Serratia marcescens, Escherichia coli, Klebsiella pneumoniae, Haemophilus influenzae*, or *Streptococcus pneumonia*.

In one embodiment of the treatment methods, the bacterial infections are Gram-negative bacterial infections. In one embodiment, the gram-negative infections are complicated Urinary Tract Infections (cUTI) and complicated intra-abdominal infections (cIAI). In another embodiment, the gram-negative bacterial infections are caused by *Pseudomonas aeruginosa, E. coli*, and/or *Klebsiella pneumonia*.

In a further embodiment, provided herein is a method for the treatment of gram-negative bacterial infections in a mammal, comprising administering to said mammal a therapeutically effective amount of a pharmaceutical composition comprising ceftolozane, about 500 mg tazobactam free acid per 1000 mg of ceftolozane, about 476 mg sodium chloride per 1000 mg of ceftolozane, about 587 mg L-arginine per 1000 mg of ceftolozane, and about 21 mg anhydrous citric acid per 1000 mg of ceftolozane. In one embodiment, the gram-negative bacterial infections are selected from the group consisting of complicated Urinary Tract Infections (cUTI) and complicated intra-abdominal infections (cIAI). In another embodiment, the gram negative bacterial infection is nosocomial pneumonia.

In another specific embodiment, provided herein is a method for the treatment of gram-negative bacterial infections in a mammal, comprising administering to said mammal a therapeutically effective amount of a pharmaceutical composition comprising ceftolozane, about 500 mg tazobactam free acid equivalents per 1000 mg of ceftolozane, about 487 mg sodium chloride per 1000 mg of ceftolozane, about 600 mg L-arginine per 1000 mg of ceftolozane, and about 21 mg anhydrous citric acid per 1000 mg of ceftolozane. In one embodiment, the gram-negative bacterial infections are selected from the group consisting of complicated Urinary Tract Infections (cUTI) and complicated intra-abdominal infections (cIAI). In another embodiment, the gram negative bacterial infection is nosocomial pneumonia.

In one embodiment, provided herein is a method for the treatment of an infection in a mammal, wherein the infection is caused by *Pseudomonas aeruginosa, Serratia marcescens, Escherichia coli, Klebsiella pneumoniae, Haemophilus influenzae*, or *Streptococcus pneumoniae* comprising administering to said mammal a therapeutically effective amount of a pharmaceutical composition comprising ceftolozane, corresponding to approximately 1000 mg of the free base form of ceftolozane; tazobactam, corresponding to approximately 500 mg of the tazobactam acid form; and 400-500 mg sodium chloride. In one embodiment, the pharmaceutical composition further comprises 500-650 mg L-arginine and 15-30 mg anhydrous citric acid.

In another embodiment, provided herein is a method for the treatment of urinary tract infection, intra-abdominal infection, or nosocomial pneumonia in a mammal, comprising administering to said mammal a therapeutically effective amount of a pharmaceutical composition comprising ceftolozane, corresponding to approximately 1000 mg of the free base form of ceftolozane; tazobactam, corresponding to approximately 500 mg of the tazobactam acid form; and 400-500 mg sodium chloride. In an embodiment, the pharmaceutical composition comprises 487 mg sodium chloride. In one embodiment, the pharmaceutical composition further comprises 500-650 mg L-arginine and 15-30 mg anhydrous citric acid.

In one embodiment, provided herein is a method for the treatment of an infection in a mammal, wherein the infection is caused by *Pseudomonas aeruginosa, Serratia marcescens, Escherichia coli, Klebsiella pneumoniae, Haemophilus influenzae*, or *Streptococcus pneumoniae* comprising administering to said mammal a therapeutically effective amount of a pharmaceutical composition comprising approximately 1147 mg ceftolozane sulfate; approximately 537 mg tazobactam sodium; and 400-500 mg sodium chloride. In one embodiment, the pharmaceutical composition further comprises 500-650 mg L-arginine and 15-30 mg anhydrous citric acid.

In another embodiment, provided herein is a method for the treatment of urinary tract infection, intra-abdominal infection, or nosocomial pneumonia in a mammal, comprising administering to said mammal a therapeutically effective amount of a pharmaceutical composition comprising approximately 1147 mg ceftolozane sulfate; approximately 537 mg tazobactam sodium; and 400-500 mg sodium chloride. In an embodiment, the pharmaceutical composition comprises 487 mg sodium chloride. In one embodiment, the pharmaceutical composition further comprises 500-650 mg L-arginine and 15-30 mg anhydrous citric acid.

In one embodiment, provided herein is a method for the treatment of an infection in a mammal, wherein the infection is caused by *Pseudomonas aeruginosa, Serratia marcescens, Escherichia coli, Klebsiella pneumoniae, Haemophilus influenzae*, or *Streptococcus pneumoniae* comprising administering to said mammal a therapeutically effective amount of a pharmaceutical composition comprising approximately 1147 mg ceftolozane sulfate; approximately 537 mg tazobactam sodium; approximately 487 mg sodium chloride; and approximately 600 mg L-arginine. In one embodiment, the pharmaceutical composition further comprises 15-30 mg anhydrous citric acid.

As used herein, "treating", "treat" or "treatment" describes the management and care of a patient for the purpose of combating a disease, condition, or disorder and includes the administration of a pharmaceutical composition of the present invention to alleviate the symptoms or complications of a disease, condition or disorder, or to eliminate the disease, condition or disorder. The term "treat" can also include treatment of a cell in vitro or an animal model.

By a "therapeutically effective amount" of a compound of the invention is meant a sufficient amount of the compound to treat the disorder (e.g., bacterial infection). The specific therapeutically effective amount that is required for the treatment of any particular patient or organism (e.g., a mammal) will depend upon a variety of factors including the disorder being treated and the severity of the disorder; the activity of the specific compound or composition employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety). The therapeutically effective amount for a given situation can be readily determined by routine experimentation and is within the skill and judgment of the ordinary clinician.

As used herein, "189 mg sodium from sodium chloride per 1000 mg of ceftolozane" refers to a ratio of sodium from the sodium chloride to ceftolozane active. For example, "189 mg sodium from sodium chloride per 1000 mg of ceftolozane" includes, for example, 94.5 mg sodium from sodium chloride per 500 mg of ceftolozane, as well as, for example, 47.25 mg sodium from sodium chloride per 250 mg ceftolozane. In addition, "1,000 mg of ceftolozane as ceftolozane sulfate" refers to an amount of ceftolozane sulfate effective to provide 1,000 mg of ceftolozane. "189 mg sodium from sodium chloride" refers to the amount of sodium chloride (e.g., 480 mg) effective to provide 189 mg of sodium. The amount of sodium from sodium chloride per gram of ceftolozane activity in a pharmaceutical composition containing ceftolozane sulfate, chloride and sodium chloride can be calculated using the relevant molecular weights of ceftolozane, ceftolozane sulfate, sodium chloride and sodium. For example, a composition comprising about 1,147 mg ceftolozane sulfate and 189 mg sodium from sodium chloride contains 480 mg sodium chloride per 1,000 mg ceftolozane active.

Unless otherwise indicated, as used herein, the term "Related Substances" with respect to HPLC detection refers to all the ceftolozane related process impurities and degradation products other than ceftolozane separated and detected by HPLC according to Example 1. Unless otherwise indicated, as used herein, the term "% Related Substances" refers to the % of the total HPLC peak area obtained by Example 1 attributed to all the ceftolozane related process impurities and degradation products other than ceftolozane.

EXAMPLES

Example 1: HPLC Analysis of Compositions Comprising Ceftolozane

The purity of ceftolozane in the pharmaceutical compositions was measured using the analytical HPLC method described below.

The HPLC methodologies described herein were used to acquire the data provided in Examples 5 and 8.

Analytical HPLC Method

A. Operative Conditions

Column: Develosil ODS-UG-5; 5 μm, 250×4.6 mm (Nomura Chemical, Japan)

Wavelength: 254 nm (determination of CXA-101 impurities) 210 nm (determination of Tazobactam Related Compound A)

Flow rate: 1.0 mL/min

Column Temperature: 45° C.

Injection volume: 10 μL

Run Time: 85 minutes

Gradient Profile:

| Time (min) | A % | B % |
|---|---|---|
| 0 | 75 | 25 |
| 30 | 70 | 30 |
| 60 | 0 | 100 |
| 85 | 0 | 100 |
| 85.1 | 75 | 25 |
| 110 | 75 | 25 |

Mobile phase A: Sodium Perchlorate Buffer Solution (pH 2.5) (also referred to herein as "50 mM Sodium Perchlorate Monohydrate in water, adjusted to pH 2.5 with Diluted Perchloric Acid"

Preparation: Dissolve 7.02 g of Sodium Perchlorate Monohydrate in 1000.0 mL of water and adjust to pH 2.5 with Diluted Perchloric Acid (1 in 20).

Mobile phase B: Sodium Perchlorate Buffer Solution (pH 2.5): Acetonitrile in a ratio of 4:1 (v/v) (also referred to herein as "63 mM Sodium Perchlorate Monohydrate in water, adjusted to pH 2.5 with Diluted Perchloric Acid: Acetonitrile, 4:1 (v/v)")

Preparation: Dissolve 8.78 g of Sodium Perchlorate Monohydrate in 1000.0 mL of water and adjust to pH 2.5 with Diluted Perchloric Acid (1 in 20). Mix the resulting solution with Acetonitrile in the ratio 4:1 (v/v).

B. System Suitability Solution (1%)

Transfer 33 mg, accurately weighed, of Sample (use first sample if more are present) into a 10.0 mL volumetric flask. Dissolve and dilute to volume with water. Into a 100.0 mL volumetric flask, transfer 1.0 mL of this Solution and dilute with water to volume and mix.

C. Sample Preparation.

Transfer 33 mg, accurately weighed, of Sample into a 10.0 mL volumetric flask. Dissolve and dilute to volume with water. Prepare just before injection into the HPLC system.

D. HPLC Analysis Procedure

1. Inject Blank (water)
2. Inject System Suitability Solution and check for tailing factor and theoretical plates number for CXA-101 and Tazobactam peaks:
   The tailing factor must not be greater than 1.5
   Theoretical plates number must not be less than 10000
3. Inject Sample Solution
4. Identify the peaks of CXA-101 Related Substances in the Sample chromatogram, recorded at 254 nm, on the basis of the RRT values reported in Table 1.
5. Identify the peak of Tazobactam Related Compound A in the Sample chromatogram, recorded at 210 nm, on the basis of the RRT values reported in Table 1A.

TABLE 1A

Relative retention times of ceftolozane related substances

| Impurity | RRT |
| --- | --- |
| Peak 1 (P1) | ~0.15 |
| Peak 2 (P2) | ~0.16 |
| Peak 3 (P3) | ~0.4 |
| Peak 4 (P4) | ~0.6 |
| Peak 5 (P5) | ~0.89 |
| CXA-101 | 1.0 |

TABLE 1A-continued

Relative retention times of ceftolozane related substances

| Impurity | RRT |
| --- | --- |
| Peak 6 (P6) | ~1.2 |
| Peak 7 (P7) | ~1.3 |
| Peak 8 (P8) | ~1.4 |
| Peak 9 (P9) | ~1.7 |
| Peaks 10, 11 (P10, P11) | ~2.3 |

TABLE 1B

Related Substances of CXA-101 Drug Substance and Drug Product

| Compound | Proposed Structure | Proposed Source |
| --- | --- | --- |
| Peak 1<br>3-side chain | [structure] | Degradation product and process impurity |
| Peak 2 | Unidentified | Process impurity |
| Peak 3 | Unidentified | Process impurity |
| Peak 4 | Unidentified | Process impurity |
| Peak 5<br>7-Epimer type | [structure] | Degradation product and process impurity |
| Peak 6 | NA | Process impurity |
| Peak 7<br>Δ3 Isomer type | [structure] | Degradation product and process impurity |
| Peak 8 | Unidentified | Process impurity |

TABLE 1B-continued

Related Substances of CXA-101 Drug Substance and Drug Product

| Compound | Proposed Structure | Proposed Source |
|---|---|---|
| Peak 9 Anti-Isomer type | 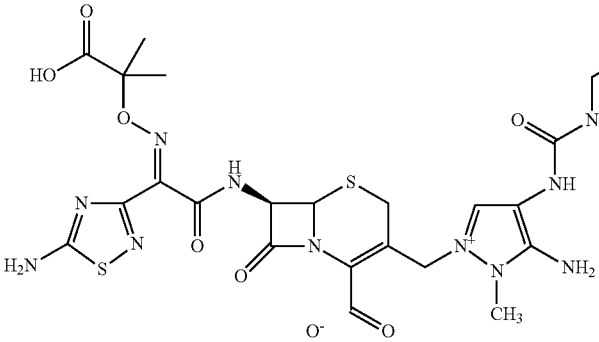 | Process impurity and Degradation impurity |
| Peaks 10, 11 | Unidentified | Process impurity |

TABLE 1C

Relative retention time of tazobactam related compound A

| Impurity | RRT |
|---|---|
| Related Compound A | 0.34 |
| Tazobactam | 1.0 |

E. Calculations

Only peaks with a value ≥LOQ are integrated.

I. CXA-101 Mpurities Determination at 254 nm.
(Tazobactam and Tazobactam Related compound A peaks are integrated separately, see below)
Each related substance at 254 nm is reported for its amount as expressed by area percent.

$$C_i = \frac{A_i \times 100}{A_t + \Sigma A_i}$$

where:

$C_i$=Amount of related substance i in the Sample calculated at 254 nm, area %

$A_i$=Peak area of related substance i in the Sample chromatogram $A_t$=Area of CXA-101 peak in the Sample chromatogram $A_t + \Sigma A_i$=Total peaks area in the Sample chromatogram Consider as any Unspecified Impurity, each peak in the chromatogram except CXA-101, peaks from 1 to 11 and every peak present in the blank chromatogram and report the largest.

II. Total CXA-101 Related Impurities at 254 nm:

Report the total impurities content as expressed by the following formula:

$$C_{T254} = \frac{\Sigma A_i \times 100}{A_t + \Sigma A_i}$$

wherein:

$C_{T254}$=total impurities content in the Sample calculated at 254 nm, area %

$A_t$=area of CXA-101 peak in the sample chromatogram $\Sigma A_i$=total peak areas of impurities in the sample chromatogram $A_t + \Sigma A_i$=total peaks area in the sample chromatogram III. Tazobactam Related Compound A Determination at 210 nm:

Integrate only the Tazobactam and Tazobactam Related Compound A peaks $$C_a = \frac{A_a \times 100}{A_a + A_T}$$

where:

$C_a$=Amount of Tazobactam Related Compound A in the Sample, are %

$A_a$=Peak area of Tazobactam Related Compound A in the Sample chromatogram $A_t$=Area of Tazobactam in the Sample chromatogram IV. Total Impurities Make the sum of Tazobactam Related Compound A (III) and the Total CXA-101 impurities determined (II)

V Quantitation Limit

| Component | LOQ % |
|---|---|
| Tazobactam | 0.03 |
| CXA-101 | 0.03 |

Example 2: Screening of Stabilizing Agents

Nine stabilizing agents were screened, including sodium chloride, fructose, xylitol, sorbitol, dextran 40, lactose, glucose, maltose, and D-mannitol. The purity of the ceftolozane in a composition comprising 100 mg ceftolozane and 100 mg of one of the stabilizing agents after 3 days at 70° C. was compared to a composition comprising 100 mg ceftolozane but no stabilizing agent.

As shown in Table 2A, the ceftolozane compositions comprising sodium chloride, dextran 40, lactose, or maltose were demonstrated to be more stable than the other ceftolozane compositions comprising the other stabilizing agents, or no stabilizing agent. Sodium chloride and maltose were selected for further investigation.

TABLE 2A

Screening of Stabilizing Agents

| | Stabilizing agent | | | | | | | | | |
|---|---|---|---|---|---|---|---|---|---|---|
| | Sodium chloride | | Fructose | | Xylitol | | Sorbitol | | Dextran 40 | |
| Storage | Initial | 70° C. 3 days | Initial | 70° C. 3 days | Initial | 70° C. 3 days | Initial | 70° C. 3 days | Initial | 70° C. 3 days |
| Appearance | White mass | Pale yellow mass | White mass | Orange paste | White mass | Orange paste | White mass | Pale yellow paste | White mass | Pale yellow mass |
| Color and clarity | Pale yellow and clear | Pale yellow and clear | Pale yellow and clear | Orange and clear | Pale yellow and clear | Orange and clear | Pale yellow and clear | Yellow and clear | Pale yellow and clear | Yellow and clear |
| pH | 5.58 | 4.23 | 6.04 | 3.81 | 5.96 | 4.18 | 6.01 | 4.00 | 5.60 | 4.36 |
| Residual rate (%) | 100.0 | 75.7 | 100.0 | 4.29 | 100.0 | 0.41 | 100.0 | 0.00 | 100.0 | 72.2 |
| Reconstitution time(s) | 15 | 30 | 20 | 40 | 15 | 180< | 15 | 160 | 170 | 160 |

| | Stabilizing agent | | | | | | | | | |
|---|---|---|---|---|---|---|---|---|---|---|
| | Lactose | | Glucose | | Maltose | | D-Mannitol | | No stabilizing agent (Control) | |
| Storage | Initial | 70° C. 3 days | Initial | 70° C. 3 days | Initial | 70° C. 3 days | Initial | 70° C. 3 days | Initial | 70° C. 3 days |
| Appearance | Pale yellow mass | Pale yellow mass | White mass | Pale yellow mass | White mass | Pale yellow mass | White mass | Pale yellow mass | Pale yellow mass | Pale yellow mass |
| Color and clarity | Pale yellow and clear | Pale yellow and clear | Pale yellow and clear | Pale yellow and clear | Pale yellow and clear | Pale yellow and clear | Pale yellow and clear | Yellow and clear | Pale yellow and clear | Yellow and clear |
| pH | 5.86 | 4.70 | 6.23 | 4.32 | 6.08 | 5.06 | 6.13 | 3.97 | 5.10 | 4.02 |
| Residual rate (%) | 100.0 | 80.5 | 100.0 | 37.3 | 100.0 | 80.9 | 100.0 | 1.38 | 100.0 | 51.2 |
| Reconstitution time(s) | 15 | 15 | 15 | 15 | 15 | 15 | 30 | 50 | 15 | 15 |

The stabilizing effect of other non-reducing sugars such as sucrose and trehalose, as well as polyvinylpyrrolidone (PVP), was also evaluated in a ceftolozane formulation.

Five samples were prepared, the components of which are shown in Table 2B below. Each sample contained 1000 mg of ceftolozane active, 40 mg citric acid monohydrate (equivalent of 36 mg citric acid anhydrous), and the same amount of L-arginine. Stabilizing reagents in four samples are 480 mg sodium chloride, 300 mg of trehalose, 300 mg of sucrose, and 300 mg of PVP, respectively. One sample was a control that contained no stabilizing reagent. The samples were in lyophilized form and stored at 60° C. for 7 days. The purities of the samples were monitored by HPLC on day 0, day 1, day 3 and day 7.

TABLE 2B

Comparison between stabilizing reagents

| Excipient | NaCl | Trehalose | Sucrose | PVP | None |
|---|---|---|---|---|---|
| Ceftolozane amount | 1000 | 1000 | 1000 | 1000 | 1000 |
| Excipient amount | 480 | 300 | 300 | 300 | N/A |
| Purity: $t_0$ | 98.42 | 98.09 | 98.14 | 97.89 | 97.94 |
| 60° C./1 d | 97.85 | 96.73 | 96.97 | 96.05 | 96.15 |
| 60° C./3 d | 97.21 | 95.36 | 95.81 | 94.57 | 94.53 |

TABLE 2B-continued

Comparison between stabilizing reagents

| Excipient | NaCl | Trehalose | Sucrose | PVP | None |
|---|---|---|---|---|---|
| 60° C./7 d | 95.65 | 94.21 | 94.19 | 92.78 | 92.06 |
| Purity Δ (0-7 d) | −2.77% | −3.88% | −3.95% | −5.11% | −5.88% |

As shown in Table 2B, the sample containing sodium chloride exhibited the best stability. The purity of ceftolozane in the sample containing sodium chloride had the slightest purity drop over 7 days. This experiment further supports the discovery that sodium chloride provides surprisingly better stabilizing effect than the other reagents.

Example 3: Stability Study of Ceftolozane Compositions Comprising Sodium Chloride, or Maltose, or No Stabilizing Agent Three ceftolozane compositions were prepared, the components of which are shown in Table 3. These compositions were put in a stressed stability study at 70° C. for 3 days and 6 days. The purity of the ceftolozane in the compositions was analyzed using the HPLC method described in Example 1.

TABLE 3

| Ceftolozane Compositions | | |
|---|---|---|
| CEF/no stabilizer | 9.5 g active | Ceftolozane |
| | 5.7 g | L-Arginine |
| | 200 mg | Citric acid |
| CEF/maltose | 9.5 g active | Ceftolozane |
| | 5.7 g | L-Arginine |
| | 200 mg | Citric acid |
| | 5 g | Maltose $H_2O$ |
| CEF/sodium chloride | 9.5 g active | Ceftolozane |
| | 5.7 g | L-Arginine |
| | 200 mg | Citric acid |
| | 4.6 g | Sodium Chloride |

The results are shown in Table 4 where only the most significant composition peaks (P1, P7, and P12) are shown. It was found that the composition comprising maltose (CEF/maltose) contained a significantly large amount of the composition P12 peak, which was identified as having the following formula:

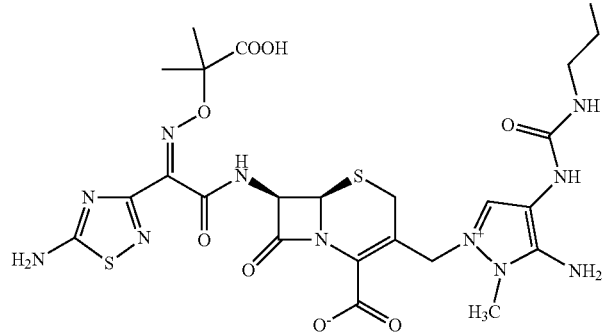

In addition, the presence of maltose produced a particularly aggregated powder after lyophilization, which has a potentially negative impact to manufacturing ceftolozane compositions.

In contrast, the ceftolozane composition comprising sodium chloride (CEF/sodium chloride) was much more stable than the ceftolozane composition comprising maltose or the ceftolozane composition comprising no stabilizing agent. Therefore, sodium chloride was, unexpectedly, a better stabilizing agent for ceftolozane compositions.

TABLE 4

Stability Study of Ceftolozane Compositions Comprising Sodium Chloride, or Maltose, or No Stabilizing Agent

| | P1 | P7 | P12 | Total |
|---|---|---|---|---|
| CEF/no stabilizer Time (days) | | | | |
| 0 | 0.49 | 0.69 | 0.00 | 1.98 |
| 3 | 3.06 | 1.29 | 0.00 | 8.48 |
| 6 | 4.11 | 1.49 | 0.00 | 10.83 |
| CEF/maltose Time (days) | | | | |
| 0 | 0.41 | 0.65 | 0.15 | 1.91 |
| 3 | 2.85 | 1.02 | 3.44 | 10.08 |
| 6 | 3.45 | 1.12 | 4.01 | 11.65 |
| CEF/sodium chloride Time (days) | | | | |
| 0 | 0.20 | 0.62 | 0.00 | 1.64 |
| 3 | 1.70 | 0.85 | 0.00 | 4.29 |
| 6 | 2.86 | 1.05 | 0.00 | 6.70 |

Example 4a: Manufacturing Procedure of Mono Product for Injection 4a.1. Preparation of the Compound Solution of CXA-101 Lyophilized Product 1) Weigh 30 kg of water for injection into the compounding vessel;

2) Add 100 g of citric acid, anhydrous and 150 g of sodium bicarbonate into the compounding vessel and dissolve them with mixing;

3) Weigh 5,000 g potency of CXA-101 drug substance and suspend it with mixing. (Note any generation of carbon dioxide.)

4) Slowly add 1,100 g of sodium bicarbonate and dissolve CXA-101 with mixing. (Again, note any generation of carbon dioxide.)

5) Add 1,146 g of sodium chloride and 10,000 g of maltose, dissolve with mixing.

6) Purge dissolved carbon dioxide in the solution with nitrogen until the pH of the solution does not change.

7) Adjust the pH of the solution to 6.0±0.1 with 5%-sodium bicarbonate solution.

8) Adjust the total weight to 56,850 g ($D_{20}$=1.137) with water for injection.

9) Confirm the pH of the compounded solution within the range 6.0±0.1.

4a.2. Prefiltration and Sterile-Filtration

10) Filtrate the compounded solution with a sterile tilter-set which consists of a 0.2 um polyvinylidene fluoride membrane filter (DURAPORE®, Millipore) and a 0.1 urn polyvinylidene fluoride membrane filter (DURAPORE®, Millipore) connected in tandem. Confirm the integrity of each filter before and after the filtration. Take approximately 100 mL of the filtrate in order to check bioburden.

11) Filter the prefiltered compounded solution through a sterile filter-set which consists of a 0.2 um polyvinylidene fluoride membrane filter and a 0.1 urn polyvinylidene fluoride membrane filter connected in tandem, and introduce the final filtrate into an aseptic room. Confirm the integrity of each filter before and after the filtration.

4a.3. Processing of container, Stopper and Flip-off Cap

12) Wash a sufficient quantity of 28 mL containers with water for injection and sterilize the washed containers by a dry-heat sterilizer. Then transfer the sterilized containers into a Grade A area located in an aseptic room.

13) Wash a sufficient quantity of stoppers with, water for injection. Sterilize and dry the washed stoppers by steam sterilizer. Then transfer the sterilized stoppers into a Grade A area located in an aseptic room.

14) Sterilize a sufficient quantity of flip-off caps by steam sterilizer. Then transfer the sterilized flip-off caps into a Grade A or B area located in an aseptic room.

4a.4. Filling and Partially Stoppering

15) Adjust the fill weight of the filtered compounded solution to 11.37 g (corresponds to 10 mL of the compounded solution), then start filling operation. Check the filled weight in sufficient frequency and confirm it is in target range (11.37 g±1%, 11.26 to 11.43 g). When deviation from the control range (11.37 g±2%, 11.14 to 11.59 g) is occurred, re-adjust the filling weight.

16) Immediately after a container is filled, partially stopper the container with a sterilized stopper. Load the filled and partially stoppered containers onto the shelves of a lyophilizer aseptically.

4a.5. Lyophilization to Crimping, Visual Inspection, Labeling and Packaging

17) After all filled and partially stoppered containers are loaded into a lyophilizer, start the lyophilization program. Freeze the loaded containers at −40° C. and keep at temperature until all containers freeze. Forward the program to primary drying step (shelf temperature; −20° C., chamber pressure; 100 to 150 mTorr). Primary drying time should be determined by monitoring the product temperature. Forward the program to secondary drying step (shelf temperature; 30° C., chamber pressure; not more than 10 mTorr) after completion of the primary drying step. After all containers are dried completely, return the chamber pressure to atmospheric pressure with sterilized nitrogen. Then stopper containers completely.

Example 4b: Manufacturing Procedure of Bulk (Tray) Lyophilized Ceftolozane

There are four main steps in the manufacture of a CXA-101 pharmaceutical composition: dissolution, sterile filtration, bulk lyophilization, and packaging into Sterbags®. These four main steps are composed of a total of 19 minor steps. The CXA-101 bulk drug product manufacturing process is presented below.

I Dissolution

1. The prescribed amount of water for injection ("WFI") is charged into the dissolution reactor.
2. A prescribed amount of citric acid is added.
3. The solution is cooled at 5° C. to 10° C.
4. A prescribed amount of CXA-101 drug substance is added to the solution.
5. A prescribed amount of L-arginine is slowly added to the solution.
6. A check for complete dissolution is performed. Solution pH is verified to be in the target range of 6.5 to 7.0.
7. A prescribed amount of sodium chloride is added to the solution, wherein the preferred amount of sodium chloride is 125-500 mg of sodium chloride per 1000 mg of ceftolozane active.
8. A check for complete dissolution is performed. Solution pH is verified to be in the target range of 6.0 to 7.0. If the pH is out of this range adjust with either L-Arginine or citric acid.
9. WFI is added to bring the net weight to adjust compounded solution concentration.
10. Samples are withdrawn for testing of final pH.

H. Sterile Filtration

11. The solution is passed through the filter (pore size 0.45 μm) followed by double filters (pore size 0.22 μm) onto a shelf on the Criofarma lyophilizer.
12. The line is washed with WFI.
13. The washing solution is passed from Step 12 through sterile filtration.

III Bulk Lyophilization

14. The washing solution is loaded onto a separate shelf in the lyophilizer (and later discarded).
15. The solution is lyophilized until dry.
16. The product shelf is cooled to 20° C.±5° C.

IV. Packaging into STERBAGS®

17. The lyophilized bulk drug product powder is delumped.
18. The milled powder is sieved.
19. The powder is then discharged into STERBAGS®

Example 5: Stabilizing Effect of Sodium Chloride in CXA-101 Compositions

A. Improvement in the Purity of the Ceftolozane in CXA-101 Pharmaceutical Compositions with Varying Amounts of Sodium Chloride A stability study was carried out at 30° C. and 60° C. and analyzed by HPLC. The sodium chloride content in the CXA-101 compositions is described in Table 5. The HPLC data are summarized in Tables 6-8. The data are also plotted in FIGS. 3-6 to show the trends of the purity, and the amounts of the composition peak 1, the composition with a RRT of 0.43 and the composition peak 3, and the composition peak 7 in the CXA-101 compositions with respect to NaCl.

TABLE 5

Sodium Chloride Content in the CXA-101 Compositions

| Samples | NaCl content |
| --- | --- |
| A1 | 481.0 mg NaCl per 1000 mg of ceftolozane |
| A2 | 190.0 mg NaCl per 1000 mg of ceftolozane |
| A3 | 125.0 mg NaCl per 1000 mg of ceftolozane |
| A4 | 75.0 mg NaCl per 1000 mg of ceftolozane |
| A5 | 50.0 mg NaCl per 1000 mg of ceftolozane |

TABLE 6

Purity of Ceftolozane in CXA-101 Compositions with Varying Amounts of Sodium Chloride

| Day | A1 | A2 | A3 | A4 | A5 |
| --- | --- | --- | --- | --- | --- |
| t0/60° C. | 0 | 96.6 | 98.0 | 97.9 | 97.8 | 97.7 |
| t0/30° C. | 0 | 98.1 | | 97.8 | 97.8 | 97.7 |
| 1 day/60° C. | 1 | 95.9 | 96.9 | 96.5 | 95.7 | 95.5 |

TABLE 6-continued

Purity of Ceftolozane in CXA-101 Compositions with Varying Amounts of Sodium Chloride

|  | Day | A1 | A2 | A3 | A4 | A5 |
|---|---|---|---|---|---|---|
| 1 day/30° C. | 1 | 98.2 |  | 97.7 | 97.7 | 97.6 |
| 3 days/60° C. | 3 | 94.9 | 95.7 | 94.8 | 93.9 | 93.6 |
| ($\Delta_{t0-t3}$) |  | (1.7) | (2.3) | (3.1) | (3.9) | (4.1) |
| 3 day/30° C. | 3 | 98.0 |  | 97.5 | 97.5 | 97.3 |
| 7 days/60° C. | 7 | 93.6 | 94.0 | 94.2 | 92.3 | 91.9 |
| 7 day/30° C. | 7 | 97.8 |  | 97.2 | 97.1 | 97.0 |
| Total Δ/60° C. |  | 3.07 | 4.06 | 3.7 | 5.48 | 5.83 |
| Total Δ/30° C. |  | 0.3 |  | 0.6 | 0.7 | 0.7 |

TABLE 7

HPLC Peak Area of Composition Peak 1 in CXA-101 Compositions with Varying Amounts of Sodium Chloride

|  | Day | A1 | A2 | A3 | A4 | A5 |
|---|---|---|---|---|---|---|
| t0/60° C. | 0 | 0.95 | 0.31 | 0.3 | 0.36 | 0.39 |
| t0/30° C. | 0 | 0.47 |  | 0.36 | 0.36 | 0.39 |
| 1 day/60° C. | 1 | 1.36 | 0.86 | 0.94 | 1.36 | 1.39 |
| 1 day/30° C. | 1 | 0.48 |  | 0.40 | 0.42 | 0.48 |
| 3 days/60° C. | 3 | 1.71 | 1.31 | 1.73 | 2.06 | 2.1 |
| 3 day/30° C. | 3 | 0.53 |  | 0.50 | 0.52 | 0.58 |
| 7 days/60° C. | 7 | 2.26 | 2.14 | 2.07 | 2.86 | 2.93 |
| 7 day/30° C. | 7 | 0.62 |  | 0.63 | 0.66 | 0.72 |
| INCREASE %/60° C. |  | 1.31 | 1.83 | 1.77 | 2.5 | 2.54 |
| INCREASE %/30° C. |  | 0.15 |  | 0.27 | 0.30 | 0.33 |

TABLE 8A

HPLC Peak Area of the Composition with a RRT of 0.43 and Composition Peak 3 in CXA-101 Compositions with Varying Amounts of Sodium Chloride

|  | Day | A1 | A2 | A3 | A4 | A5 |
|---|---|---|---|---|---|---|
| t0/60° C. | 0 | 0.28 | 0.10 | 0.09 | 0.10 | 0.11 |
| t0/30° C. | 0 | 0.15 |  | 0.10 | 0.10 | 0.11 |
| 1 day/60° C. | 1 | 0.37 | 0.13 | 0.16 | 0.35 | 0.36 |
| 1 day/30° C. | 1 | 0.13 |  | 0.09 | 0.09 | 0.10 |
| 3 days/60° C. | 3 | 0.68 | 0.21 | 0.31 | 0.71 | 0.71 |
| 3 day/30° C. | 3 | 0.17 |  | 0.13 | 0.13 | 0.14 |
| 7 days/60° C. | 7 | 1.04 | 0.36 | 0.30 | 0.81 | 0.81 |
| 7 day/30° C. | 7 | 0.19 |  | 0.16 | 0.16 | 0.17 |
| INCREASE %/60° C. |  | 0.76 | 0.26 | 0.21 | 0.71 | 0.7 |
| INCREASE %/30° C. |  | 0.04 |  | 0.06 | 0.06 | 0.06 |

TABLE 8B

The HPLC Peak Area of Composition Peak 7 in CXA-101 Compositions with Varying Amounts of Sodium Chloride

|  | Day | A1 | A2 | A3 | A4 | A5 |
|---|---|---|---|---|---|---|
| t0/60° C. | 0 | 1.31 | 0.95 | 0.96 | 1.01 | 1.02 |
| t0/30° C. | 0 | 0.68 |  | 1.00 | 1.01 | 1.02 |
| 1 day/60° C. | 1 | 1.37 | 1.10 | 1.10 | 1.23 | 1.29 |
| 1 day/30° C. | 1 | 0.68 |  | 0.99 | 1.01 | 1.02 |
| 3 days/60° C. | 3 | 1.43 | 1.19 | 1.27 | 1.41 | 1.46 |
| 3 day/30° C. | 3 | 0.68 |  | 1.03 | 1.01 | 1.05 |
| 7 days/60° C. | 7 | 1.49 | 1.31 | 1.35 | 1.55 | 1.57 |
| 7 day/30° C. | 7 | 0.68 |  | 1.01 | 1.03 | 1.07 |
| INCREASE %/60° C. |  | 0.18 | 0.36 | 0.39 | 0.54 | 0.55 |
| INCREASE %/30° C. |  | NC |  | 0.01 | 0.02 | 0.05 |

Conclusion:

The stability test demonstrates that high sodium chloride content enhances stability of CXA-101 Compositions.

The HPLC measurements on day 3 were used to analyze the stability of the CXA-101 compositions.

CXA-101 compositions comprising high amounts of sodium chloride (e.g., 125-1000 mg sodium chloride per 1000 mg of ceftolozane) were found to be more chemically stable than CXA-101 compositions comprising low amounts of sodium chloride (e.g., less than 125 mg sodium chloride per 1000 mg of ceftolozane). Table 6 shows that, by day 3 of heating at 60° C., sample A1, which has the highest salt concentration, is most stable, i.e., has the lowest $\Delta_{t0-t3}$ of all samples. By day 3, the sample with the lowest salt concentration, A5, has the highest $\Delta_{t0-t3}$ indicating the most degradation. Overall, A5 has degraded 141% more than A1. Further, Table 6 shows that, by day 3 of heating at 60° C., sample A3, which contains a lower salt concentration within the limits of the invention at 125 mg, is still significantly more stable than A4, a composition containing 75.0 mg of the salt. A3 has a $\Delta_{t0-t3}$ of 3.1, while A4 has a $\Delta_{t0-t3}$ of 3.9, meaning that A4 has degraded 26% more than A3.

B. Long-term Stability Study of CXA-101 Pharmaceutical Compositions with Varying Amounts of Sodium Chloride Another stability study was carried out at 5° C. and 25° C. The sodium chloride content in the CXA-101 compositions is described in Table 9. The amounts of citric acid and L-arginine in each composition were the same. These samples were in lyophilized form and were placed on long-term (24-36 months), real time stability programs.

The composition peak 1 is considered "diagnostic" for formulation failure because it is the first peak to go out of trend or specification (1.5%). Thus, the stability of these CXA-101 compositions was also measured by the length of storage until formulation failure as indicated by the composition peak 1. The data in Table 9 were extrapolated from data collected after 4 months. Clearly, based on the amount of the composition peak 1 in the compositions, the composition with about 480 mg sodium chloride per 1 gram ceftolozane active was significantly more stable than the compositions containing 125 mg or 62.5 mg sodium chloride per 1 gram of active ceftolozane (i.e., stability of ceftolozane compositions: 480>>125 mg>62.5 mg).

TABLE 9

The Peak 1 Failure Points of CXA-101 Compositions with Varying Amounts of Sodium Chloride

| Ceftolozane active, 1 g + | Peak 1 failure point at 5° C. | Peak 1 failure point at 25° C. |
|---|---|---|
| 480 mg NaCl | 245 months | 15 months |
| 125 mg NaCl | 70 months | 5 months |
| 62.5 mg NaCl | 25 months | 3 months* |

*Results at 3 months = 1.34%, 4 months = 1.15%

Example 6: Manufacturing Process of a CXA-201 Composition Comprising Tazobactam and CXA-101/Ceftolozane by Co-Lyophilization The manufacturing process of a CXA-201 composition comprising tazobactam and ceftolozane by co-lyophilization is shown in FIG. 2. Non-sterile bulk tazobactam and bulk ceftolozane were mixed, followed by dissolution and sterile filtration. The filtrate was then tray-lyophilized to obtain the CXA-201 composition. The CXA-201 composition can be container-filled as a final drug product. The components of a CXA-201 composition prepared by co-lyophilization are shown in Table 10.

TABLE 10

Components of a CXA-201 Composition Prepared by Co-lyophilization

| Component | Function | Amount (mg/container) |
|---|---|---|
| Ceftolozane | Active pharmaceutical ingredient | 1000 (potency) |
| L-arginine | Alkalization reagent | 587 |
| Citric acid (anhydrous) | Buffer | 21 |
| Sodium chloride | Stabilizer | 476 |
| Tazobactam (free acid) | Active pharmaceutical ingredient | 500 |
| Sodium bicarbonate | Alkalization reagent | Quantity sufficient[1] for pH 4.8 to 7.0 |
| Water | Dissolution solvent | Not more than 4% by weight[2] |
| Nitrogen | Inert gas | Sufficient quantity |

[1] Sodium content is approximately 78 mg/g of tazobactam in drug product after lyophilization.
[2] Water is removed during the lyophilization process and is controlled at no more than 4% by weight.

Example 7a: Assessment of Co-Lyophilized Combo Drug Product (i.e., a CXA-201 Composition)

A. Preparation of the Co-Lyophilized Combo Drug Product (i.e. the CXA-201 Composition)

The components of the co-lyophilized CXA-201 composition are shown in Table 11. This composition was prepared, as described above in Example 6.

TABLE 11

Components of the CXA-201 Composition Prepared by Co-Lyophilization

| CXA-201 Comp. | 16.3 g active | ceftolozane |
|---|---|---|
| | 8.1 g active | Tazobactam free ac. |
| | 15.5 g | L-Arginine |
| | 350 mg | Citric acid |
| | 7.9 g | NaCl |
| | 6.1 | pH compounded solution |

B. Stressed Stability Test

Stability studies of this CXA-201 composition prepared by co-lyophilization were carried out at 25° C. and 40° C. The composition was analyzed using HPLC. The following Tables 12 and 13 are summaries of the HPLC measurements at time zero, after one month (T1), and after three months (T2).

TABLE 12

Stability Data of Co-Lyophilized CXA-201 Composition at 25° C./RH = 60%

| Test items | Spec. D.P. | T0 | T1 25° C. | T2 25° C. |
|---|---|---|---|---|
| Related Substances | | | | |
| Peak1 | ≤1.50% | 0.31% | 0.54% | 0.71% |
| Peak2 | ≤0.40% | 0.07% | 0.07% | 0.09% |
| Peak3 | ≤0.30% | <0.03% | <0.03% | <0.03% |
| Peak4 | ≤0.80% | 0.08% | 0.08% | 0.09% |
| Peak5 | ≤1.00% | 0.27% | 0.26% | 0.29% |
| Peak6 | ≤0.15% | <0.03% | <0.03% | <0.03% |
| Peak7 | ≤2.00% | 0.64% | 0.65% | 0.66% |
| Peak8 | ≤0.15% | <0.03% | <0.03% | <0.03% |
| Peak9 | ≤0.60% | 0.05% | 0.11% | 0.10% |
| Peak10, 11 | ≤0.15% each | 0.04% | 0.04% | 0.04% |
| Peak12 | ≤2.00% | <0.03% | <0.03% | <0.03% |
| Others (RRT 0.43) | ≤0.15% | <0.03% | <0.03% | 0.04% |
| Others (RRT 1.22) | ≤0.15% | 0.13% | 0.30% | 0.38% |
| Others (RRT 2.18) | ≤0.15% | 0.03% | <0.03% | 0.05% |
| Others (RRT 2.77) | ≤0.15% | <0.03% | 0.03% | 0.03% |
| Sing. Unk. | ≤0.15% | 0.05% | 0.07% | 0.05% |
| Total | ≤5.00% | 1.67% | 2.19% | 2.77% |
| pH | report value | 5.5 | | 4.83 |

TABLE 13

Stability Data of Co-Lyophilized CXA-201 Composition at 40° C./RH = 75%

| Test items | Spec. D.P. | T0 | T1 40° C. | T2 40° C. |
|---|---|---|---|---|
| Related Substances | | | | |
| Peak1 | ≤1.50% | 0.31% | 1.77% | 2.22% |
| Peak2 | ≤0.40% | 0.07% | 0.10% | 0.16% |
| Peak3 | ≤0.30% | <0.03% | <0.03% | 0.06% |
| Peak4 | ≤0.80% | 0.08% | 0.09% | 0.09% |
| Peak5 | ≤1.00% | 0.27% | 0.27% | 0.30% |
| Peak6 | ≤0.15% | <0.03% | <0.03% | <0.03% |
| Peak7 | ≤2.00% | 0.64% | 0.69% | 0.78% |
| Peak8 | ≤0.15% | <0.03% | <0.03% | 0.10% |
| Peak9 | ≤0.60% | 0.05% | 0.09% | 0.09% |
| Peak10, 11 | ≤0.15% each | 0.04% | 0.04% | 0.05% |
| Peak12 | ≤2.00% | <0.03% | <0.03% | <0.03% |
| Others (RRT 0.43) | ≤0.15% | <0.03% | 0.09% | 0.15% |
| Others (RRT 1.22) | ≤0.15% | 0.13% | 0.74% | 0.97% |
| Others (RRT 2.18) | ≤0.15% | 0.03% | <0.03% | 0.08% |
| Others (RRT 2.77) | ≤0.15% | <0.03% | <0.03% | 0.04% |
| Sing. Unk. | ≤0.15% | 0.05% | 0.11% | 0.25% |
| Total | ≤5.00% | 1.67% | 4.49% | 6.32% |
| pH | report value | 5.5 | | 4.09 |

C. Conclusion:

A new compound having RRT=1.22 was observed in the co-lyophilized CXA-201 compositions. While not wishing to be bound by theory, the compound RRT 1.22 was identified as a compound formed by a reaction between ceftolozane and formylacetic acid, which was a by-product of tazobactam as illustrated in Marunaka et al. (Chem. Pharm. Bull. 1988, Vol. 36 (11), pp. 4478-4487). The stability data at 25° C. and at 40° C. have confirmed the continued formation of the compound RRT 1.22 over the course of time.

Example 7b: Identifying the Compound of Formula (III)

The Co-Lyophilized Combo Drug Product was prepared as described above in Example 6. The formulation composition of the Co-Lyophilized Combo drug product is shown in Table 11 (Example 7a). This sample maintained at 25° C./RH=60% and 40° C./RH=75% after one month (T1) and three months (T2). Samples were analyzed using a HPLC method as described in Example 1. The data for analysis of the samples by HPLC is shown in Example 10 in Table 23 (Stability data of Co-Lyo Combo Drug Product at 25° C.) and Table 24 (Stability data Co-Lyo Combo Drug Product at 40° C.). The presence of the compound of Formula (III) was identified has having a retention time of about 1.22 as measured by HPLC (see Example 2). RRT=1.22 was observed in co-lyophilized drug product. The compound of formula (III) is believed to be formed by a reaction between ceftolozane and formylacetic acid, which was a degradation product of tazobactam. The amount of the compound of formula (III) in a composition comprising ceftolozane and tazobactam can be increased over time at 25° C. and at 40° C.

Figure 14:
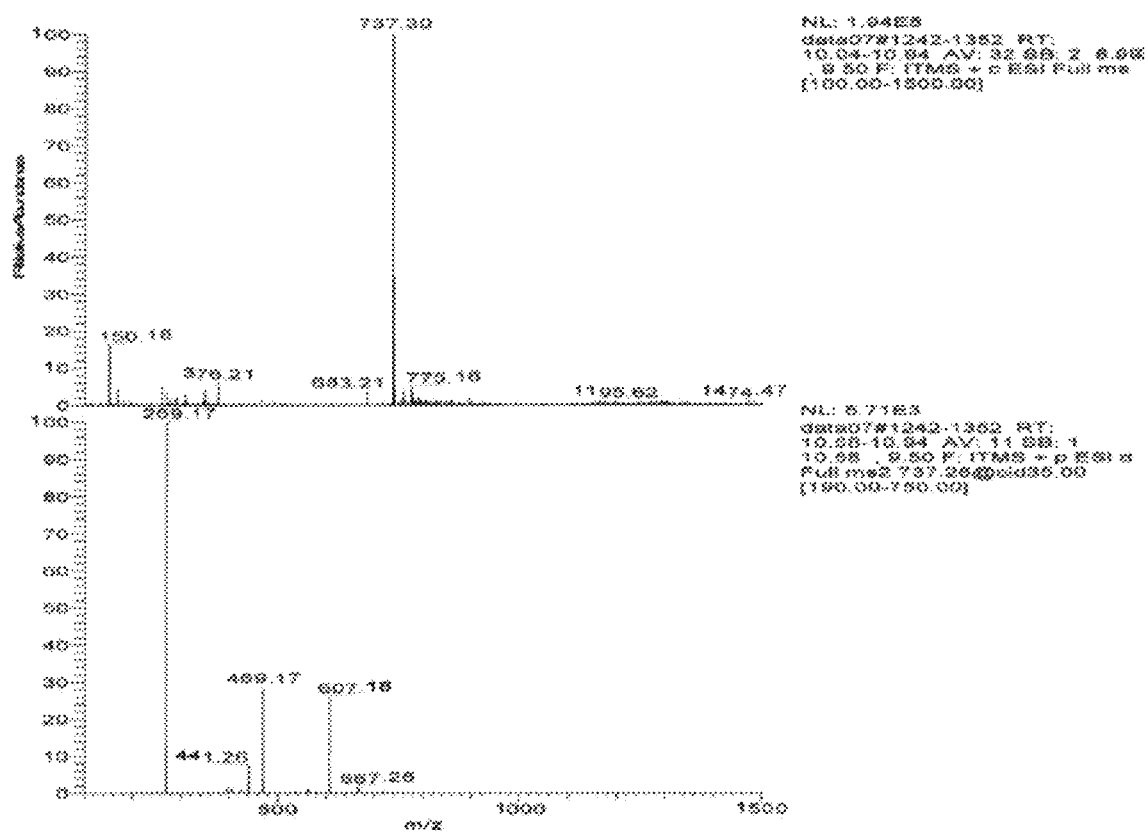
FIG. 14 shows the mass spectra obtained for the RRT 1.22 compound.
Figure 15:
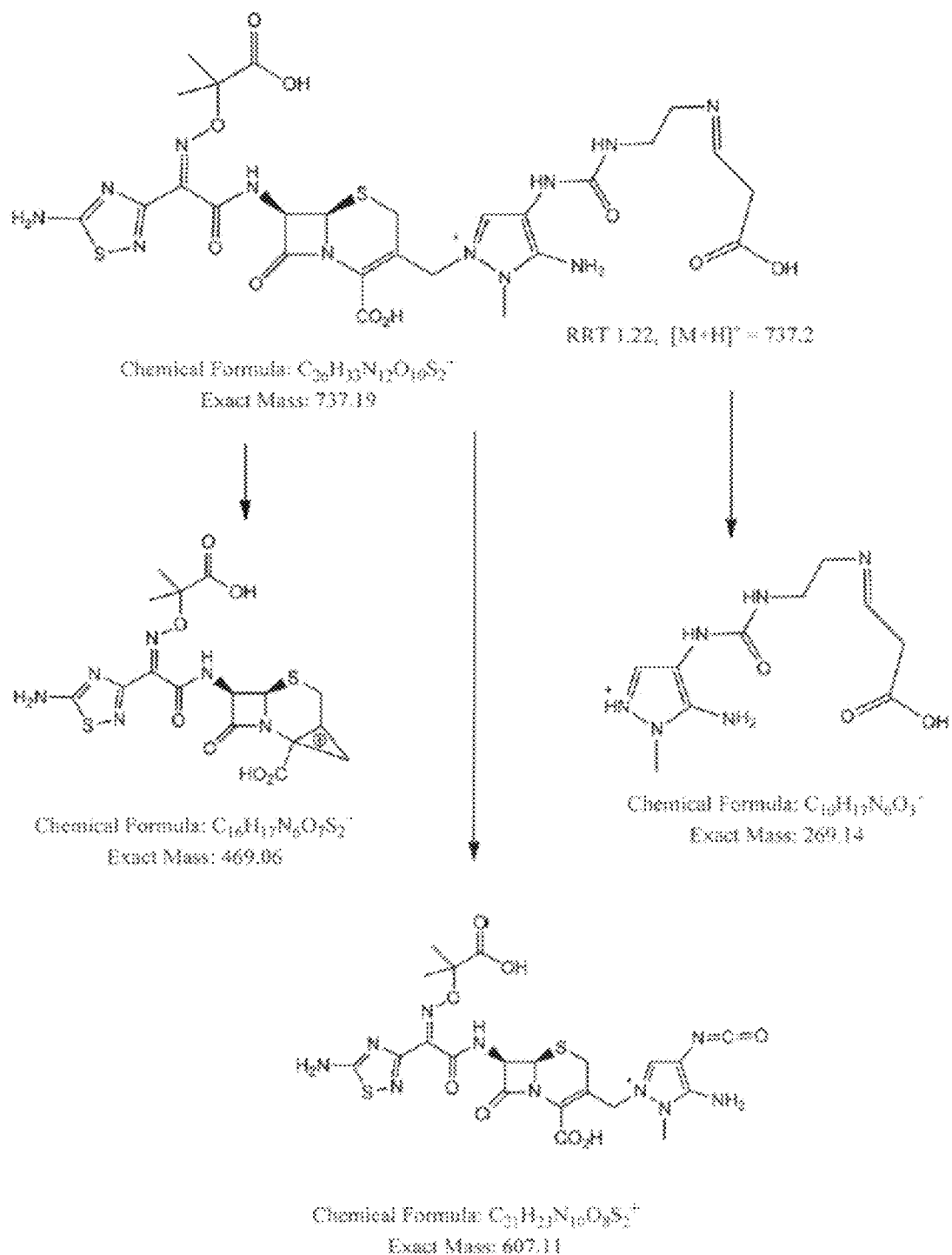
FIG. 15 shows the chemical structures for certain peaks in the spectra in FIG. 14.

The material obtained from the RRT 1.22 peak was analyzed by LC/MS, providing the spectra shown in FIG. 14. FIG. 15 (below) is the corresponding structures for the peaks shown in FIG. 14.

A test sample prepared from ceftolozane and tazobactam acid co-compounding solution containing RRT 1.22 impurity was used on the LC/MS experiment. Liquid chromatography separation was performed on a Zorbax SB C8, 3.5 µm, 3.0 mm×150 mm column, using gradient elution with 20 mM ammonium formate containing 0.1% Heptofluorobutyric acid pH 3.2 as mobile phase A and 0.1% Heptofluorobutyric acid in acetonitrile as mobile phase B. The gradient starts from 3% (initial) to 15% mobile phase B in 20 minutes (with RRT 1.22 eluting at about 10.7 minutes). Mass detection was performed using electrospray ionization technique under positive mode. The column effluent was also monitored at 254 nm using a photodiode-array detector. MS/MS fragmentation was performed on m/z 737.3 positive ion using nitrogen as collision gas, with collision energy set at 35V.

Example 8: Stabilizing Effect of Sodium Chloride in CXA-201 Compositions

A. Reduction of the Composition at RT=63 Minutes in CXA-201 Compositions

A stability study was carried out at 25° C. and analyzed by HPLC. CXA-201 compositions comprise ceftolozane and tazobactam, further comprising high, mid, or low amounts of sodium chloride (480, 125, or 62.5 mg NaCl per 1000 mg of ceftolozane, respectively). Comparison of the compositions are listed in Table 14. The amounts of the composition RT 63', as measured by the HPLC method, are summarized in Table 15.

TABLE 14

Comparison of the CXA-201 Compositions

| Lot | CXA-101 | NaCl | Tazobactam |
|---|---|---|---|
| C1 | 10% | High | Na |
| C2 | 20% | Mid | Na |
| C3 | 20% | Low | Na |
| C4 | 20% | Mid | Arginate |
| C5 | 20% | Low | Arginate |

TABLE 15

RT 63' Peak Area at t = 3 months, 25° C./60% RH storage

| Sample | Summary | 1st data collection RT | Area % | 2nd data collection RT | Area % | 3rd data collection RT | Area % |
|---|---|---|---|---|---|---|---|
| C1 | High salt + Tazo Na | 63.90 | 0.03 | 63.30 | 0.08 | 62.49 | 0.14 |
| C2 | Mid salt + Tazo Na | 63.78 | 0.06 | 63.12 | 0.12 | 62.45 | 0.28 |
| C3 | Low salt + Tazo Na | 63.75 | 0.12 | 63.11 | 0.14 | 62.46 | 0.29 |
| C4 | Mid salt + Tazo Arg | 63.76 | 0.10 | 63.16 | 0.13 | 62.44 | 0.28 |
| C5 | Low salt + Tazo Arg | 63.72 | 0.08 | 63.14 | 0.16 | 62.46 | 0.33 |

Conclusion:

At the three month time point, the reduced salt formulations were observed to be not as stable as the full salt formulation; and trends indicate that reduction in salt causes at least 1.5-fold greater composition at RT=63 minutes, as measured by HPLC. The compositions comprising 480 mg NaCl per 1000 mg of ceftolozane had the least amount of the composition RT 63' after 3 months at 25° C. The amount of the composition RT 63' in the compositions comprising 125 mg NaCl per 1000 mg of ceftolozane was 1.5-fold or greater than the amount of the composition 63' in the compositions comprising 480 mg NaCl per 1000 mg of ceftolozane. The amount of the composition RT 63' in the compositions comprising 62.5 mg NaCl per 1000 mg of ceftolozane was 2-fold or greater than the amount of the composition RT 63' in the compositions comprising 480 mg NaCl per 1000 mg of ceftolozane. Thus, the CXA-201 compositions comprising high amounts of sodium chloride (e.g., 125-1000 mg sodium chloride per 1000 mg of ceftolozane) were more chemically stable than the compositions comprising low amounts of sodium chloride (e.g., less than 125 mg sodium chloride per 1000 mg of ceftolozane).

B. Improvement in the Purity of Ceftolozane in CXA-201 Pharmaceutical Compositions with Varying Amounts of Sodium Chloride A stability study was carried out at 30° C. and 60° C. analyzed by HPLC. The sodium chloride content in the CXA-201 compositions is described in Table 16. The HPLC data at 60° C. are summarized in Tables 17-20. The data are also plotted in FIGS. 7-10 to show the trends of the purity, and the amounts of the composition peak 1, the composition with a RRT of 0.43 and the composition peak 3, and the composition peak 7 in the CXA-201 compositions with respect to NaCl.

TABLE 16

The Sodium Chloride Content in the CXA-201 Compositions

| Samples | NaCl content |
|---|---|
| B1 | 481.0 mg sodium chloride per 1000 mg of ceftolozane |
| B2 | 125.0 mg sodium chloride per 1000 mg of ceftolozane |
| B3 | 75.0 mg sodium chloride per 1000 mg of ceftolozane |
| B4 | 50.0 mg sodium chloride per 1000 mg of ceftolozane |

TABLE 17

The Purity of Ceftolozane in CXA-201 Compositions with Varying Amounts of Sodium Chloride

| | Day | B1 | B2 | B3 | B4 |
|---|---|---|---|---|---|
| t0 | 0 | 98.1 | 97.8 | 97.8 | 97.7 |
| 1 day/60° C. | 1 | 97.2 | 96.3 | 96.2 | 96.0 |
| 1 day/30° C. | 1 | 98.2 | 97.7 | 97.6 | 97.6 |
| 3 days/60° C. | 3 | 95.4 | 94.9 | 94.7 | 94.6 |
| ($\Delta_{t0-t3}$) | | (2.7) | (2.9) | (3.1) | (3.1) |
| 3 day/30° C. | 3 | 98.0 | 97.5 | 97.4 | 97.3 |
| 7 days/60° C. | 7 | 92.7 | 93.8 | 93.6 | 93.4 |
| 7 day/30° C. | 7 | 97.8 | 97.2 | 97.0 | 96.9 |
| Total Δ/60° C. | | 5.3 | 4.0 | 4.2 | 4.3 |
| Total Δ/30° C. | | 0.3 | 0.6 | 0.8 | 0.8 |

TABLE 18

The HPLC Peak Area of Composition Peak 1 in CXA-201 Compositions with Varying Amounts of Sodium Chloride

| | Day | B1 | B2 | B3 | B4 |
|---|---|---|---|---|---|
| t0 | 0 | 0.47 | 0.38 | 0.38 | 0.41 |
| 1 day/60° C. | 1 | 1 | 1.08 | 1.09 | 1.14 |
| 1 day/30° C. | 1 | 0.48 | 0.44 | 0.45 | 0.49 |
| 3 days/60° C. | 3 | 1.85 | 1.64 | 1.66 | 1.71 |

TABLE 18-continued

The HPLC Peak Area of Composition Peak 1 in CXA-201
Compositions with Varying Amounts of Sodium Chloride

|  | Day | B1 | B2 | B3 | B4 |
|---|---|---|---|---|---|
| 3 day/30° C. | 3 | 0.53 | 0.53 | 0.56 | 0.61 |
| 7 days/60° C. | 7 | 3.3 | 2.28 | 2.25 | 2.29 |
| 7 day/30° C. | 7 | 0.62 | 0.67 | 0.71 | 0.77 |
| INCREASE %/60 ° C. |  | 2.83 | 1.9 | 1.87 | 1.88 |
| INCREASE %/30 ° C. |  | 0.15 | 0.29 | 0.33 | 0.36 |

TABLE 19

The Total HPLC Peak Area of the Composition with a RRT of 0.43 and
Composition Peak 3 in CXA-201 Compositions with Varying Amounts
of Sodium Chloride

|  | Day | B1 | B2 | B3 | B4 |
|---|---|---|---|---|---|
| t0 | 0 | 0.15 | 0.12 | 0.12 | 0.12 |
| 1 day/60° C. | 1 | 0.36 | 0.35 | 0.31 | 0.32 |
| 1 day/30° C. | 1 | 0.13 | 0.12 | 0.13 | 0.12 |
| 3 days/60° C. | 3 | 0.92 | 0.67 | 0.65 | 0.62 |
| 3 days/30° C. | 3 | 0.17 | 0.16 | 0.17 | 0.16 |
| 7 days/60° C. | 7 | 1.29 | 0.78 | 0.75 | 0.71 |
| 7 days/30° C. | 7 | 0.19 | 0.19 | 0.20 | 0.20 |
| INCREASE %/60 ° C. |  | 1.14 | 0.66 | 0.63 | 0.59 |
| INCREASE %/30 ° C. |  | 0.04 | 0.07 | 0.08 | 0.08 |

TABLE 20

The HPLC Peak Area of Composition Peak 7 in CXA-201
Compositions with Varying Amounts of Sodium Chloride

|  | Day | B1 | B2 | B3 | B4 |
|---|---|---|---|---|---|
| t0 | 0 | 0.69 | 1.01 | 1.01 | 1.01 |
| 1 day/60° C. | 1 | 0.73 | 1.12 | 1.15 | 1.18 |
| 1 day/30° C. | 1 | 0.68 | 1.00 | 0.99 | 0.95 |
| 3 days/60° C. | 3 | 0.8 | 1.24 | 1.27 | 1.27 |
| 3 days/30° C. | 3 | 0.68 | 1.00 | 1.01 | 1.03 |
| 7 days/60° C. | 7 | 0.94 | 1.32 | 1.35 | 1.4 |
| 7 days/30° C. | 7 | 0.68 | 1.02 | 1.05 | 1.06 |
| INCREASE %/60° C. |  | 0.25 | 0.31 | 0.34 | 0.39 |
| INCREASE %/30° C. |  | NC | 0.01 | 0.04 | 0.05 |

Conclusion:

The stability data shows that high sodium chloride content enhances stability of CXA-201 compositions.

Similarly to CXA-101 compositions, CXA-201 compositions comprising high amounts of sodium chloride (e.g., 125-1000 mg sodium chloride per 1000 mg of ceftolozane) were found to be more chemically stable than CXA-201 compositions comprising low amounts of sodium chloride (e.g., less than 125 mg sodium chloride per 1000 mg of ceftolozane). Table 17 shows that, by day 3 of heating at 60° C., sample B1 containing the highest salt concentration is most stable, i.e., has the lowest $\Delta_{t0\text{-}t3}$ of all samples. By day 3, the sample with the lowest salt concentration, B4, has the highest $\Delta_{t0\text{-}t3}$ indicating the most degradation. Overall, B4 has degraded 15% more than B1.

Example 9: Manufacturing Process of a CXA-201 Composition (Comprising Tazobactam and Ceftolozane) by Blending A. Sterile Dry Blending of Bulk Lyophilized Ceftolozane and Bulk Lyophilized Tazobactam A low energy drum blender that agitates the material by tumbling and also moving the bed up and down is used. A representative process of blending is described as follows, also shown in FIG. 1. The blender was charged with 23.4 kg of CXA-101 bulk product, and 5.4 kg of tazobactam bulk product. Both the CXA-101 and tazobactam were individually lyophilized beforehand. The material was blended for 180 minutes. In-process tests of content assay for both CXA-101 and tazobactam were performed to assess the homogeneity using the samples of blend materials taken from three places. The relative standard deviation (RSD) for each of CXA-101 and tazobactam content assay was no greater than 2% and the RSD for the ratio of CXA-101/tazobactam was no greater than 2% (See Table 21).

TABLE 21

In-Process Testing of Blending Samples of a CXA-201 Composition at Three Places

| | | | Results | | |
|---|---|---|---|---|---|
| Test | Acceptance Limits (expected value) | Sampling | 60 minute | 120 minute | 180 minute |
| Content: Ceftolozane[1] | 30.4%-37.2% | 1 | 34.24 | 34.07 | 34.42 |
| | | 2 | 34.62 | 34.21 | 34.66 |
| | | 3 | 34.71 | 34.60 | 34.85 |
| | | Mean[3] | 34.52 | 34.30 | 34.64 |
| | | RSD % | 0.72 | 0.80 | 0.63 |
| Content: Tazobactam[2] | 15.2%-18.6% | 1 | 17.96 | 18.20 | 17.12 |
| | | 2 | 16.90 | 18.26 | 16.51 |
| | | 3 | 17.27 | 16.93 | 17.02 |
| | | Mean[3] | 17.38 | 17.80 | 16.89 |
| | | RSD % | 3.10 | 4.22 | 1.96 |

TABLE 21-continued

In-Process Testing of Blending Samples of a CXA-201 Composition at Three Places

| Test | Acceptance Limits (expected value) | Sampling | Results 60 minute | 120 minute | 180 minute |
|---|---|---|---|---|---|
| Ratio of Content (w/w) ceftolozane/tazobactam | 2.00[4] | 1 | 1.91 | 1.87 | 2.01 |
| | | 2 | 2.05 | 1.87 | 2.10 |
| | | 3 | 2.01 | 2.04 | 2.05 |
| | | Mean[3] | 1.99 | 1.93 | 2.05 |
| | | RSD % | 3.69 | 5.12 | 2.2 |

RSD = relative standard deviation
[1]Theoretical value: 33.96% Accetance limits are 90%-110% of the theoretical value.
[2]Theoretical value: 16.99% Acceptance limits are 90%-110% of the theoretical value.
[3]Three samples are taken at each time point at three places to measure the percentage by weight of ceftolozane and tazobactam. The "Mean" is the average of the percentages or the weight ratios of Ceftolozane/tazobactam.
[4]Acceptance limits were established based on batch history.

B. Packaging into STERBAGS®

The blended powder is then discharged into STERBAGS®.

C. Finished CXA-201 Drug Product

A fill and finish process is utilized for the final drug product, which is a pharmaceutical composition comprising CXA-101 and tazobactam at a ratio of 1000 mg/500 mg. Glass containers are washed with WFI and depyrogenated in a Class 100 depyrogenation tunnel at a temperature of 320° C. Pre-washed and pre-siliconized stoppers are autoclaved for 40 minutes at 121° C. The bulk drug product is packaged in a STERBAG® system comprised of three bags. The outer bag is cleaned with disinfectant in a Class 10,000 clean room. The bag system is placed in a pass-through UV box where it is subjected to UV radiation (>20 µW/cm$^2$) for 20 minutes to sterilize the surface of the outer bag. The outer bag is removed and left in the UV box. The middle bag is placed in a Class A laminar airflow (LAF) hood. The sterile middle bag is removed under LAF. The sterile, bottle-shaped inner bag is then placed in a sterile stainless steel carrier and attached to the filling machine.

Sterile bulk CXA-101/tazobactam drug product is filled under a nitrogen blanket into 30-mL, Type I clear glass containers. The sterile drug product is gravity-fed into the filling machine under LAF. container fill weights are periodically checked throughout the filling operation to ensure proper operation of the filling line. Filling and stoppering operations are performed under Class 100 LAF conditions. Capping and container washing are done in the Class 10,000 clean room.

Example 10: Assessment of Blend Combination Drug Product

A. Preparation of the Blend Combination Drug Product (CXA-201 Composition)

The blend drug product was prepared, as described above in Example 9, on lab scale using a small blender. The components of the blend composition are shown in Table 22.

TABLE 22

Components of the Blend Composition

| Component | | Composition | Quantity as active components |
|---|---|---|---|
| CXA-201 Comp. | CXA-101 for Injection Bulk (25 g) | Ceftolozane L-Arginine Citric acid Sodium chloride | 10.8 g 6.7 g 233 mg 5.2 g |
| | Tazobactam sodium sterile Bulk (6 g) | | 5.4 g (as Tazo free acid) |

B. Stressed Stability Test

Stability studies of this CXA-201 composition prepared by the blending process were carried out at 25° C. and 40° C. The composition was analyzed using HPLC method described in Example 1. The following Tables 23 and 24 are summaries of the HPLC measurements at time zero, after one month (T1), and after three months (T2).

TABLE 23

Stability Data of Blend CXA-201 Composition at 25 ° C./RH = 60%

| Test items | Specifications | T0 | T1 25° C. | T2 25° C. |
|---|---|---|---|---|
| Related Substances | | | | |
| Peak1 | ≤1.50% | 0.61% | 0.93% | 1.08% |
| Peak2 | ≤0.40% | <0.03% | <0.03% | <0.03% |
| Peak3 | ≤0.30% | <0.03% | <0.03% | <0.03% |
| Peak4 | ≤0.80% | 0.03% | 0.03% | 0.04% |
| Peak5 | ≤1.00% | 0.09% | 0.12% | 0.13% |
| Peak6 | ≤0.15% | <0.03% | <0.03% | <0.03% |
| Peak7 | ≤2.00% | 1.28% | 1.34% | 1.35% |
| Peak8 | ≤0.15% | <0.03% | <0.03% | <0.03% |
| Peak9 | ≤0.60% | 0.03% | <0.03% | 0.03% |
| Peak10, 11 | ≤0.30% | <0.03% | 0.04% | 0.05% |
| Sing. Unk. | ≤0.15% | 0.13% | 0.13% | 0.14% |
| Total | ≤5.00% | 2.49% | 3.03% | 3.28% |
| Assay CXA-101 | Teor. % = 32.6% | 32.5% | n.a. | n.a. |
| Assay Tazobactam | Teor. % = 17.4% | 18.2% | n.a. | n.a. |
| Tazobactam Related Compound A | ≤4.0% | 0.07% | 0.12% | 0.14% |
| K.F. | ≤4.0% | 2.6% | n.a. | n.a. |
| pH | 5.0-7.0 | 6.0 | 5.6 | 5.1 |

TABLE 24

Stability Data of Blend CXA-201 Composition at 40° C./RH = 75%

| Test items | Specifications | T0 | T1 40° C. | T2 40° C. |
|---|---|---|---|---|
| Related Substances | | | | |
| Peak1 | ≤1.50% | 0.61% | 1.66% | 2.28% |
| Peak2 | ≤0.40% | <0.03% | <0.03% | <0.03% |
| Peak3 | ≤0.30% | <0.03% | <0.03% | 0.04% |
| Peak4 | ≤0.80% | 0.03% | 0.04% | 0.05% |
| Peak5 | ≤1.00% | 0.09% | 0.13% | 0.14% |

TABLE 24-continued

Stability Data of Blend CXA-201 Composition at 40° C./RH = 75%

| Test items | Specifications | T0 | T1 40° C. | T2 40° C. |
|---|---|---|---|---|
| Peak6 | ≤0.15% | <0.03% | <0.03% | <0.03% |
| Peak7 | ≤2.00% | 1.28% | 1.41% | 1.46% |
| Peak8 | ≤0.15% | <0.03% | <0.03% | <0.03% |
| Peak9 | ≤0.60% | 0.03% | <0.03% | 0.03% |
| Peak10, 11 | ≤0.30% | <0.03% | 0.08% | 0.09% |
| Sing. Unk. | ≤0.15% | 0.13% | 0.14% | 0.13% |
| Total | ≤5.00% | 2.49% | 4.21% | 5.27% |
| Assay CXA-101 | Teor. % = 32.6% | 32.5% | n.a. | n.a. |
| Assay Tazobactam | Teor. % = 17.4% | 18.2% | n.a. | n.a |
| Tazobactam Related Compound A | ≤4.0% | 0.07% | 0.35% | 0.54% |
| K.F. | ≤4.0% | 2.6% | n.a. | n.a. |
| pH | 5.0-7.0 | 6.0 | 5.0 | 4.4 |

C. Conclusion

The data at both 25° C. and at 40° C. have shown that the blending process completely inhibits formation of the compound RRT=1.22.

Example 11: Alkalizing Agent Selection

Compositions for intravenous administration should be formulated to resemble the and pH of human blood to reduce vascular complications. The recommended pH is between 5 and 9 (ideal pH is as close to 7.4 as possible). Departing from this recommended pH ranges of an intravenously administered composition can result in the development of complications such as phlebitis, or inflammation of the veins. Marc Stranz, *A Review of pH and Osmolarity*, 6 Int'l J. of Pharm. Compounding 216, 218 (May/June 2002). Unfortunately, few drug infusions are stable at a suitable pH for intravenous administration. Depending on the molecular structure, a drug is most stable or has the best solubility at a particular pH range (e.g., pH<6) and divergence from this pH range may lead to increased drug decomposition. It is thus challenging to find a balance between the safe limits of pH and optimum drug stability in compositions for intravenous administration. Marc Stranz, *The Implications of Osmolality, Osmolarity and pH in Infusion Therapy*, INS Annual Conference (May 2005).

A formulation close to physiologic pH was targeted. This necessitates an alkalizing agent due to intrinsic pH 1.92 of ceftolozane in solution (2%). The initial study of alkalizing agents included sodium hydroxide, L-arginine, tris, sodium bicarbonate, meglumine, diethanolamine, and triethanolamine. Samples containing 100 mg ceftolozane sulfate, 22.9 mg sodium chloride, 200 mg maltose, and 2 mg citric acid anhydrous were prepared and adjusted to ~pH 4. The samples were lyophilized and powders stored at 70° C. for 3 days, 60° C. for 3, 6 and 9 days and at 40° C. for one month. The stored samples were then analyzed for ceftolozane content. Results are reported below in Table 25:

TABLE 25

Effect of Alkalizing Agent on Ceftolozane Recovery

| Storage ↓ | Sodium hydroxide | L-arginine | Tris | Sodium bicarbonate | Meglumine | Diethanolamine | Triethanolamine |
|---|---|---|---|---|---|---|---|
| 70° C., 3 d | 93.3 | 93.0 | 83.1 | 93.8 | 71.2 | 52.7 | 28.0 |
| 60° C., 3 d | 97.0 | 96.3 | 93.5 | 93.9 | 94.4 | 91.6 | 67.2 |
| 60° C., 6 d | 95.7 | 95.5 | 89.8 | 96.0 | 89.8 | 83.6 | 59.0 |
| 60° C., 9 d | 93.9 | 93.1 | 87.5 | 93.8 | 88.7 | 82.0 | 75.9 |
| 40° C./75% RH, 1 mo | 97.3 | 97.0 | 95.1 | 97.6 | 97.6 | 94.4 | 94.4 |

Ceftolozane recovery was consistently above 90% in the presence of sodium hydroxide, L-arginine, or sodium bicarbonate. Although sodium hydroxide performed well, as a strong base, it could promote base hydrolysis of the active more readily during scale up and be more difficult to dry during lyophilization than other alkalizing agents. Accordingly sodium hydroxide was not considered for further formulation development. L-arginine was thus chosen as the alkalizing agent for the formulation.

To ensure suitability of L-arginine as an alkalizing agent, a study was conducted to compare L-arginine against sodium bicarbonate. In this study, solutions were prepared to contain ceftolozane in the presence of sodium chloride and citric acid adjusted to approximately pH 6 with either L-arginine or sodium bicarbonate. The solutions were then lyophilized and samples distributed for accelerated and regular storage. A summary of the total additional compounds and pH for the various conditions after 1 month is presented in Table 26.

TABLE 26

Effect of L-Arginine and Sodium Bicarbonate on Ceftolozane Related Substances during Storage, pH 6

| | Bulk solution composition per 1000 mg ceftolozane free base | | | |
|---|---|---|---|---|
| | 632 mg L-arginine 485 mg sodium chloride 21 mg citric acid | | 288 mg sodium bicarbonate 481 mg sodium chloride 21 mg citric acid | |
| Storage condition | Total Related Substances | Sample pH | Total Related Substances | Sample pH |
| Initial | 1.42% | 5.8 | 2.12% | 5.8 |
| 5° C., 1 month | 1.38% | 5.8 | 2.66% | 5.6 |
| 25° C., 1 month | 1.74% | 5.5 | 4.99% | 4.8 |
| 40° C., 1 month | 2.32% | 5.0 | 5.93% | 4.5 |

As seen in the table the bicarbonate-adjusted sample showed a larger increase in related substances and a less stable pH profile. Accordingly, it was decided to maintain L-arginine as the alkalizing agent in the formulation.

Example 12: Components of a CXA-201 Composition

An example of a batch formulae for ceftolozane composition (compounding of ceftolozane substance with excipients such as citric acid, sodium chloride, and L-arginine followed by sterile lyophilization) is found below in Table 27.

TABLE 27

Batch Formula for Ceftolozane composition

| Component | Target Composition mg/g | Amount per Batch (kg) 1 | Amount per Batch (kg) 2 |
|---|---|---|---|
| Ceftolozane Sulfate[i] | 172.1 | 114.0 | 202.6 |
| Citric Acid, Anhydrous, USP | 3.2 | 2.1 | 3.7 |
| Sodium Chloride, USP | 73.1 | 48.3 | 86.0 |
| L-Arginine, USP | ~90 QS to achieve target pH[ii] | 59.7 | 106.0 |
| Water for Injection, USP | QS to 1000 | QS | QS |
| Total Batch Size | | 660 | 1175 |

[i]Ceftolozane sulfate is charged based on its measured potency to obtain 150 mg free base/g solution.
[ii]L-arginine is added as needed to obtain pH 6.5 ± 0.5 in the bulk solution; 90 mg per gram solution is considered a representative amount.

An example of a batch formula for the ceftolozane/tazobactam drug product is presented in Table 28 below.

TABLE 28

Batch Formula Ceftolozane/Tazobactam Drug Product Composition

| Component | Amount per container, mg | Amount per Batch, kg |
|---|---|---|
| Ceftolozane composition[i] | 2255 | 112.8 |
| Tazobactam[ii] | 537 | 26.9 |
| Nitrogen, NF[iii] | — | — |
| Total | 2792 | 139.7 |
| Total Batch Size, kg | | 139.7 |
| Total container Quantity | | 50,000 |

[i]The target fill for ceftolozane is 1000 mg free base, added to the container as the composition. The amount 2255 mg is based on 100% theoretical potency of the composition. Actual weight will vary based on composition measured potency.
[ii]The target fill for tazobactam is 500 mg free acid, added to the container as its sodium salt form. The amount 537 mg is based on 100% theoretical potency.
[iii]Nitrogen is used as a processing aid to blanket containers after powder filling and prior to insertion of stopper.

The unit composition of a dosage for reconstitution is described in Table 29.

TABLE 29

Unit Compositions of Ceftolozane/Tazobactam for Injection, 1000 mg/500 mg

| Component | | Function | Nominal Composition mg per container |
|---|---|---|---|
| Ceftolozane composition[1] | Ceftolozane Sulfate | Active | 1147 |
| | Citric Acid, Anhydrous | Chelating Agent | 21 |
| | Sodium Chloride | Stabilizing Agent | 487 |

TABLE 29-continued

Unit Compositions of Ceftolozane/Tazobactam for Injection, 1000 mg/500 mg

| Component | Function | Nominal Composition mg per container |
|---|---|---|
| L-Arginine | Alkalizing Agent | 600[2] Q.S. for pH adjustment |
| Tazobactam Sodium[3] | Active | 537 |
| Nitrogen | Processing Aid[a] | Q.S. |
| Total Weight | | 2792 |

[1]Actual amount of ceftolozane composition will vary based on the measured potency. Ceftolozane sulfate, 1147 mg, corresponds to 1000 mg ceftolozane free base.
[2]L-arginine is added as needed to achieve pH 6.5 ± 0.5; 600 mg per container is considered a representative total amount.
[3]Actual weight of tazobactam sodium will vary based on the measured potency. Tazobactam sodium 537 mg, corresponds to 500 mg tazobactam free acid
4) Nitrogen blanket is applied after powders are dispensed to the container and prior to insertion of stopper.

Example 12a: Development and Implementation of a System to Prevent Cross-Contamination in Accordance with FDA Guidance A recently published (April 2013) Food and Drug Administration Guidance for Industry *Non Penicillin Beta-Lactam Drugs: A CGMP Framework for Preventing Cross-Contamination* provides direction on prevention of cross-contamination for facilities that manufacture non-penicillin beta-lactam drugs. Provided herein are steps for the development and implementation of a system to prevent cross-contamination due to the introduction of both sterile ceftolozane drug product intermediate and tazobactam sodium into a facility that is in conformance with FDA Guidance.

Segregation steps to conform with FDA Guidance can include, but are not limited to:

Relocation all other drug products to other sites

Separating the ceftolozane/tazobactam product filling line and the veterinary cephapirin product filling line Creating separate HVAC systems Establishing separate warehouse areas Formalizing separate material, waste and personnel flows Constructing temporary facilities for gowning and entrance to the line used for the ceftolozane/tazobactam drug product.

Constructing new walls, modifying and reinforcing existing walls

Equipping the existing emergency egress with alarms and gaskets to completely separate both lines throughout all the floors of the building Creating the permanent separation of locker, rest and break rooms for both lines of the facility:

Dedicated maintenance and operations personnel for each part of the facility including different uniform colors for each part of the facility Dedicated equipment and tools for each part of the facility An Emergency Recovery plan

Example 13: Physicochemical and Biological Properties Ceftolozane/Tazobactam for Injection, 1000 mg/500 mg As a product intended for intravenous use, several properties are important for physiological compatibility. These include particulate matter, sterility, endotoxin limit, pH, and osmolality. Particulate matter and sterility are controlled at the point of manufacture. The drug product is processed aseptically throughout the entire manufacturing process, inclusive of ceftolozane, tazobactam sodium, and ceftolozane/tazobactam in-container drug product.

The ceftolozane/tazobactam drug product is controlled to approximately pH 6, to provide physiological comfort, while still assuring adequate stability for the drug substances. The ceftolozane drug product intermediate is controlled during compounding to pH 6.5±0.5 and is controlled at release to pH 5 to 7. The tazobactam sodium is controlled at release to pH 5 to 7.

Ceftolozane/tazobactam following reconstitution with normal saline and dilution for infusion also in normal saline (10 mg/mL ceftolozane; 5 mg/mL tazobactam) is slightly hypertonic, with osmolality approximately 500 mOsm/kg. However, slightly hypertonic intravenous infusion solutions are not uncommon as drug products are commonly prepared and diluted with already-isotonic solutions, such as normal saline. The generally accepted maximum upper limit for peripheral intravenous administration is approximately 900 mOsm/kg, though admixtures 600 to 900 mOsm/kg are typically administered through a central line. Therefore, to be within the limits of this range, the infusion product is less than 600 mOsm/kg.

Example 14: Determining Osmolality of CXA-201 Compositions

CXA-101 and Tazobactam Sodium samples (#1-#3) were reconstituted as follows:
Sample#1: Weighed 0.103 g of Tazobactam Sodium and 0.462 g of CXA-101 dissolved in 4 mL of WFI Water and 6 mL of USP Normal Saline.
Sample#2: Weighed 0.103 g of Tazobactam Sodium and 0.462 g of CXA-101 dissolved in 4 mL of WFI Water added 10 mL of USP Normal Saline.
Sample#3: Weighed 0.103 g of Tazobactam Sodium dissolved in 1 mL of WFI Water and 0.462 g of CXA-101 dissolved in 1 mL of WFI Water then mixed together added 10 mL of USP Normal Saline.
Tazobactam Sodium (Potency: 97.5%)
CXA-101 (Potency: 43.3%)
WFI Water
USP Normal Saline The osmolality of CXA-101 and Tazobactam Sodium samples (#1-#3) was then determined using a freezing point depression Osmometer (available from Advanced Instruments, Inc.).

A unit dosage form composition of Table 29 was reconstituted with 10 mL of Sterile WFI or USP Normal Saline then added into 100 mL 5% Dextrose Injection (D5W) or 0.9% Sodium Chloride (NS) bags and the osmolality of the resulting bag solution was determined as shown in table Table 30B below.

TABLE 30B

| Osmolarity of Ceftolozane Bag Solution (mOsm/kg) | | | | |
|---|---|---|---|---|
| Time Point | sWFI-D5W | NS-D5W | sWFI-NS | NS-NS |
| RT T0 | 446 | 470 | 449 | 478 |

In Table 30B, data for osmolality of the following product reconstitution scenarios was determined using the composition from Table 29

5% Dextrose Injection USP, 100 mL Bag (Baxter)
0.9% Sodium Chloride Injection USP, 100 mL Bag (Baxter)
sWFI—D5W: reconstituted with Sterile WFI then added into 5% Dextrose Injection bag
NS—D5W: reconstituted with USP Normal Saline then added into 5% Dextrose Injection bag
sWFI—NS: reconstituted with Sterile WFI then added into 0.9% Sodium Chloride Injection Bag
NS—NS: reconstituted with USP Normal Saline then added into 0.9% Sodium Chloride Injection bag

Example 15: Excipients in Ceftolozane Drug Product Intermediate

The excipients in exemplary ceftolozane compositionswere chosen to ensure stability and processability of the ceftolozane drug substance into the drug product. The specific excipients, their quantities and functions are provided in Table 31. All excipients are compendial and typical for sterile pharmaceutical dosage forms, requiring no additional treatment prior to use in the formulation. The excipients are used in levels within the range established in other FDA approved products as described in the Inactive Ingredients Database (IID).

TABLE 30A

| Osmolality of Reconstituted Solutions | | | | | |
|---|---|---|---|---|---|
| Sample# | CXA-101 Conc. (mg/ml) | Tazobactam Sodium Conc. (mg/ml) | WFI Water | Saline | Osmolality (mOsm/kg) |
| 1 | 20.0 | 10.0 | 40% (40 mL) | 60% (60 mL) | 589 |
| 2 | 14.3 | 7.1 | 29% (40 mL) | 71% (100 mL) | 512 |
| 3 | 16.7 | 8.3 | 17% (20 mL) | 83% (100 mL) | 604 |

TABLE 31

Excipients Used in Ceftolozane Composition

| Component | Function | Amount, mg/container | Concentration in Infusion Solution, % | Rationale for Inclusion | Inactive Ingredients Database (IID) Range |
|---|---|---|---|---|---|
| Citric acid | Chelating agent | 21 | 0.02 | Used to prevent discoloration and degradation | 0.0025 to 50% |
| Sodium Chloride | Stabilizing agent | 487 | 0.49 | Used as a stabilizing agent for ceftolozane sulfate | 0.187 to 45% |
| L-arginine | Alkalizing agent | 600[a] Q.S. for pH adjustment | 0.60 | Used to adjust ceftolozane solution pH | 0.29 to 88% |

[a]L-arginine is added as needed to achieve pH 6.5 ± 0.5; 600 mg per container is considered a representative total amount.

Example 16: Manufacturing Process of a CXA-201 Composition (Comprising Tazobactam and Ceftolozane) by Co-Filling The ceftolozane/tazobactam finished drug product is a sterile powder fill of lyophilized active ingredients ceftolozane drug product intermediate (composition) and tazobactam sodium together into a sterile single container. The lyophilized form of the sterile tazobactam sodium contains no excipients. Ceftolozane sulfate drug substance is converted first into a sterile drug product intermediate, composition, by formulation with citric acid, sodium chloride and L-arginine, followed by lyophilization.

Figure 12:
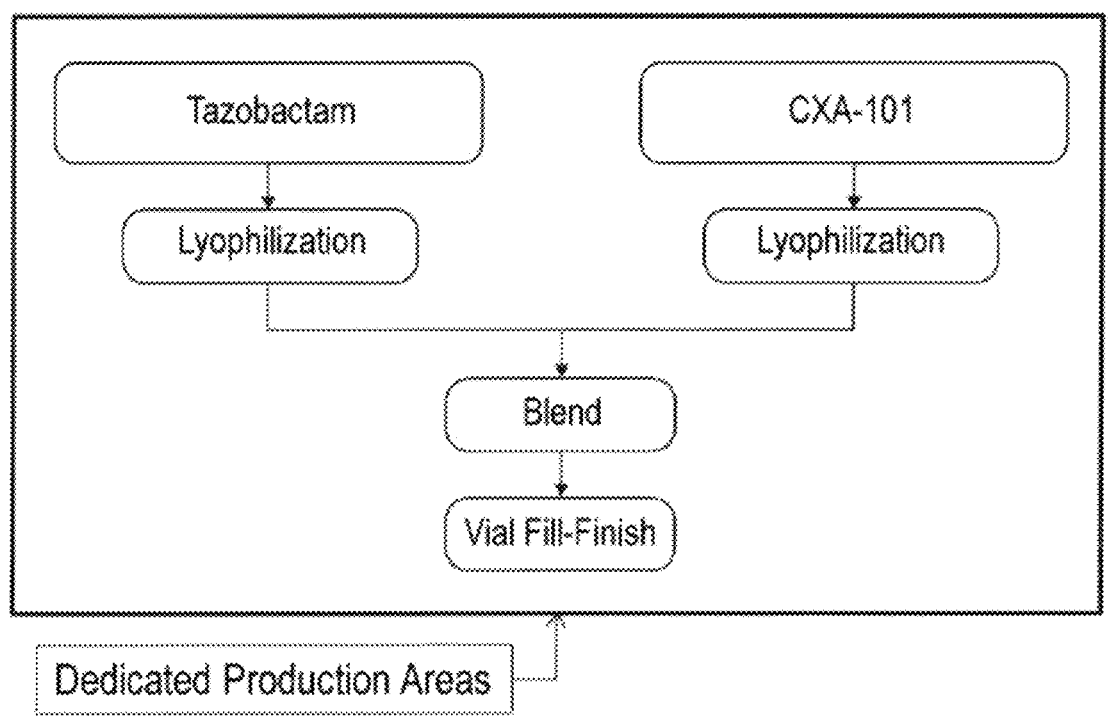
FIG. 12 is a flowchart showing the process for preparing a CXA-201 composition comprising ceftolozane (referred to as CXA-101) and tazobactam using a blending process in a dedicated production area according to FDA Guidance.
Figure 13:
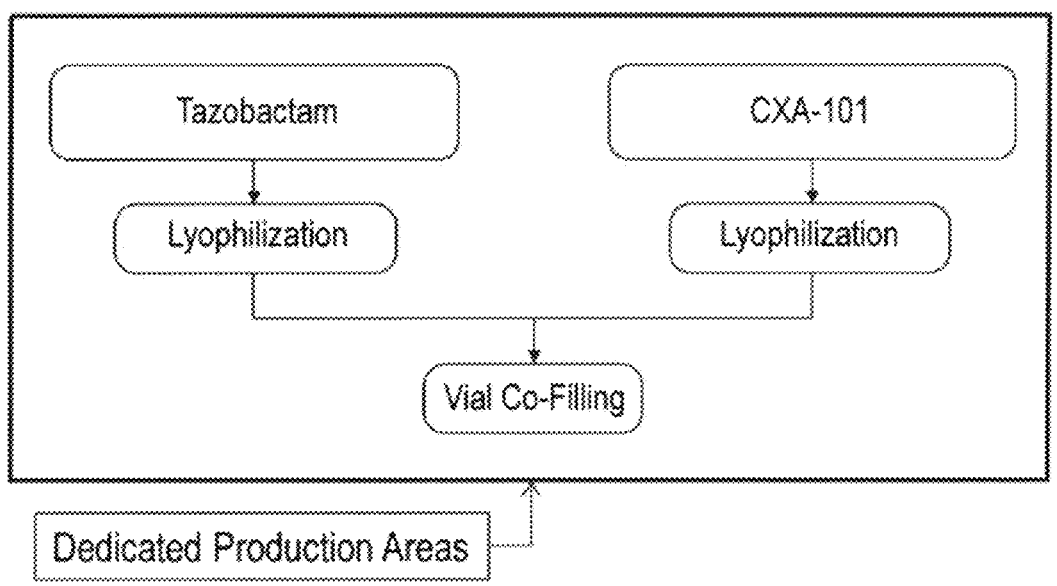
FIG. 13 is a flowchart showing the process for preparing a ceftolozane/tazobactam composition via co-filling in a dedicated production area according to FDA Guidance.

The full manufacturing process includes unit operations typical of an aseptic lyophilization process and aseptic powder filling process. The overall process can be outlined in two stages, as presented in the manufacturing flow chart of FIG. 12. The first stage is the manufacturing of the sterile ceftolozane composition. The second stage is the filling of the sterile drug powders into containers for the final drug product. The major process steps are:

Preparation of the sterile ceftolozane composition comprises
    compounding the bulk solution for lyophilization;
    sterile filtering the bulk solution;
    lyophilizing the bulk solution into bulk powder;
    grinding and sieving of the sterile bulk powder; and
    aseptic packaging of the sterile bulk powder in Sterbags®.
Filling of the sterile bulk powders comprises
    receipt of ceftolozane and tazobactam sterile powders at site;
    aseptic filling both sterile powders into the container sequentially;
    blanketing the container with a nitrogen headspace;
    stoppering and crimping the container; and
    inspecting the container prior to secondary packaging.

What is claimed is:

1. A method for treating an infection selected from the group consisting of a complicated intra-abdominal infection and a complicated urinary tract infection in a human patient in need thereof comprising administering to the patient a therapeutically effective amount of a pharmaceutical composition comprising ceftolozane sulfate and tazobactam sodium, said composition comprising less than 0.15% of a compound of formula (III)

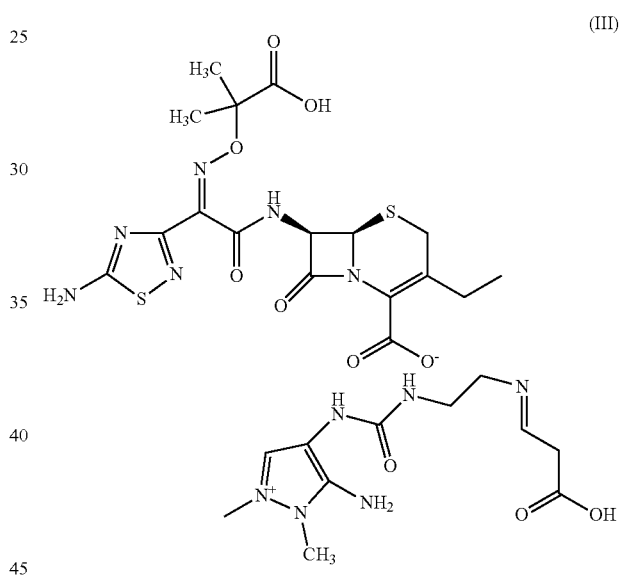

(III)

relative to ceftolozane sulfate, as determined by high performance liquid chromatography (HPLC) at a wavelength of 254 nm, when stored as a solid for 1 month at a temperature of 25° C. and at a relative humidity of 60%, wherein the ceftolozane sulfate and tazobactam sodium provide ceftolozane active and tazobactam active in a ratio of 2:1 by weight.

2. The method of claim 1, wherein the infection is a complicated intra-abdominal infection.

3. The method of claim 1, wherein the infection is a complicated urinary tract infection.

4. The method of claim 1, wherein the composition contains less than 0.1% of the compound of formula (III) relative to ceftolozane sulfate, as determined by high performance liquid chromatography (HPLC) at a wavelength of 254 nm, when stored as a solid for 1 month at a temperature of 25° C. and at a relative humidity of 60%.

5. The method of claim 1, wherein the composition contains less than 0.03% of the compound of formula (III)

relative to ceftolozane sulfate, as determined by high performance liquid chromatography (HPLC) at a wavelength of 254 nm when stored as a solid for 1 month at a temperature of 25° C. and at a relative humidity of 60%.

6. The method of claim 1, wherein the amount of ceftolozane active in the pharmaceutical composition is 1,000 mg and the amount of tazobactam active in the pharmaceutical composition is 500 mg.

7. The method of claim 1, wherein the amount of ceftolozane active in the pharmaceutical composition is 2,000 mg and the amount of tazobactam active in the pharmaceutical composition is 1,000 mg.

8. The method of claim 1, wherein the composition comprises 1,147 mg ceftolozane sulfate and 537 mg tazobactam sodium.

9. The method of claim 1, wherein the composition is provided in a unit dosage form.

10. The method of claim 1, wherein the pharmaceutical composition is dissolved in a pharmaceutically acceptable carrier and administered by parenteral administration.

11. The method of claim 1, wherein the pharmaceutical composition is dissolved in a pharmaceutically acceptable carrier and administered by intravenous infusion.

12. The method of claim 2, wherein the pharmaceutical composition is dissolved in a pharmaceutically acceptable carrier and administered by intravenous infusion.

13. The method of claim 3, wherein the pharmaceutical composition is dissolved in a pharmaceutically acceptable carrier and administered by intravenous infusion.

14. A method for treating an infection selected from the group consisting of a complicated intra-abdominal infection and a complicated urinary tract infection in a human patient in need thereof comprising administering to the patient a therapeutically effective amount of a pharmaceutical composition comprising ceftolozane sulfate and tazobactam sodium, said composition comprising less than 0.15% of the compound of formula (III)

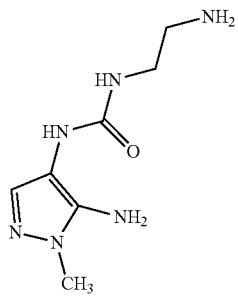

(IV)

relative to ceftolozane sulfate, as determined by high performance liquid chromatography (HPLC) at a wavelength of 254 nm, when stored as a solid for 3 months at a temperature of 25° C. and at a relative humidity of 60%, wherein the ceftolozane sulfate and tazobactam sodium provide ceftolozane active and tazobactam active in a ratio of 2:1 by weight.

15. The method of claim 14, wherein the infection is a complicated intra-abdominal infection.

16. The method of claim 14, wherein the infection is a complicated urinary tract infection.

17. The method of claim 14, wherein the composition contains less than 0.05% of the compound of formula (III) relative to ceftolozane sulfate, as determined by high performance liquid chromatography (HPLC) at a wavelength of 254 nm, when stored as a solid for 3 months at a temperature of 25° C. and at a relative humidity of 60%.

18. The method of claim 14, wherein the pharmaceutical composition is dissolved in a pharmaceutically acceptable carrier and administered by intravenous infusion.

19. A method for treating an infection selected from the group consisting of a complicated intra-abdominal infection and a complicated urinary tract infection in a human patient in need thereof comprising administering to the patient a therapeutically effective amount of a pharmaceutical com-

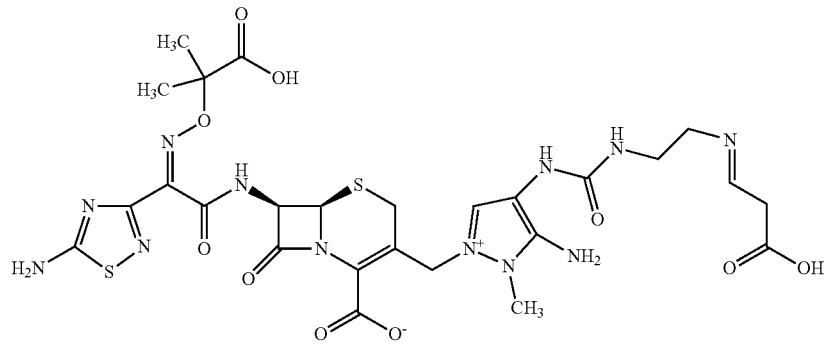

(III)

relative to ceftolozane sulfate, as determined by high performance liquid chromatography (HPLC) at a wavelength of 254 nm, and less than 1.5% of a compound of formula (IV)

position comprising ceftolozane sulfate and tazobactam sodium, said composition comprising less than 0.15% relative to ceftolozane sulfate of the compound having a mass spectra depicted in FIG. 14, as determined by high performance liquid chromatography (HPLC) at a wavelength of 254 nm, when stored as a solid for 1 month at a temperature of 25° C. and at a relative humidity of 60%, wherein the ceftolozane sulfate and tazobactam sodium provide ceftolozane active and tazobactam active in a ratio of 2:1 by weight.

20. The method of claim 19, wherein the infection is a complicated intra-abdominal infection.

21. The method of claim 19, wherein the infection is a complicated urinary tract infection.

22. The method of claim 19, wherein the composition contains less than 0.1% relative to ceftolozane sulfate of the compound with the mass spectra depicted in FIG. 14, as determined by high performance liquid chromatography (HPLC) at a wavelength of 254 nm, when stored as a solid for 1 month at a temperature of 25° C. and at a relative humidity of 60%.

23. The method of claim 19, wherein the composition contains less than 0.03% relative to ceftolozane sulfate of the compound with the mass spectra depicted in FIG. 14, as determined by high performance liquid chromatography (HPLC) at a wavelength of 254 nm, when stored as a solid for 1 month at a temperature of 25° C. and at a relative humidity of 60%.

24. The method of claim 19, wherein the amount of ceftolozane active in the pharmaceutical composition is 1,000 mg and the amount of tazobactam active in the pharmaceutical composition is 500 mg.

25. The method of claim 19, wherein the amount of ceftolozane active in the pharmaceutical composition is 2,000 mg and the amount of tazobactam active in the pharmaceutical composition is 1,000 mg.

26. The method of claim 19, wherein the composition comprises 1,147 mg ceftolozane sulfate and 537 mg tazobactam sodium.

27. The method of claim 19, wherein the pharmaceutical composition is dissolved in a pharmaceutically acceptable carrier and administered by intravenous infusion.

28. A method for treating an infection selected from the group consisting of a complicated intra-abdominal infection and a complicated urinary tract infection in a human patient in need thereof comprising administering to the patient a therapeutically effective amount of a pharmaceutical composition comprising ceftolozane sulfate and tazobactam sodium, said composition comprising less than 0.15% relative to ceftolozane sulfate of a compound having a mass spectra depicted in FIG. 14, as determined by high performance liquid chromatography (HPLC) at a wavelength of 254 nm, and less than 1.5% of a compound of formula (IV):

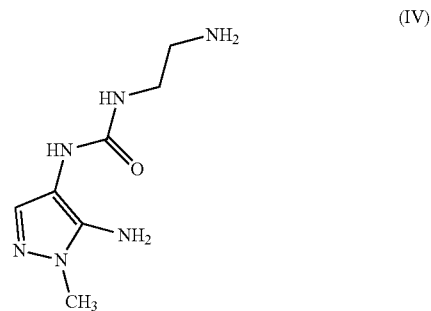

relative to ceftolozane sulfate, as determined by high performance liquid chromatography (HPLC) at a wavelength of 254 nm, when stored as a solid for 3 months at a temperature of 25° C. and at a relative humidity of 60%, wherein the ceftolozane sulfate and tazobactam sodium provide ceftolozane active and tazobactam active in a ratio of 2:1 by weight.

29. The method of claim 28, wherein the infection is a complicated intra-abdominal infection.

30. The method of claim 28, wherein the infection is a complicated urinary tract infection.

31. The method of claim 28, wherein the pharmaceutical composition is dissolved in a pharmaceutically acceptable carrier and administered by intravenous infusion.

* * * * *